United States Patent
Suderman et al.

(10) Patent No.: US 10,919,981 B2
(45) Date of Patent: Feb. 16, 2021

(54) AFFINITY PROTEINS AND USES THEREOF

(71) Applicant: Nectagen, Inc., Kansas City, KS (US)

(72) Inventors: Richard J. Suderman, Shawnee, KS (US); David M. Chao, Kansas City, MO (US); Daren Rice, Lee Summit, MO (US)

(73) Assignee: Nectagen, Inc., Kansas City, KS (US)

( * ) Notice: Subject to any disclaimer, the term of this patent is extended or adjusted under 35 U.S.C. 154(b) by 0 days.

(21) Appl. No.: 15/503,287

(22) PCT Filed: Aug. 24, 2015

(86) PCT No.: PCT/US2015/046588
§ 371 (c)(1),
(2) Date: Feb. 10, 2017

(87) PCT Pub. No.: WO2016/029220
PCT Pub. Date: Feb. 25, 2016

(65) Prior Publication Data
US 2017/0233496 A1 Aug. 17, 2017

Related U.S. Application Data

(60) Provisional application No. 62/040,772, filed on Aug. 22, 2014.

(51) Int. Cl.
| C07K 16/00 | (2006.01) |
| C07K 16/42 | (2006.01) |
| C07K 16/18 | (2006.01) |
| C07K 16/40 | (2006.01) |
| C07K 16/12 | (2006.01) |
| C12N 15/10 | (2006.01) |

(52) U.S. Cl.
CPC .......... *C07K 16/4283* (2013.01); *C07K 16/00* (2013.01); *C07K 16/1228* (2013.01); *C07K 16/1232* (2013.01); *C07K 16/18* (2013.01); *C07K 16/40* (2013.01); *C12N 15/1044* (2013.01); *C07K 2318/20* (2013.01)

(58) Field of Classification Search
None
See application file for complete search history.

(56) References Cited

U.S. PATENT DOCUMENTS

2011/0066111 A1   3/2011   Teschner et al.

FOREIGN PATENT DOCUMENTS

| CA | 2344763 A1 | 4/2000 |
| WO | WO-2006/092099 A1 | 9/2006 |
| WO | WO-2009/117085 A1 | 9/2009 |
| WO | WO-2010/093627 A2 | 8/2010 |
| WO | WO-2010/131114 A2 | 11/2010 |

OTHER PUBLICATIONS

Heard and Weiner, A Regional Net Charge and Structural Compensation Model to Explain How Negatively Charged Amino Acids Can Be Accepted within a Mitochondrial Leader Sequence, The Journal of Biological Chemistry vol. 273, No. 45, Issue of Nov. 6, pp. 29389-29393, 1998 (Year: 1998).*
Barrientos et al., "The highly specific carbohydrate-binding protein cyanovirin-N: structure, anti-HIV/Ebola activity and possibilities for therapy," Mini Rev Med Chem. 5(1):21-31 (2005).
Christiansen et al., "The carbohydrate-binding module family 20—diversity, structure, and function," FEBS J. 276(18):5006-29 (2009).
Extended European Search Report for European Application No. 15834013.3, dated Dec. 8, 2017 (8 pages).
Machovic et al., "A new clan of CBM families based on bioinformatics of starch-binding domains from families CBM20 and CBM21," FEBS J. 272(21):5497-513 (2005).
International Search Report and Written Opinion for International Patent Application No. PCT/2015/46588, dated Dec. 7, 2015 (12 pages).
Gunnarsson et al. "Molecular engineering of a thermostable carbohydrate-binding module," Biocatal and Biotran. 24(1/2): 31-37 (2006).
Ficko-Blean et al. "N-Acetylglucosamine Recognition by a Family 32 Carbohydrate-Binding Module from Clostridium perfringens NagH," J. Mol. Biol. 2-14 (2009).
Smith et al. "Small Binding Proteins Selected from a Combinatorial Repetoire of Knottins Displayed on Phage," J. Mol. Biol. 2-17 (1998).
Lehtiö et al. "Alpha-Amylase Inhibitors Selected From a Combinatorial Library of a Cellulose Binding Domain Scaffold," Proteins. 2-8 (2000).

* cited by examiner

*Primary Examiner* — Thomas S Heard
(74) *Attorney, Agent, or Firm* — Clark & Elbing LLP

(57) ABSTRACT

In general, the invention features a novel CBM32-derived affinity scaffold. In certain embodiments, the scaffold comprises two types of regions: constant regions (CRs) and variable loop regions (VLRs) as depicted in the structure in FIG. 1. We have discovered that the CRs provide structural features that enable overall conformational stability while the intervening sequences corresponding to VLRs tolerate amino acid sequence randomization.

5 Claims, 15 Drawing Sheets

Specification includes a Sequence Listing.

FIG. 3

| Primer | Sequence (5'→3') |
|---|---|
| 397-TF | CGTTCTGAATCCTGGNNNNNNNNNNNNGGAATGAAGCCAATTATTAGATG |
| 398 R | CCAGGATTCAGAACGAATTAAAGAAG |
| 404 F | TCTCTTGCAGGAGAATTCATTGGATTG |
| 405A R | TTCCAGATTAGTCAGACGAATGTACTTAG |
| 402TR | TTCTCCTGCAAGAGANNNNNNNNNNNNNNNNNNNNATACCAAACACCGGTGTTATCGTC |
| 403TF | CTGACTAATCTGGAANNNNNNNNNNNNNNCTGACTTTAGTGAGTTTGCAATTG |
| 391 F | CATCATCATCATCACAACCCTCTTAATTCGTTCTGAATC |
| 450 R | GGCTTTGTTAGCAGTCAGCTCAGACACAATTGCAAACTCACTAAAAG |
| 390 R | GTGATGATGATGATGGCTGCCC |
| 387 F | GCTGCTAACAAAGCCCGAAAGGAAGCTG |

FIG. 7

| CBM/Protein | | Buffer |
|---|---|---|
| nCBM | 57.2 | 87.5 mM Citrate, 0.5 M NaCl, pH 5.5 |
| G834F | 60.5 | 87.5 mM Citrate, 0.5 M NaCl, pH 5.6 |
| K860P | 56 | 87.5 mM Citrate, 0.5 M NaCl, pH 5.7 |
| S815R | 55.5 | 87.5 mM Citrate, 0.5 M NaCl, pH 5.8 |
| E849D | 55.5 | 87.5 mM Citrate, 0.5 M NaCl, pH 5.9 |
| K922R | 59 | 87.5 mM Citrate, 0.5 M NaCl, pH 5.10 |
| G834F, K922R | 62.5 | 98 mM Citrate, 100 mM NaCl, pH 5.5 |
| G834F, K922R, S815R, E849D | 62 | 100 mM Citrate, 250 mM NaCl, 5 mM CaCl2, pH 5.5 |
| nCBM | 63.5 | 100 mM Citrate, 250 mM NaCl, 5 mM CaCl2, pH 5.5 |
| G834F | 65 | 100 mM Citrate, 250 mM NaCl, 5 mM CaCl2, pH 5.5 |
| K922R | 64 | 100 mM Citrate, 250 mM NaCl, 5 mM CaCl2, pH 5.5 |
| G834F, K922R, S815R, E849D | 62 | 100 mM Citrate, 250 mM NaCl, 5 mM CaCl2, pH 5.5 |
| G834F, K922R, F882Y | 64.5 | 100 mM Citrate, 250 mM NaCl, 5 mM CaCl2, pH 5.5 |
| G834F, K922R, L888K | 65 | 100 mM Citrate, 250 mM NaCl, 5 mM CaCl2, pH 5.5 |
| G834F, K922R, E891K | 65 | 100 mM Citrate, 250 mM NaCl, 5 mM CaCl2, pH 5.5 |
| G834F, K922R, V944R | 64.5 | 100 mM Citrate, 250 mM NaCl, 5 mM CaCl2, pH 5.5 |
| nCBM | 57 | 20 mM MOPS, 150 mM NaCl, pH 6.5 |
| K922R | 57 | 21 mM MOPS, 150 mM NaCl, pH 6.5 |
| G834F, K922R, V944R, M929K | 52 | 22 mM MOPS, 150 mM NaCl, pH 6.5 |
| G834F, K922R, V944R, M929L | 52 | 23 mM MOPS, 150 mM NaCl, pH 6.5 |
| G834F, K922R, V944R, M929R | 51 | 24 mM MOPS, 150 mM NaCl, pH 6.5 |
| K922R, V944R | 53 | 25 mM MOPS, 150 mM NaCl, pH 6.5 |
| K922R, M929K | 57 | 26 mM MOPS, 150 mM NaCl, pH 6.5 |
| K922R, M929L | 58 | 27 mM MOPS, 150 mM NaCl, pH 6.5 |
| K922R, M929R | 55 | 28 mM MOPS, 150 mM NaCl, pH 6.5 |

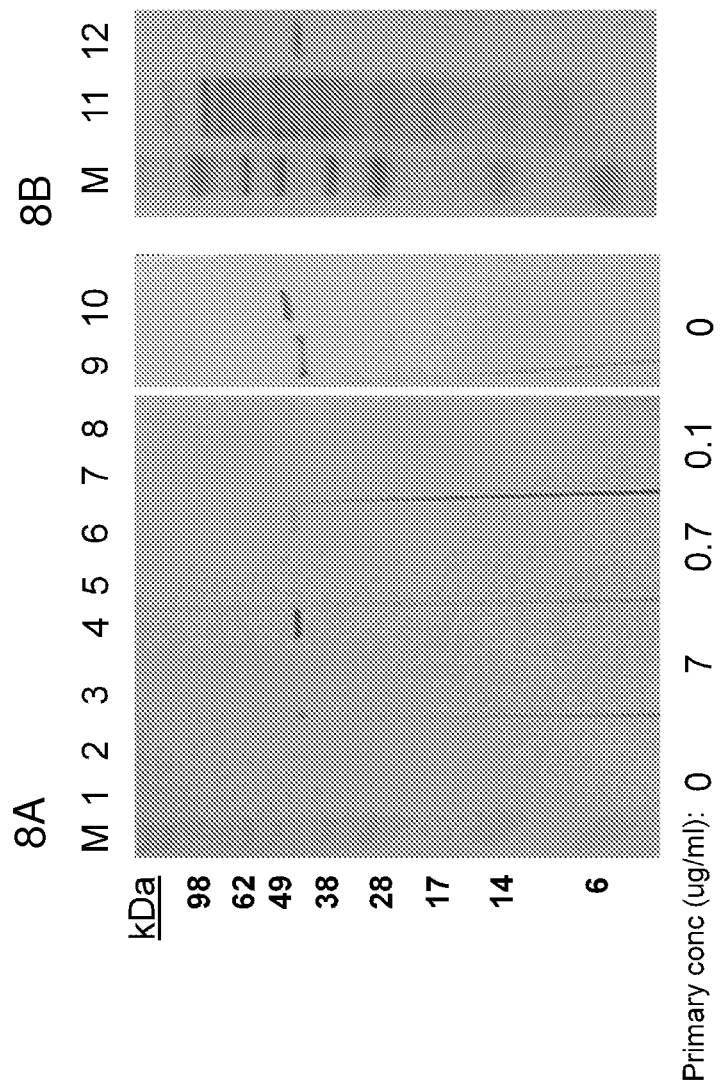

FIG. 13

| Primer | Sequence (5'-3') |
|---|---|
| 387 F | GCTGCTAACAAGCCCGAAAGGAAGCTG |
| 390 R | GTGATGATGATGATGATGGCTGCTGCCC |
| 390A R | AGAAGGGTTGTGATGATGATGATGGCTGCTGCC |
| 391 F | CATCATCATCACAACCCTCTTAATTCGTTCTGAATC |
| 391A F | CATCACACCCTCTTAATTCGTTCTGAATC |
| 392 R | GGCTTTGTTAGCAGCTCAGTCAGACACAATTGCAAACTCACTAAAAG |
| 397 F | CGTTCTGAATCCTGGNNNNNNNNNNNGGAATGAAGCCAATTATTAGATG |
| 398 R | CCAGGATTCAGAACGAATTAAAGAAG |
| 402T R | TTCTCCTGCAAGAGANNNNNNNNNNNNNNNNATACCAACACCGGTGTTATCGTC |
| 403T F | CTGACTAATCTGGAANNNNNNNNNNNNNNCTGACTTTTAGTGAGTTTGCAATTG |
| 404 F | TCTCTTGCAGGAGAATTCATTGGATG |
| 405A R | TTCCAGATTAGTCAGACGAATGTACTTAG |
| 450 R | GGCTTTGTTAGCAGCTCAGCAGTCAGACACAATTGCAAACTCACTAAAAG |
| 493 F | TGCAGCAGCCATCATCATCATCACAAC |
| 494 R | ATGATGGCTGCTGCACAGTGGTATATCTCCTTC |
| 507 R | ATGGCTGCAGCCCATGGTATATCTCCTTC |
| 508 F | ATGGGCTGCAGCCATCATCATCATCAC |
| 512T F | ACCGGTGTTTGGTATNNNNNNNNNNNNNNNNNNNNNNNTCTCTTGCA<br>GGAGAATCATTGGATTG |
| 517 F | GGCTAGTCCCAGGAGGGTGGTGGC |
| 518 R | CTCCTGGGACTAGCCGTCAGACACAATTGCAAACTCACTAAAAG |
| 523 R | ATACCAAACACCGGTGTTATCGTCTCCATC |
| 527 R | CCCTCCACCCGAGCCACCACCGGCTGCCACCTCCACCCGTCAGACACAATTGCAAACTCACTAAAAG |
| 540 F | GGCTCGGGTGGAGGGTGCTGAGCTGCTAACAAGCCCGAAAGGAAG |

# AFFINITY PROTEINS AND USES THEREOF

FIELD OF THE INVENTION

This invention is in the field of protein binding agents, in particular antibody substitutes based on the CBM32 protein.

BACKGROUND OF THE INVENTION

The adaptive immune system is a highly evolved, flexible system for the recognition and neutralization of foreign organisms and macromolecules. Adaptive immunity includes a vast variety of different similar structures that have been diversified by combinatorial assembly of varied building blocks with highly random linker segments. The two principle recognition complexes of the higher vertebrate adaptive immune system, antibodies and the T cell antigen receptor, are similarly assembled, and function through their cognate cell types, B cells and T cells, to effect a coordinated resistance to pathogens.

Antibodies have been exploited, e.g., in the fields of diagnostics, therapeutics, and research tools. However, due to their complexity, antibodies can be difficult to produce for a variety of applications. Thus, there exists a need in the art to develop substitute proteins that have antibody-like properties.

Carbohydrate-binding modules (CBMs) are found in carbohydrate-active enzymes and assist in mediating the adherence of the complete enzyme to carbohydrate substrates. Specifically, CBM family 32 is one of the more structurally diverse CBM families with a high affinity for galactose-based ligands. NagH, a hyaluronglucosaminidase, secreted by *Clostridium perfringens* contains four CBM32 modules that contain a beta-sandwich scaffold common to members of the CBM32 family. The second of the four modules has a unique specificity for N-acetylglucosamine.

SUMMARY OF THE INVENTION

In one aspect, the invention features an affinity scaffold, the affinity scaffold having the following formula:

CR1-V-CR2-W-CR3-Z-CR4, wherein:
the V, W, and Z are each independently not present or include one or more amino acids;
the constant regions CR1-CR4 have amino acid sequences that have at least 70% identity to SEQ ID NOs: 2, 4, 6, and 8, respectively; and
the affinity scaffold does not include the polypeptide of the amino acid sequence of SEQ ID NO: 1.

In another aspect, the invention features an affinity scaffold, the affinity scaffold having the following formula:

CR1-V-CR2-W-CR5-X-CR6-Y-CR7-Z-CR4, wherein:
the V, W, X, Y, and Z are each independently not present or include one or more amino acids;
the constant regions CR1, CR2, CR5, CR6, CR7, and CR4 have amino acid sequences that have at least 70% identity to SEQ ID NOs: 2, 4, 9, 11, 13, and 8, respectively; and
the affinity scaffold does not include the polypeptide of the amino acid sequence of SEQ ID NO: 1.

The affinity scaffold as described herein, wherein if the V, W, and Z are amino acids having SEQ ID NOs: 14-16, respectively, the affinity scaffold would specifically bind a maltose binding protein (MBP) molecule.

In any of the preceding aspects, CR1-CR7 have amino acid sequences that have at least 80% (e.g., 90%, 95%, 99%, or 100%) identity to SEQ ID NOs: 2, 4, 6, 8, 9, 11, and 13, respectively. For example, constant regions CR1-CR7 include at least one amino acid residue substitution mutation (e.g., 2 or more, 3 or more, 4 or more, 5 or more, 6 or more, 7 or more, 8 or more, 9 or more, or 10 substitution mutations), wherein the substitution mutation is selected from the group consisting of S815R, G834F, E849D, K860P, F882Y, L888K, E891K, K922R, M929K, M929L, M929R, and/or V944R. In certain preferred embodiments, the CRs contain the substitution mutation M929L.

A protein, including the affinity scaffold as described herein, wherein the protein includes an amino acid sequence that is at least 80% identity to the amino acid sequence of SEQ ID NO: 1.

In another aspect, the invention features a protein (e.g., a protein that specifically binds to a target molecule) including any of the foregoing affinity scaffolds. In certain embodiments, the protein can have an amino acid sequence that has at least 90% (e.g., 95%, or 99%) identity to the amino acid sequence of SEQ ID NO: 1. The protein can be, e.g., a monomer or multimer.

Also in any of the foregoing aspect, the V, W, X, Y, and Z may include amino acids having less than 100% sequence identity (e.g., less than 70%, 40%, 20% identity) to the amino acid sequences of SEQ ID NOs: 3, 5, 10, 12, and 7, respectively. The V, W, X, Y, and Z may include four or more (e.g., five) amino acids. The V, W, X, Y, and Z may independently or in combination contribute to the specific binding of the protein to the target molecule.

Any of the foregoing proteins can include a polypeptide (e.g., an enzyme, a polypeptide that promotes multimerization, or a substrate for an enzyme) fused to the N-terminus of CR1 and/or the C-terminus of the CR4. The protein can, e.g., be fused to a tag (e.g., selected from the following: Cysteine (Cys), poly-histidine (poly-His), and an epitope tag). Additionally, or alternatively, the protein can be, e.g., conjugated to one or more functional groups (e.g., cysteine, biotin, a fluorescent dye, an enzyme, a radioactive functional group, a lanthanide, streptavidin derivative, a peptide that promotes multimerization (e.g., a right handed coiled-coil (RHCC) peptide of an archaebacterium, a COMPcc from human cartilage oligomeric matrix protein, a C4bpalpha derived from human plasma C4 binding protein, and heptamerization domain of the Archaeal RNA binding protein Sm1). The protein can also be, e.g., pegylated, polyol responsive, or immobilized to a solid support. Furthermore, the protein can further include a peptide linker attaching one or more of the CRs1-7 to one or more of V, W, X, Y, and/or Z. In another aspect the invention features an isolated cDNA sequence encoding any of the foregoing affinity scaffolds or proteins, e.g., in an expression-conducive context.

In another aspect, the invention features a method of identifying one of the foregoing proteins, the method including the steps of:
generating a protein as described herein from a polypeptide display library wherein the library is generated from randomization of regions of an isolated cDNA sequence encoding for V, W, X, Y, and/or Z, corresponding to SEQ ID NOs: 3, 5, 10, 12, and 7, respectively;
contacting the target molecule with the protein; and
assaying specific binding of the protein to the target molecule.

By "affinity scaffold" is meant a non-immunoglobulin polypeptide framework, e.g., derived from the amino acid sequence of CBM32 (SEQ ID NO: 1). The term "affinity scaffold" includes polypeptides having variable loop regions (VLRs) that are found to confer specific binding properties to the affinity scaffold, polypeptides containing VLRs for which a specific binding property has not been identified, or is not present, and polypeptides lacking VLRs.

The term "constant regions (CRs)," are polypeptide regions of the affinity scaffolds which contain amino acid residues that provide a framework structure for the scaffold. CRs can be, e.g., fixed in the scaffold, restricting the polypeptide sequence in these regions as they contribute to the overall stability of the scaffold.

By "variable loop regions (VLRs)" is meant regions that can optionally be present in an affinity scaffold, interspersed between CRs. The VLRs can, e.g., individually, or in combination, confer binding specificity between a protein including an affinity scaffold and a particular target molecule. Each of the VLRs can include, independently, amino acid substitutions of the corresponding sequence of the CBM32 protein (e.g., the protein of SEQ ID NO: 1), deletions of amino acids of the corresponding sequence of the CBM32 protein, and/or insertions of one or more amino acids. Accordingly, VLRs can vary in length and share low percent amino acid sequence identity relative to the corresponding region of the CBM32 protein.

The term "percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, for a reference polypeptide of sequence A, when compared to the derivative polypeptide of sequence B, the percent amino acid sequence identity is calculated as:

100 times the fraction X/Y, where X is the number of amino acid sequence residues scored as identical matches between A and B, and where Y is the total number of amino acid residues in the polypeptide sequence of B.

The term "amino acid" refers to a residue in a polypeptide sequence that can be naturally occurring or synthetic. A naturally occurring amino acid is one encoded by the genetic code, as well as those that are later modified, e.g., biotinylated-cysteine. A synthetic amino acid is one that is analogous in chemical structure to a naturally occurring amino acid; or one that has a different chemical structure from a naturally occurring amino acid yet functions similarly to a naturally occurring amino acid. Amino acids may be referred to herein by their single or three letter abbreviations. The single letter abbreviation for a particular amino acid, its corresponding amino acid, and three letter abbreviation are as follows: A, alanine (Ala); C, cysteine (Cys); D, aspartic acid (Asp); E, glutamic acid (Glu); F, phenylalanine (Phe); G, glycine (Gly); H, histidine (His); I, isoleucine (Ile); K, lysine (Lys); L, leucine (Leu); M, methionine (Met); N, asparagine (Asn); P, proline (Pro); Q, glutamine (Gln); R, arginine (Arg); S, serine (Ser); T, threonine (Thr); V, valine (Val); W, tryptophan (Trp); and Y, tyrosine (Tyr).

A "polypeptide" refers to polymers of amino acids of any length. As used herein, a polypeptide sequence refers to the amino acids conjugated by a peptide bond or non-peptide bond to form the polypeptide in reference.

By a "reference polypeptide" is meant a protein that is identical in sequence, except for the introduced-amino acid modifications.

The term "randomized" refers to one or more amino acid modifications relative to a template sequence. Randomization may be accomplished through directed or spontaneous sequence variation, generally of a nucleic acid coding sequence. Randomization can include amino acid substitutions, deletions, or insertions.

The term "specifically binds" or "specific binding," when referring to a polypeptide or protein, refers to a binding reaction that is determinative of the presence of a target molecule, oftentimes when the target molecule is in a population of molecules. This can be detected by an immunoassay, as referred to herein, in which a specified scaffold binds a particular target molecule at least 2 fold more selectively than the background, resulting in a dissociation constant no greater than 100 µM. Specific binding to a target molecule requires selection for specificity between the contacting amino acids of a target molecule with the VLRs and possibly CRs of the scaffold protein. For example, a scaffold that specifically binds a maltose binding protein (MBP) can be selected as described in Example 1 below, where an immunoassay consisting of an ELISA is performed with a candidate scaffold protein and a MBP to calculate the binding affinity between the target molecule and the scaffold protein, where the cutoff for high affinity is a dissociation constant no greater than 500 nM.

The term "substitution mutation" refers to a modification of any one of the amino acids in the sequence given for the reference polypeptide in SEQ ID NO: 1, where an alteration to the code leads to a change in the resulting protein, e.g., the folding, thermostability, and/or target interactions.

The term "polyol responsive" refers to the binding properties of a protein when in contact with an elution buffer comprising low molecular weight polyhydroxylated compounds. In particular, a "polyol responsive" protein exhibits decreased binding properties in the presence of an elution buffer comprising low molecular weight polyhydroxylated compounds usually in the presence of ammonium sulfate.

The term "tag" refers to an addition of an amino acid sequence, detectable label, or other molecule to the CBM32 derivative protein that enables isolation, multimerization, purification, or detection of said CBM32 derivative.

A "host cell" includes an individual cell or cell culture which can be or has been a recipient for the subject vectors. Host cells include progeny of a single, e.g., parental, host cell. The progeny may not necessarily be completely identical (in morphology or in genome of total DNA complement) to the original parent cell due to natural, accidental, or deliberate mutation. An example of a host cell described herein is *E. coli*.

BRIEF DESCRIPTION OF THE DRAWINGS

FIG. 3 is a table containing the primer name and sequences used to construct the VLRs of the CBM affinity scaffold of library 2.

FIG. 5A displays seven lanes, where lane 1 is a molecular weight marker; lane 2 is total protein lysate from E. coli; lane 3 is total protein lysate from E. coli spiked with MBP (0.018 mg/ml); and lanes 4-7 are serial column washes with EDTA. FIG. 5B displays seven lanes, where lane 8 is total protein lysate from E. coli spiked with MBP (0.018 mg/ml); lane 9 is a molecular weight marker; and lanes 10-14 are serial column elutions with polyol elution buffer.

FIG. 7 is a table summarizing the thermal shift assay (TSA) analysis of protein scaffold CBM (PDB 2W1Q), residues 807-946, and various mutants.

FIGS. 8A and 8B are images of a protein membrane and polyacrylamide gel displaying the results of specific binding between a library 1 derived CBM scaffold protein targeting MBP with the resulting detection of MBP by immunoblot in panel A and the total protein stain in panel B. In panels A and B, lane M contains a molecular weight marker; lanes 1, 3, 5, 7, 9, and 11 contain 7 μg of E. coli whole cell protein lysate; and lanes 2, 4, 6, 8, 10, and 12 contain 100 ng of recombinant maltose binding protein. Panel A displays a PVDF membrane onto which total electrophoresed protein was transferred, stained with an MBP specific 6His-CBM, and subsequently stained with anti-6His-HRP (lanes 1-8), or an anti-MBP-HRP as a positive control (lanes 9 and 10). The primary concentration of the CBM used to probe the protein is provided along the bottom of the image, ranging from 0-7 μg/ml. Panel B displays the polyacrylamide gel on which the total protein lysates and recombinant MBP were separated prior to blotting onto the PVDF membrane of panel A.

FIG. 13 is a table showing primers used to construct CBM phage libraries (e.g., libraries 2 and 3) in pComb3X and expression constructs in pET15b. NNN=mix of 18 phosphoramidite trimers excluding Cys, Met, and Stop codons.

DETAILED DESCRIPTION OF THE INVENTION

Figure 1:
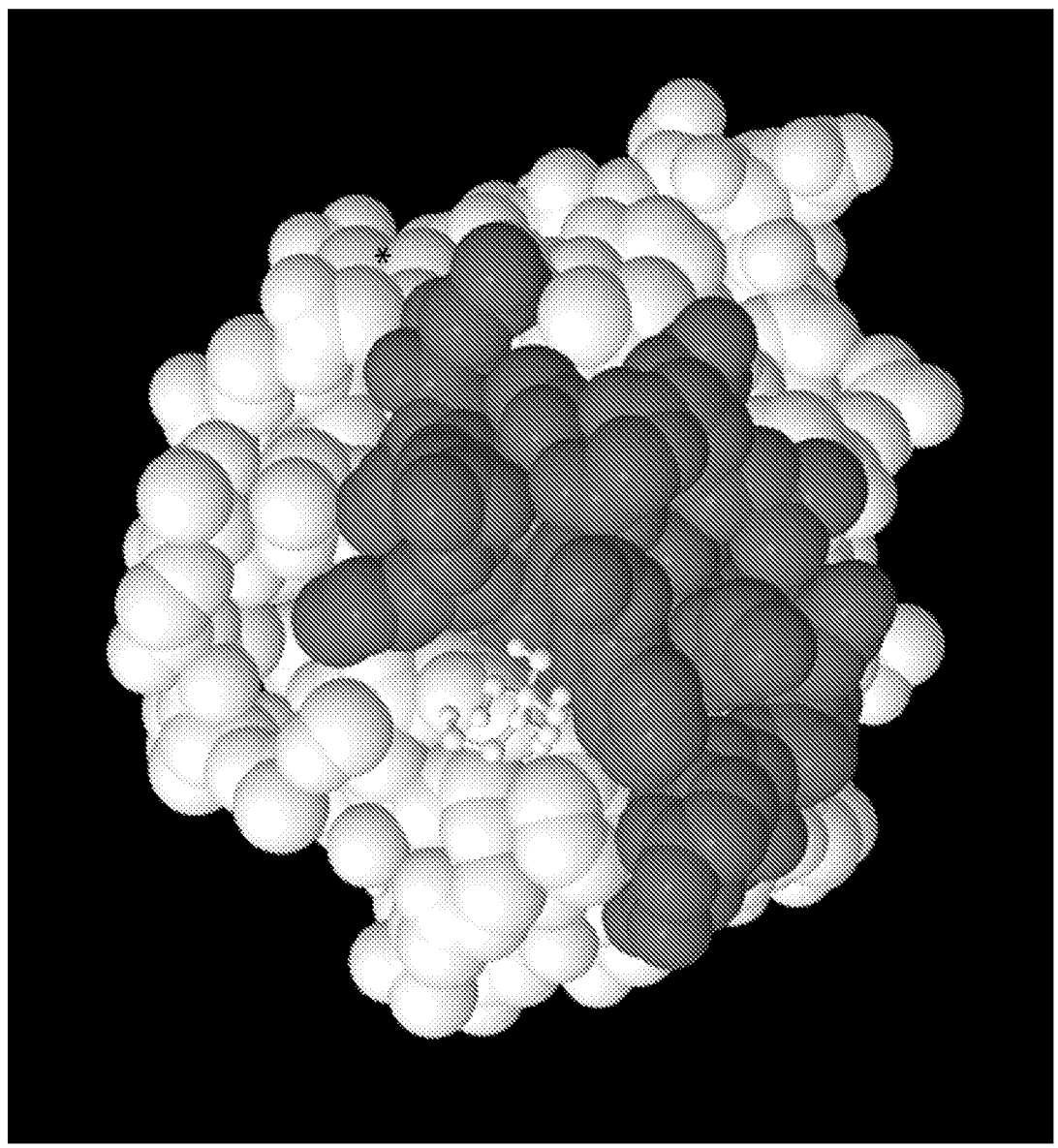
FIG. 1 is an image of the structure of the CBM protein, where the CRs are in white, the VLRs are shaded, and the substituted Met is starred.

The invention features a novel CBM32-derived affinity scaffold. In certain embodiments, the scaffold comprises two types of regions: constant regions (CRs) and variable loop regions (VLRs), e.g., as depicted in the structure in FIG. 1. Because the naturally occurring CBM32 family engages a diverse range of targets with high specificity, we found it to be an ideal candidate for an affinity scaffold structure. We have discovered that the CRs provide structural features that enable overall conformational stability while the intervening sequences corresponding to VLRs tolerate amino acid sequence randomization. The VLRs can thus be modified to provide the affinity scaffold protein with specific binding properties for a desired target molecule, which allows for binding of what were previously challenging target molecules. The affinity scaffold protein is small, typically lacks cysteines, and can be modified to remove easily oxidized, sulfur-containing amino acids; these properties render the affinity scaffold protein advantageous over traditionally used antibodies for similar applications. Furthermore, in certain embodiments, the affinity scaffold protein shows polyol-responsive binding to its target molecules, which enables the gentle elution of target molecule(s) without disrupting potential target-target interactions and target activity.

The CBM32 protein has a molecular weight (MW) of approximately 15.6 kDa, which is approximately 10 times smaller than an immunoglobulin, making it advantageous over antibodies. The wild type protein lacks cysteines, which we have found provides the additional advantage of not containing easily oxidized, sulfur-containing amino acids. CBM32 consists of a beta-like strand; a loop; a beta-like strand; a loop; a beta-like strand; a loop; a beta-like strand; a loop; a beta-like strand; a loop; a beta-like strand; a loop; and a beta-like strand. In certain embodiments, the overall structure of beta-like strands is maintained regardless of the presence of CR mutations. The loop regions tolerate sequence variability that enables substitutions to the sequence. Additionally, the length of the loop regions can be modified to enable insertions or deletions of amino acid residues that confer additional binding properties to a diversity of targets. Similar to complementarity determining regions (CDRs) in immunoglobulins, these loop regions confer target binding specificity.

The CRs of the affinity scaffold provide the structural framework for the scaffold, including thermostability. The invention provides for as few as four or as many as six CRs, depending on the number of VLRs desired. Interspersed between the CRs are loop regions, the VLRs, which have a high tolerance for diversification of amino acid sequence and length. The invention includes an affinity scaffold that comprises one, two, three, four, or five VLRs that singly or in combination can provide the desired specificity to a target molecule depending on the binding properties of the amino acid residues within these regions. Suitable VLRs for a specified target molecule can be identified by screening a library having various combinations of VLRs against a target molecule of interest. In certain embodiments, a candidate affinity scaffold identified by such a screening can be further optimized through a second (or third, or more) round of variabilization and screening.

The affinity scaffold can vary in number and length of CRs, depending on the VLRs selected for a particular affinity scaffold. In some instances, the affinity scaffold includes CRs selected from CRs 1-7 and VLRs selected from V-Z. As referenced here, the full length wild type CBM protein, from which the affinity scaffold is derived, includes the amino acid sequence listed below, hereinafter referred to as SEQ ID NO: 1:

NPSLIRSESWQVYEGNEANLLDGDDNTGVWYKTLNGDTSLAGEFIGLDLG

KEIKLDGIRFVIGKNGGGSSDKWNKFKLEYSLDNESWTTIKEYDKTGAPA

GKDVIEESFETPISAKYIRLTNMENINKWLTFSEFAIVSD

In one embodiment, the affinity scaffold includes four CRs (CR1-CR4) and three VLRs (V, W, and Z), represented by the formula:

CR1-V-CR2-W-CR3-Z-CR4, where CR1-CR4 correspond to the sequences of SEQ ID NOs: 2, 4, 6, and 8, respectively; and V, W, and Z correspond to SEQ ID NOs: 3, 5, and 7, respectively, as depicted below.

SEQ ID NO: 2:
NPSLIRSESW

SEQ ID NO: 3:
QVYE

SEQ ID NO: 4:
GNEANLLDGDDNTGVWY

SEQ ID NO: 5:
KTLNGDT

SEQ ID NO: 6:
SLAGEFIGLDLGKEIKLDGIRFVIGKNGGGSSDKWNKFKLEYSLDNES

WTTIKEYDKTGAPAGKDVIEESFETPISAKYIRLTNME

SEQ ID NO: 7:
NINKW

SEQ ID NO: 8:
LTFSEFAIVSD

In a second embodiment, the affinity scaffold comprises six CRs (CR1, CR2, and CR4-CR7) and five VLRs (V, W, X, Y, and Z), represented by the formula:

CR1-V-CR2-W-CR5-X-CR6-Y-CR7-Z-CR4, where CR1, CR2, CR5, CR6, CR7, and CR4 correspond to the amino acid sequences of SEQ ID NOs: 2, 4, 9, 11, 13, and 8, respectively; and V, W, X, Y, and Z, correspond to the amino acid sequences of SEQ ID NOs: 3, 5, 10, 12, and 7, respectively, as given below.

SEQ ID NO: 2: NPSLIRSESW

SEQ ID NO: 3: QVYE

SEQ ID NO: 4: GNEANLLDGDDNTGVWY

SEQ ID NO: 5: KTLNGDT

SEQ ID NO: 7: NINKW

SEQ ID NO: 8: LTFSEFAIVSD

SEQ ID NO: 9: SLAGEFIGLDLGKEIKLDGIRFVIGKN

SEQ ID NO: 10: GGGSSDK

SEQ ID NO: 11: WNKFKLEYSLDNESWTTIKEYDK

SEQ ID NO: 12: TGAPAG

SEQ ID NO: 13: KDVIEESFETPISAKYIRLTNME

In some instances, if present, CRs 1-7 comprise amino acid sequences that have at least 80% (e.g., 85%, 90%, 95%, or 99%) identity to the amino acid sequence of SEQ ID NOs: 2, 4, 6, 8, 9, 11, and 13, respectively. In some instances, CRs 1-7 comprise amino acid sequences that have at least 90% (e.g., 91%, 92%, 93%, 94%, 95%, 96%, 97%, 98%, or 99%) identity to the amino acid sequence of SEQ ID NOs: 2, 4, 6, 8, 9, 11, and 13, respectively. In some instances, CRs 1-7 comprise amino acid sequences that have at least 95% identity to the amino acid sequence of SEQ ID NOs: 2, 4, 6, 8, 9, 11, and 13, respectively. In some instances, CRs 1-7 comprise amino acid sequences that have at least 99% identity to the amino acid sequence of SEQ ID NOs: 2, 4, 6, 8, 9, 11, and 13, respectively. As a default, gaps in identity are ignored in calculating the sequence identity; however, the invention includes embodiments of the above sequence where gaps are treated as mismatches when calculating sequence identity.

In another example, CR2 can vary in length depending on the selection of the sequence corresponding to SEQ ID NO: 1 which is substituted and/or randomized in VLR V. When V is as long as 4 amino acid residues, CR2 can be as short as 17 amino acid residues and include the amino acid sequence "GNEANLLDGDDNTGVWY." When V is as short as 1 amino acid residue, CR2 can be as long as 21 amino acid residues and include the amino acid sequence "VYEGNEANLLDGDDNTGVWYK." In certain embodiments, the region of SEQ ID NO: 1 that is substituted in V can be 1, 2, 3, or 4, amino acids.

The VLRs of the affinity scaffold may also vary in number, length, and sequence. In one embodiment, the affinity scaffold protein includes one or more VLRs selected from V-Z, e.g., 1, 2, 3, 4, or all five of VLRs V-Z. In certain embodiments, the proteins of the invention include VLRs selected from V, W, and Z having amino acid sequences of SEQ ID NOs: 3, 5, and 7, respectively. In another embodiment, the affinity scaffold protein includes as many as five VLRs selected from V, W, X, Y, and Z having the amino acid sequences of SEQ ID NOs: 3, 5, 10, 12, and 7, respectively.

In some instances, VLRs one or more of V-Z comprises amino acid sequences that have less than 100% (e.g., 95%, 90%, 85%, 80%, 75%, or 70%) identity to the amino acid sequence of SEQ ID NOs: 3, 5, 10, 12, and 7, respectively. In some instances, one or more of VLRs V-Z includes amino acid sequences have at most 70% (e.g., 65%, 60%, 55%, 50%, 45%, or 40%) identity to the amino acid sequence of SEQ ID NOs: 3, 5, 10, 12, and 7, respectively. In some instances, one or more of VLRs V-Z includes amino acid sequences have at most 40% (e.g., 35%, 30%, 25%, or 20%) identity to the amino acid sequence of SEQ ID NOs: 3, 5, 10, 12, and 7, respectively. In some instances, one or more of VLRs V-Z includes amino acid sequences have at most 20% (e.g., 15%, 10%, 5%, or 1%) identity to the amino acid sequence of SEQ ID NOs: 3, 5, 10, 12, and 7, respectively.

As an example, VLR V can vary in sequence and in length. In some embodiments, the affinity scaffold protein includes VLR V including an amino acid as short as one amino acid. In a second embodiment, the affinity scaffold protein specifically binds to the maltose binding protein (MBP) as a result of the VLRs V, W, and Z, including the amino acid sequences of SEQ ID NOs: 14, 15, and 16, respectively, as given below.

```
SEQ ID NO: 14: QLNN
SEQ ID NO: 15: VANVGTQ
SEQ ID NO: 16: TSGWG
```

In some instances, the affinity scaffold protein includes one, two, three, four, or five of any of the VLRs V-Z including amino acid sequences that confer specificity of the protein to a desired target molecule. The boundaries of the length of the VLRs V-Z are flexible and allow for modification of the length of amino acid residues, where some embodiments include VLRs of five or more amino acids.

In some embodiments, the affinity scaffold protein includes one or more substitution mutations in a CR that can, e.g., enhance or preserve thermostability and/or solubility. As referenced by the amino acid sequence of SEQ ID NO: 1, the affinity scaffold protein can include one or more substitution mutations selected from the following group: S815R, G834F, E849D, K860P, F882Y, L888K, E891K, K922R, M929K, M929L, M929R, and/or V944R (e.g., 2, 3, 4, 5, 6, 7, 8, 9, or 10 mutations). In certain preferred embodiments, the affinity scaffold protein includes the substitution mutation M929L, as referenced by the amino acid sequence of SEQ ID NO: 1, wherein the substitution mutation M929L removes an easily oxidized, sulfur-containing amino acid residue. In some embodiments, the affinity scaffold protein includes the substitution mutation M929L, as referenced by the amino acid sequence of SEQ ID NO: 1, and one or more substitution mutations selected from the following group: S815R, G834F, E849D, K860P, F882Y, L888K, E891K, K922R, and/or V944R (e.g., 2, 3, 4, 5, 6, 7, 8, 9, or 9 mutations).

In addition to or in the alternative to the mutations listed above, the CRs can have one or more additional mutations (e.g., conserved mutations). In certain embodiments, the affinity scaffold protein will retain its stability despite the presence of the above mutations. This stability can be determined by inserting into a scaffold containing these mutations VLRs known to confer binding of the non-mutated affinity scaffold protein to a particular target molecule, e.g., MBP, followed by testing whether these VLRs retain binding of the mutated affinity scaffold protein with the target molecule. For example, the VLRs set forth in SEQ ID NOs: 14-16 could be included in a mutated affinity scaffold protein to determine if MBP binding is retained.

In some embodiments, the affinity scaffold protein binds MBP. In one embodiment, the affinity scaffold protein includes four CRs and three VLRs, as referenced by any one of the three proteins of SEQ ID NOs: 17-19, capable of conferring binding to MBP. In a second embodiment, the affinity scaffold protein includes six CRs and five VLRs, as referenced by any one of the three proteins of SEQ ID NOs: 20-22, capable of conferring binding to MBP.

In some aspects, the affinity scaffold protein displays polyol responsiveness. In this aspect, the affinity scaffold protein possesses unique binding properties that allow for gentle purification of the protein bound to the target molecule(s) singly or in a complex. This feature provides the advantage of isolating the target molecule(s) without disrupting the target molecule(s) binding properties to other molecules. In this aspect, the protein, when bound to a target molecule(s) in the presence of an elution buffer including low molecular weight polyhydroxylated compounds, exhibits decreased binding properties to the target molecule(s). As a result, the protein's affinity for the target(s) decreases, allowing for elution of the specifically bound target(s). Methods of determining polyol sensitivity are described in the examples below.

Epitopes

In certain embodiments, the proteins of the invention may bind (e.g., specifically bind) a particular epitope. Such epitopes can include therapeutic targets, diagnostic markers, or other molecules, including proteins, carbohydrates, nucleic acids, etc. Examples of such epitopes include those proteins set forth below:

Biotin Carboxyl Carrier Protein (BCCP)
Glutathione-S-Transferase (GST)
Green Fluorescent Protein (GFP)
Maltose Binding Protein (MBP)
Nus-tag (NusA protein)
Thioredoxin (Trx)
Fc-tag (Immunogloblin Fc domain)
rabbit IgG
mouse IgG
goat IgG
rat IgG
bovine IgG
dog IgG
Carbohydrate binding module (CBM)
2W1Q
Yellow fluorescent protein
mCherry
beta-galactosidase
Digoxigenin
Biotin
Small Ubiquitin-like Modifier (SUMO)

CBM 4A41

Other epitopes include protein tags, e.g., those listed in Table 1 below:

TABLE 1

| | |
|---|---|
| AviTag | GLNDIFEAQKIEWHE |
| Calmodulin-tag | KRRWKKNFIAVSAANRFKKISSSGAL |
| Polyglutamate tag | EEEEEE |
| E-tag | GAPVPYPDPLEPR |
| Flag-tag | DYKDDDDK |
| HA-tag | YPYDVPDYA |
| His-tag | HHHHHH |
| Myc-tag | EQKLISEEDL |
| S-tag | KETAAAKFERQHMDS |
| SBP-tag | MDEKTTGWRGGHVVEGLAGELEQLRARLEHHPQGQREP |
| Softag 1 | SLAELLNAGLGGS |
| Softag 3 | TQDPSRVG |
| Strep-tag | WSHPQFEK |
| TC-tag | CCPGCC |
| V5 tag | GKPIPNPLLGLDST |
| VSV-tag | YTDIEMNRLGK |
| Xpress tag | DLYDDDDK |
| Isopeptag | TDKDMTITFTNKKDAE |
| Spy Tag | AHIVMVDAYKPTK |

Multimerizeration Domains

In certain embodiments, the proteins of the invention include polypeptides that promote multimerization. Such polypeptide domains are described in Wang et al., (Protein Engineering, Design and Selection (2013) 26 (6): 417-423), Kim et al., (Plos One, (2012) 7: 1-13), and Walper et al. (J Immunol Methods (2013) 388(1-2):68-77), which are herein incorporated by reference in their entirety. Examples of such domains include RHCC derived from a right-handed coiled-coil peptide of an archaebacterium, the heptamerization domain of the Archaeal RNA binding protein Sm1, a streptavidin derivative, COMPcc from human cartilage oligomeric matrix protein, and C4bpa derived from human plasma C4-binding protein α-chain. Such domains can be N-terminal or C-terminal fusions or be inserted into the proteins of the invention (e.g., within a sequence corresponding to a VLR). Alternatively, such peptide domains can be covalently attached to a protein of the invention, e.g., via a thioether bond using an N- or C-terminal cysteine.

Construction of Libraries and Designed Variants

Libraries of the proteins of the invention (e.g., proteins including the affinity scaffolds of the invention) can be constructed as described in Examples 1, 2, and 5 below. Additionally, libraries of proteins including the affinity scaffold of the invention can be prepared in various ways known to those skilled in the art. Disseminated random substitution, clustered substitution, and designed (targeted) alteration are strategies that have been employed to increase the affinity of a given diversified scaffold for a particular target protein. In general, the objective of such diversification is to increase affinity without compromising the overall stability or solubility of the protein. One of the most widely employed strategies is surface randomization, the replacement of endogenous sequences on one particular aspect or face of a protein in order to generate a highly diverse collection of surfaces. Two common subtypes of surface randomization are loop and pocket diversification, used for proteins that are naturally convex or concave respectively. Randomizations may conserve or alter length if the scaffold is appropriately stable. In addition, the natural geometry of the scaffold may be altered by incorporation of structural elements that endow the randomized or grafted sequences with particular folds or shapes. Among the known elements that may be employed for such purposes are the placement of cysteine residues such that a disulfide-linked loop is formed, the introduction of helix or sheet-destabilizing residues, such as glycine or proline, the incorporation of beta turns or Trp cage motifs, or the formation of additional secondary structure elements, such as short alpha helical or beta strand sequences.

The proteins of the invention can be further adapted to include diverse polypeptides sequences at their amino or carboxyl termini. The additional diversity may enhance affinity by providing secondary binding sites to the target, or may enhance the functional properties of the protein by binding to proteins with enhanced plasma half-life, or proteins that are known to be enriched in the vicinity of the target, or that afford the possibility of concentration in an organ or tissue-specific manner by binding to organ or tissue-specific secondary targets. The additional diversity may also enhance detection of binding events involving the affinity scaffold protein by including enzymatic activity, fluorescence, or color.

The identification of high-affinity, high-selectivity proteins of the invention can be achieved by either screening methods or selection methods. A screening method typically requires two elements: a supply of candidate proteins of the invention to be tested for affinity to the target; and a systematic method for the enumeration of the candidates, such as an ordered array or systematically composed mixture that can be deconvolved to reveal the identity of the most active variants. Screening methods often require that large numbers of proteins of the invention be evaluated; in such cases it is common to use pooling schemes to mix candidates, allowing the presence or absence of a desired candidate to be determined with fewer measurements. Active pools are further subdivided to identify active unique species. Candidates derived from such screens can be subjected to further randomization and screening to progressively derive proteins of the invention of higher binding affinity.

Selection methods typically require a library of candidate proteins of the invention, each prepared in a form that provides a genetic linkage between the protein and a nucleic acid that encodes or identifies the protein. A mechanism must be provided to physically isolate and purify candidate binding proteins and their associated nucleic acids from the remaining library members that lack activity. In selection methods many fewer measurements are typically performed than in screening methods.

The present invention further provides methods for the identification of proteins of the invention having favorable affinity, selectivity, solubility, and thermostability. Numerous selection methods for the enrichment of nucleic acids encoding proteins of interest that bind to a specific target are known in the art and are useful for the generation of the desired proteins of the invention. Among these are the so-called display technologies, including phage display, yeast display, bacterial display, viral display, mammalian cell display, ribosome display, RNA display and DNA display. For the application of a particular form of display, an appropriate vector must be provided that is suitable for the display of the proteins of the invention in the context in which selection is to take place. For example for commonly practiced forms of bacteriophage display, a plasmid encoding a translational fusion between a solvent-exposed phage structural protein and the proteins of the invention must be created. For cellular display, such as bacterial, yeast or mammalian cell display, a fusion or stable association is created between a surface protein and the proteins of the invention. For ribosome or mRNA display, a fusion or stable association must be created between the diversified binding protein and the mRNA that encodes it. For DNA display a fusion or stable association must be created between the proteins of the invention and a high affinity, typically site-selective, DNA-binding protein. For some types of selection method, physical association of the binding protein and the nucleic acid that encodes it is provided by physical compartmentalization. For example, in emulsion selection methods, a small aqueous droplet is provided in which the proteins of the invention is synthesized from a template nucleic acid. In this case, the physical association is provided by the compartmentalization afforded by the nonaqueous phase that separates the individual droplets.

Display-based selections consist of one or more cycles of enrichment, each of which includes: (i) contacting the target molecule of interest with a mixture of diversified proteins in display context, e.g. as phage particles, cells, or RNA fusions; (ii) physically separating those phage particles, cells or RNA fusions that bind the target molecule from those that do not bind the target molecule, or bind less avidly, and (iii) amplifying the resulting isolated binding population by in vivo or in vitro methods to generate a new, enriched collection of diversified affinity scaffold proteins that can be subjected to additional rounds of contact and purification. For display-based selections, it is a requirement that the target molecule permit physical isolation of the complex of target molecule with the affinity scaffold proteins of the invention. For example the target molecule may be labeled with an antibody domain, peptide tag (e.g., a tag of Table 1), fluorophore, biotin, or other affinity or labeling moiety, allowing the complex of the proteins of the invention and target molecule to be physically separated from proteins of the invention that do not interact with the target molecule. Alternatively antibodies or binding reagents specific for the target molecule can be employed to effect separation. Often it is necessary to exclude unwanted proteins of the invention, for example those that bind to extraneous portions of the target molecule or to components of the apparatus used to effect physical separation. Common separation strategies rely upon an affinity matrix for the antibody domain, peptide tag, biotin, epitope or affinity moiety, such as a bead or magnetic particle bearing the cognate binding element for such antibody domain, tag, biotin, epitope or affinity moiety. Examples of commonly encountered binding elements include protein A, streptavidin, monoclonal or polyclonal antibodies, and coordinated transition metal divalent cations. Alternatively, separations based on fluorescence detection and sorting can be used. Such separations typically distinguish the signal conveyed by a fluorescent moiety or fluorophore attached to the target molecule, and permit the identification and selective separation of cells or particles bearing high concentrations of the target molecule by fluorescence-activated cell sorting. The contributions of undesired proteins of the invention can be reduced by preabsorption steps that mimic target molecule exposure and enrichment, but are conducted in the absence of target molecule.

Affinity

Selections or screens for proteins of the invention having the desired binding can be carried out by the methods described above followed by methods to identify candidate proteins of the inventions of particular interest according to their affinity, activity, selectivity, solubility, or thermostability. Many methods for the measurement of affinity are known in the art and include solid phase as well as solution phase measurements of association constant or reaction on and off rates for combination of the proteins of the invention with a target molecule. From the analysis of such equilibrium or kinetic constants the affinity of the proteins of the invention for its target molecule can be measured. Some methods of measuring affinity include, solid phase assays, such as planar or bead format assays, solution phase assays, or cell-based assays. Detection in such assays can be based on the analysis of changes in a signal generated by a detectably labeled target molecules or proteins of the invention, such as a radiolabeled target molecules or proteins of the invention or target molecules or proteins of the invention conjugated to or associated with an enzymatic activity or a fluorophore or fluorescent protein, or an active prosthetic group that behaves as a catalyst for a reaction or a change in property that is easily monitored. Common methods for measuring affinity include radiolabel or enzyme-linked immunosorbent assays, or assays based on surface plasmon resonance, fluorescence resonance, fluorescence polarization, or fluorescence autocorrelation spectroscopy or microscopy. A common form of affinity measurement is one in which a target molecule is immobilized on the solid phase, and varying concentrations of a solution containing a detectable form of the proteins of the invention is contacted with the immobilized target molecule to measure the amount of proteins of the invention bound as a function of concentration of proteins of the invention.

Selectivity

Proteins of the invention may bind to single members of families of target molecules, or multiple members of families of target molecules, to achieve the desired therapeutic, analytical, manufacturing, or research utility. For example, the neutralization of biological activity for therapeutic purposes may optimally require the antagonism of more than one target molecule, or the quantification of such biological activity for analytical purposes may require the recognition of more than one target molecule, or the purification of some target molecules of interest may require the recognition of families of related molecules. The selectivity of candidate proteins of the invention can be manipulated during selection or screening by including comparator target molecules for which binding affinity is either desired or not desired. For example, to create a highly selective protein of the invention that recognizes one member of a multimember family of target molecules, such as family of closely related proteins, a preselection can be made with the undesired target molecules, discarding the so-selected proteins of the invention, followed by a selection with the desired target molecule. Alternatively, the activity of the protein of the invention identified by selection or screening methods can be assessed by comparing the binding affinity to the desired target molecule with that of unrelated target molecules or related target molecules for which affinity is either desired or not desired. Such screening methods need not provide precise information, but for convenience may convey simple approximate measures of relative affinity, for example based on signal strength in an assay format similar to that of an enzyme linked immunosorbent assay (ELISA).

Solubility and Stability

Candidate proteins of the invention that have been identified by selection or screening can be further evaluated and modified if necessary for additional properties that are required for the field of use. For example, for the manufacturing of proteins of the invention intended for most uses, a candidate protein of the invention can be highly soluble and thermostable. Methods are provided by the present invention for the evaluation of the solubility and thermostability of proteins of the invention as well as their suitability for expression in properly folded form in *E. coli*. In general, methods for the evaluation of thermostability are well known in the art, and consist of thermal stress testing or extended storage testing at defined temperatures, followed by measurement of binding activity. In some cases a test for relative thermostability can be as simple as the measurement of the fraction of proteins of the invention remaining soluble following incubation of the proteins of the invention for a defined time at a particular temperature. Another suitable method for measuring thermostability is differential scanning calorimetry. Methods for the indirect assessment of folded status of proteins in *E. coli* are also known in the art, and in the present invention include fusion of the candidate protein of the invention to an easily monitored protein whose activity is only apparent in its properly folded form, such as GFP or an antibiotic resistance. The relative degree of folding has been found by others to be a property shared by both domains of a fusion protein in *E. coli*, so that if the protein of the invention moiety is not properly folded, the likelihood that the GFP or antibiotic resistance moiety will be folded is commensurately low. In such cases cells expressing inactive or improperly folded proteins of the invention will not show high green fluorescence or high antibiotic resistance.

Therapeutic Uses

The proteins of the present invention can be used as targeting principles to deliver other therapeutic or analytical elements to an organism in need of therapy or diagnosis. For example, they may be attached to highly active cytostatic or cytotoxic agents to effect the growth arrest or elimination of an undesired cell type, such as a neoplastic or pre-neoplastic cell, or for the reduction in mass of a hypertrophic tissue or organ such as a hypertrophic prostate, or for the elimination of populations of immune cells that are undesired, for example those promoting or causing autoimmune syndromes. Such cytostatic or cytotoxic agents may be synthetic or natural small molecules, for example, maytansine and its derivatives, anthraquinones, alkylating agents such as cyclophosphamide or its prodrug forms, tubulin-binding agents, geldanamycin or its derivatives, or enediyne antibiotics such as calicheamycin, among others. The cytostatic or cytotoxic agents may also be proteinaceous toxins or combinations of small molecules and proteinaceous toxins.

Bispecific Proteins of the Invention

Dimeric or higher multimeric proteins of the invention can be used to juxtapose cells or induce cellular actions by receptor crosslinking that may have a favorable therapeutic effect. For example, therapeutic strategies aimed at amplifying the cytotoxic action of macrophages, natural killer cells, or cytotoxic T cells have been described which rely upon the use of bispecific antibodies or related compositions. Such bispecific antibodies typically provide one antibody combining site that recognizes a target molecule on the cell type to be ablated, and a second antibody combining site that recognizes a cell surface receptor on macrophages, natural killer cells, or T cells that, if engaged, induces the cytolytic effector program of those cells, leading to destruction of the target molecule. Alternate forms of bispecific antibodies promote the selective disabling of responses by mast cells or B cells by producing crosslinks between activating receptors, such as the high affinity receptor for IgE on mast cells or the immunoglobulin receptor on B cells, and inactivating receptors. The coordination of the activating receptor and the inhibitory receptor frustrates the signals emanating from the activating receptor, resulting in a favorable therapeutic effect. Similar bispecific compositions can be provided by the proteins of the present invention, which can be joined by a variety of methods to provide bi- or multi-specific binding principles for therapeutic treatments.

Diagnostic Uses

Proteins of the invention can be used as antibody equivalents for many assay purposes. Proteins of the invention can serve as the capture or detection reagent for ELISA-type assays or as the detection reagent for ELISpot assays or for the enumeration of protein abundance by flow cytometric measurement technologies. Proteins of the invention can be conjugated (e.g., via a cysteine, an N-terminal fusion, or C-terminal fusion) to fluorophores, fluorescent proteins, enzyme substrates, or enzymes to aid in the detection and/or quantification of analyses of interest. Translational fusions of proteins of the invention to enzymes or other proteins that aid in the detection of analyses can be made and the resulting fusions can be expressed in prokaryotic or eukaryotic cells to provide a convenient renewable source of reagent. The favorable thermostability properties of proteins of the invention allow their use in arrays of analyte detector, for example in the planar format of protein binding arrays, or in the bead format of multiplexed fluorophore ratio indexed bead systems, such as the Luminex system. Detection of analyte binding with a protein of the invention can follow many of the assay format designs and detection schemes that have been disclosed for high sensitivity and selectivity detection by antibodies, such as light scattering, light surface plasmon scattering, fluorescence polarization, time resolved fluorescence, fluorescence autocorrelation, electroluminescence, chemiluminescence, fluorescence resonant energy transfer, fluorescence quenching or unmasking, coagulation or flocculation of beads, cells or other particles, or by providing nucleic acid or modified nucleic acid tags for detection by amplification methods including polymerase chain reaction, ligation-mediated probe amplification, branched nucleic acid assay, or isothermal amplification, with or without a ligation step; or by conveying enzymatic activities detectable by absorbance, fluorescence, evanescent field, or surface potential perturbation. Monospecific or multispecific proteins of the invention can be prepared to identify unique analyses or families of analyses. In addition, monomeric, or multimeric proteins of the invention can be used as capture or detection reagents.

Labeled proteins of the invention can be used to image diseased cells, tissues or organs, either in vivo or in vitro. Proteins of the invention can be conjugated to radionuclides, or to prosthetic groups incorporating or binding to other molecules including radionuclides. Common radionuclides used in imaging include F-18, I-131, I-123, Tc-99m, In-111 or Ga-67. Alternatively proteins of the invention can be conjugated to groups enclosing caged hyperpolarized xenon, or can be joined or attached to beads, nanoparticles or nanocrystals susceptible to detection by magnetic resonance imaging. Radionuclides can be detected by nuclear scintigraphy using equipment and methodology well known in the art, such as gamma cameras and positron emission tomography. In addition, images obtained by one modality, such as magnetic resonance imaging can be superimposed on images obtained by other modalities, such as nuclear scintigraphy, or two or more radionuclides of different spectral properties can be combined with different proteins of the invention, to permit better localization of images and more precise staging or diagnosis of disease conditions. Uses of such conjugated proteins of the invention include the in vivo imaging of tumors, infections, regions of ischemic damage or poor perfusion, clots, bone or eroded bone, sites of inflammation or degeneration, accumulations of amyloids, paraproteins or prion proteins, or to interrogate the status of prosthetic devices and/or their interfaces with normal or diseased tissue. Proteins of the invention labeled with enzymes, fluorophores, fluorescent proteins, ferritin, gold or silver particles, or electron dense beads, can be used in conjunction with microscopic or ultramicroscopic techniques to diagnose pathological conditions or to identify, enumerate or quantitate the burden of relevant target molecules that signify the disease status of the cells, tissues, organs or organisms being studied.

The imaging of tissues using labeled or conjugated proteins of the invention can be used to guide diagnostic or therapeutic procedures, such as biopsies, resections, radioablations, radiotherapy, or locally delivered chemotherapy.

Manufacturing Uses

The favorable thermostability and solubility properties of the proteins of the invention also permit their use as adsorption reagents for the purification of proteins and complex biological structures, such as vaccine components. The positive manufacturing economies of prokaryotic production allow proteins of the invention to be used in settings for which the routine use of antibody reagents or materials would be considered prohibitively expensive.

Typically, for a manufacturing use a protein of the invention having the desired selectivity, solubility, thermostability, and affinity for a target molecule will be prepared in a form that allows its constitution into an adsorbent, which may include a column medium, bead, or coated surface to which a target molecule stream is to be exposed. Following adsorption of the target molecule to the solid support, the nonbound material will be removed by one or more washing steps and the desired target molecule material will be eluted, typically by raising or lowering the pH, as is common in the elution of antibody-based affinity supports, or by exploiting the polyol responsiveness of the proteins of the invention. Various hydrophilic matrices that are used as supports for such affinity media are well known in the art and includes various, typically porous and crosslinked, polymers, such as crosslinked agaroses, dextrans, acrylamides, hydrophilic acrylates, hydrogels, or inorganic matrices such as controlled pore glass, or nonporous but fine particles such as magnetic beads, and functionalized or surface passivated silica or cellulose particles. Proteins of the invention can be attached to such media by methods such as electrophilic attack by aldehydes, oxiranes, activated carbonates, iminocarbonates, cyanate esters, haloacetamides, maleimides, or activated esters, including carbodiimide activated carboxylic acids. Many commercial suppliers of pre-activated media suitable for attachment of the proteins of the invention are known. In addition, the proteins of the invention can be engineered by the incorporation of specific residues or sequences that favor the attachment of the proteins of the invention to the media in a protein of the invention, site-selective manner.

Research Uses

Research and analytical uses of proteins of the invention include the replacement of antibodies for detection and quantitation of analyses in various contexts, for example in immunoblotting, ELISA, ELISpot, flow cytometry, bead-based coagulation or detection systems, for detection of analyses by light scattering, surface plasmon scattering, bioluminescent interferometry, chemiluminescent or electroluminescent detection, by fluorescence polarization, time-resolved fluorescence, fluorescence autocorrelation, fluorescence resonant energy transfer, or fluorescence quenching or unmasking. Proteins of the invention can be conjugated with various fluorophores or fluorescent proteins to provide probes for the presence or absence of analyses. The analyses may include proteins, carbohydrates, nucleic acids, lipids, small molecules of natural, synthetic or semisynthetic origin, as well as polymers, glasses, metals and alloys, or combinations of these. Proteins of the invention can be conjugated to enzymes, proteins, nucleic acids, carbohydrates, lipids, polymers, small molecules of natural, synthetic or semisynthetic origin, to provide an analyte detection method or additional functionality, or can be endowed with additional substituents having utility for detection or amplification of signal, such as by providing covalent or stable noncovalent attachment of nucleic acid or modified nucleic acid tags for detection by amplification methods including polymerase chain reaction, ligation-mediated probe amplification, branched nucleic acid assay, or isothermal amplification, with or without a ligation step. Proteins of the invention can be adsorbed on solid surfaces, such as plates, trays, capillaries, fabrics, nanotubes or wires, flexible or rigid sheets, beads, or particles, all of which may provide either surfaces for noncovalent absorption or chemically activated surfaces for covalent attachment. Such proteins of the invention-substituted surfaces may be used to provide either capture reagents, or in the case of bead or particulate adsorbed material, detection reagents. Examples of uses of labeled proteins of the invention include, without limitation, microscopy, ultramicroscopy, flow cytometry, flow microscopy, carbon nanotube-based chemiresistive affinity biosensing, immunoblotting, immunoprecipitation, spectroscopy, or in vivo imaging.

Methods of Preparation

Proteins of the present invention are often easily prepared by expression in prokaryotic cells, such as *E. coli*. Moreover proteins of the invention often have solubility properties that allow them to be readily purified using simple scalable steps amenable to high volume manufacturing.

EXAMPLES

Example 1. Generation of a Derivative CBM 32 Scaffold Protein for Specific Binding of Target Molecules (Library 2)

Library Construction

Library 2 variabilizes the following residues of SEQ ID NO: 1, 817-820 (QVYE, or loop V), 838-844 (KTLNGDT, or loop W), 931-935 (NINKW, or loop Z). We were able to isolate selective binders that were easily expressed at high level in *E. coli* (>50 mg/l culture). All of the data we show subsequently in this example are from Library 2 binders. FIG. 1 displays Library 2 loops as shaded and the Met labeled with an *. Half of the binding pocket for the normal sugar ligand is variabilized.

Affinity Scaffold Based on CBM

Figure 2:
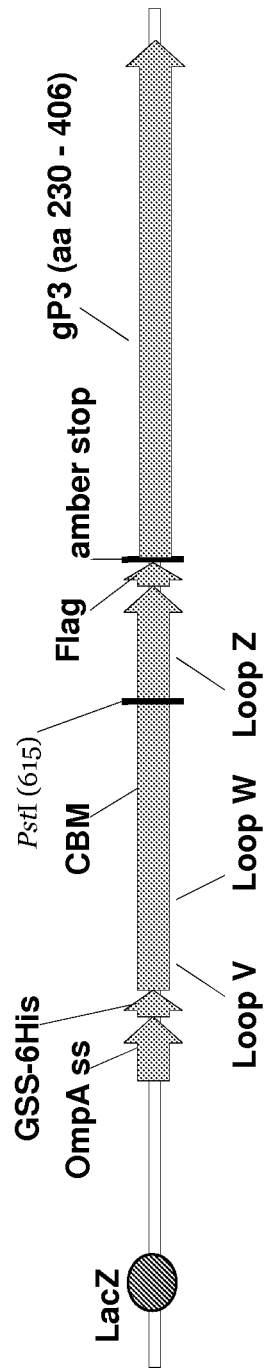
FIG. 2 is a schematic representing the region of the phagemid pComb3X encoding for the CRs and VLRs of the CBM affinity scaffold of library 2.

A cDNA coding for residues 807 to 946 of a carbohydrate binding module (Protein Data Bank 2W1Q) was codon optimized for expression in E. coli and synthesized by IDT. The cDNA was cloned into the phagemid pComb3X such that the CBM contained an N-terminal His tag and a C-terminal flag tag, and was fused N-terminally to a truncated form of gP3 (FIG. 2). To construct a library of variants of the scaffold CBM, we first amplified 1 ng of this phagemid using degenerate primer 397T-F, consisting of a mix of four consecutive phosphoramidite trimers (loop V), and the non-degenerate primer 398-R, in a 50 µl reaction with ClonAmp HiFi PCR Mix, according to manufacturer's instructions. The reaction cycle was at 98° C. for 10 sec, 65° C. for 10 sec, and 72° C. for 30 sec, repeated 30 times. The resulting amplicon was gel purified on a 1.1% agarose gel using Qiagen Minelute gel purification kit, and eluted in 12 µl elution buffer. The phosphoramidite trimer oligo contained one codon for each amino acid except for Cys and Met (and no stop codons). These primers contained overlapping regions so that the resulting amplicon could be fusion cloned and ligated in vivo using Clontech's InFusion HD Enzyme kit, with the resulting phagemid a mini-library with 4 variable codons in loop V, which consists of residues 817 through 820. Briefly, 495 ng of the gel purified amplicon was fusion cloned in a 50 µl reaction with 10 µl of 5× InFusion HD Enzyme and incubated at 50° C. for 15 min, and put on ice. The DNA was then concentrated and purified using a Qiagen PCRprep Minelute column, eluting in 10 µl EB. The DNA was desalted on a Millipore nitrocellulose membrane floating on 100 ml ddH$_2$O for 30 min, changing the water and repeating for 30 more minutes. The DNA library was electroporated into electrocompetent TG1 cells (Lucigen) by adding 1 µl of DNA at 40 ng/µl to each of 6 aliquots of 25 µl of cells on ice in 0.1 cm electroporation cuvettes. The DNA was electroporated using a BioRad micropulser on setting Ec1, producing a Tau of approximately 5.4, after which the cells and DNA were diluted with 1 ml per electroporation of Lucigen recovery media, pooled, and incubated at 37° C., at 275 rpm, for 1 h in a shaking incubator. To titer the sub-library, 10 µl of recovered culture was diluted ten-fold and 10 µl aliquots spotted onto 2×YT/glucose (2%)/Carbenicillin (100 µg/ml) (2×YT/glu/carb), and incubated overnight at 30° C. The remaining mini-library was expanded to 50 ml 2×YT/glu/carb and incubated overnight at 30° C., 250 rpm. The cells were pelleted and resuspended in 2×YT/18% glycerol at an OD$_{600}$ of 75 and stored at −80° C.

The phagemid mini-library was prepared by inoculating 50 ml 2×YT/gly/carb with 5 µl glycerol stock, growing overnight, and preparing phagemid using Qiagen Midiprep kit, resulting in 100 µl of 156 ng/µl phagemid DNA. To prepare this phagemid library to serve as template for construction of the library with Loops W and Z also randomized, 5 µg of phagemid was digested with 30 Units of PstI in 50 µl reaction with Buffer 3 (NEB) and BSA, and incubated for 1 h at 37° C. The "insert" was prepared by amplifying the region of CBM between Loops W and Z, which contained no variabilized residues, by amplifying 2 ng of native CBM using primers 404 F and 405 AR, which mutated M929L, using ClonAmp HiFi PCR Mix in a 100 µl reaction according to manufacturer's instructions, and cycled at 98° C. for 10 s, 60° C. for 10 s, and 72° C. for 10 s, cycling 30 times. Both the insert and the purified phagemid were gel purified on a 1.1% agarose gel using Qiagen minelute gel purification columns.

The phagemid was amplified using the phosphoramidite trimers containing randomized codons for loops W and Z, and also overlapping regions for annealing to the insert, which contained the interior, non-random region of CBM M929L. Briefly, 420 ng of PstI digested and purified phagemid was amplified with phosphoramidite timer primers 402-TR and 403-TF, using ClonAmp HiFi PCR Mix, according to manufacturer's instructions, in 42 reactions of 25 µl, cycling 15 times 98° C. for 10 s, 65° C. for 10 s, and 72° C. for 30 s. Primer 402T-R variabilized codons in Loop W, which code for residues 838-844. Primer 403T-F variabilized codons in Loop Z, which code for residues 931-935. The amplicon was gel purified on 1% agarose using eight Qiagen gel purification columns, eluting each one with 50 µl EB and combining. Both the amplified phagemid and the insert were PCRprep purified and eluted with 100 µl and 20 µl EB, respectively, yielding the phagemid at 152 ng/µl and the insert at 174 ng/µl. The primers and their respective sequences used are listed in FIG. 3.

Gibson Assembly of Phagemid and Insert.

The phagemid library was created by Gibson Assembly cloning the linear phagemid library, containing 4 variable codons in Loop V (residues 817-820), 7 variable codons in Loop W (residues 838-844), and 5 variable codons in Loop Z (residues 931-935), for a total of 16 variable residues in 3 loops, to the insert region between loops W and Z. Briefly, 4.17 µg of phagemid and 1.52 µg of insert were combined in an 830 µl reaction containing 415 µl of Gibson Assembly Master Mix (2×) (NEB), and incubated at 50° C. for 15 min and put on ice. The ligated DNA was purified and concentrated in one Qiagen Minelute PCRprep column, and eluted in 25 µl EB. The DNA was desalted on a VSWP 0.025 µM membrane (Millipore) on ddH$_2$O for 1 h with a water change at 30 min. The desalted DNA was adjusted to 75 ng/µl with ddH$_2$O and used to electroporate electrocompetent TG1 cells (Lucigen). Approximately 51 µl of DNA was added to 1.25 ml ice cold TG1 cells and pipetted up and down 4 times to mix on ice, after which 25 µl aliquots were transferred to 50 chilled electroporation cuvettes with 0.1 cm gaps on ice. The cells were electroporated on a Biorad minipulser on level Ec1, and immediately quenched with 975 µl Lucigen recovery media, pooled, and incubated at 37° C., 250 rpm for 1 h. To titer the library, 10 µl of recovered culture was serially diluted in 2×YT and 10 µl of each dilution spotted on 2×YT/glu/carb and incubated at 30° C. overnight. The remaining library was expanded to 3 L 2×YT/glu/carb and amplified overnight at 30° C., 250 rpm. The next day, the library was pelleted at 10 k×g, 10 min, 4° C. and the media discarded. The pellet was resuspended to an OD$_{600}$ of 75 in 2×YT/2% glucose/18% glycerol, aliquoted and stored at −80° C.

Library Panning for Binders to Maltose Binding Protein (MBP)

For the first round of panning, 3 L of 2×YT/glu/carb was inoculated with 4 ml of the C11 glycerol stock (OD$_{600}$=75), to an OD$_{600}$ of approximately 0.1 and grown at 37° C., 250 rpm until the OD$_{600}$ reached 0.5. From the initial culture, 750 ml was superinfected with 466 µl of VCSM13 (1e13 phage/ml) at a ratio of approximately 20 phage to 1 cell, and incubated at 37° C. for 30 min at 100 rpm, and then for 30 min at 250 rpm. The cells were pelleted at 10 k×g, 10 min, and the media discarded. The cells were resuspended in 1.5 L 2×YT/carb (100 µg/ml)/Kan (70 µg/ml), and incubated overnight at 30° C., 250 rpm. The cells were pelleted at 10 k×g for 10 min and the phage containing supernatant transferred to clean tubes containing 0.25 volume 5×PEG/NaCl (20% polyethylene glycol 6000/2.5 M NaCl), mixed well, and incubated on ice for 25 minutes. The phage was pelleted at 13 k×g, 25 min and the supernatant discarded. The phage was resuspended in 60 ml PBS and centrifuged at 13 k×g, 10 min to remove insoluble material. The supernatant was precipitated with 5×PEG again and incubated on ice for 5 min before spinning down the phage again at 13 k×g, 20 min. The supernatant was discarded and the pellet resuspended in 30 ml PBS, with an $A_{268}$ of 6.6.

For solution panning of biotinylated MBP, two sets of 100 µl of streptavidin coated magnetic beads slurry were washed 2×1 ml with PBS-T (applying a magnet in between washes to remove the supernatant), and blocked in 1 ml of 2% dry milk in PBS with 0.05% Tween20 (2% M-PBS-T) for 1 h, rotating, at rm temp. Unless stated otherwise, all panning and screening incubations are carried out at rm temperature. After blocking the beads, the magnet was applied and the blocking agent removed. To pre-clear the phage solution before incubating with the biotinylated antigen, 1 ml of phage solution (prepared in the previous step) was incubated on one set of the blocked beads for 1 h, rotating. The magnet was applied and the pre-cleared phage transferred to a clean tube. The biotinylated MBP (Avidity) was added to the pre-cleared phage solution at a concentration of 100 nM and incubated for 1.5 h rotating to allow the phage to bind to the antigen.

The phage/antigen solution was transferred to the second set of blocked beads and incubated for 20 min to capture antigen bound phage. The magnet was applied and the supernatant discarded. The beads were washed and resuspended eight times with 1 ml PBS-T, switching to fresh tubes after the third, fifth, and seventh wash, and precipitating the beads with the magnet in between each wash for approximately 2 min. The beads were eluted with 800 µl 0.1 M glycine, pH 2 for 10 min, the magnet applied, and the supernatant aspirated into a tube with 72 µl 2 M Tris base to neutralize before adding the entire neutralized eluant to 9 ml of mid-log phase XL1-blue cells ($OD_{600}$=0.44). The cells were infected for 45 minutes at 37° C., 150 rpm. The unamplified output titer was measured by preparing ten-fold serial dilutions of 10 µl of culture and spotting 10 µl of each on 2×YT/glu/carb agar plates and incubating overnight at 30° C. The culture was expanded to 100 ml 2×YT/glu/carb and incubated overnight at 30° C., 250 rpm, and then for a few hours at 37° C. in the morning.

The overnight cultures were harvested by measuring the $OD_{600}$, centrifuging the cells at 10 k×g, 10 min, and resuspending the cells to an $OD_{600}$ of 75 in 2×YT/18% glycerol. To prepare phage for the next round of panning, 5 ml of 2×YT/glu/carb was inoculated with 5 µl of the 75 $OD_{600}$ glycerol stock and incubated at 37° C., 250 rpm until the $OD_{600}$ reached 0.5. The cells were superinfected at 20:1 phage:cell, mixed well, and incubated at 37° C., 30 min, 150 rpm, then 30 min at 250 rpm. The cells were pelleted at 5500×g, 10 min, the glucose containing media discarded and the cells resuspended in 10 ml 2×YT/Carb/Kan and incubated overnight at 30° C., 250 rpm.

The overnight phage prep was centrifuged at 10 k×g, 10 min, and the supernatant transferred to 2.5 ml 5×PEG/NaCl, mixed, and incubated on ice for 25 min to precipitate the phage. The phage was pelleted at 13 k×g for 20 min, and the supernatant discarded. The phage was resuspended in 1 ml PBS and the insoluble material removed by centrifugation at 20 k×g for 5 min. The supernatant was applied to 0.25 volume of 5×PEG/NaCl and precipitated a second time for 5 min on ice. The phage was pelleted at 13 k×g, 5 min, 4° C., the supernatant removed, and the pellet resuspended in 750 µl PBS. The phage was prepared at $A_{268}$=0.8 in 2% M-PBS-T, and the panning continued as described, except in the third round the concentration of biotinylated antigen incubated with the pre-cleared phage was lowered to 10 mM, the phage concentration was lowered to an $A_{268}$ of 0.2, and the number of washes was increased to 12 to increase selectivity of higher affinity phage.

ELISA of Individual Clones Following Panning

At the end of the last panning round (usually after round 3 or 4), individual colonies were plated on 2×YT/glu/carb following the 45 minute 37° C., 150 rpm recovery of the infected XL1-blue cells with the eluted phage. The next day 96 colonies were inoculated into 400 µl 2×YT/glu/carb in a 96 well deep well culture plate, and grown overnight at 37° C., 300 rpm to generate a master plate, to which glycerol is added to 18% for storage at −80° C. To prepare an induction plate for the ELISA, 5 µl of each masterplate culture was inoculated into 400 µl fresh 2×YT/0.1% glu/carb and incubated for 2 h 45 min at 37° C., 300 rpm. IPTG was added to 0.5 mM and the plates incubated at 30° C., 300 rpm overnight. Because the phagemid contains an amber stop codon, some CBM protein is produced without the gpIII, even though XL1-blue is a suppressor strain, resulting in the periplasmic localization of some CBM, which some percentage is ultimately secreted to the media. The media then can be used directly in an ELISA. After the overnight induction, the plates are centrifuged at 1200×g for 10 min to pellet the cells.

Streptavidin or neutravidin coated microtiter plates (Pierce) were rinsed three times with 200 µl PBS, and coated with biotinylated MBP at 1 µg/ml at 100 µl/well and incubated 1 h. For blank controls, a plate was just incubated with 100 µl/well PBS. The wells were washed three times with 200 µl PBS-T, and blocked with 200 µl 2% M-PBS-T for 1 to 3 h. The block was removed and 50 µl of 4% M-PBS-T added to each well. At this point 50 µl of each induction plate supernatants were transferred to both a blank and an MBP coated well and pipetted 10 times to mix, and incubated 1 h. The plates were washed 4 times with 250 µl PBS-T in a plate washer using the dispense only function, and the plates dumped and slapped on paper towels in between washes. After the washes, 75 µl of 1/2000 dilution anti-flag-HRP in 4% M-PBS-T was added to each well and incubated 1 h. The secondary was dumped and the plates washed as before. The plates were developed by adding 75 µl TMB Ultra substrate (Pierce), and analyzed for positives compared to controls. Positives were grown up from the masterplate by inoculating 1 ml 2×YT/glu/carb with 3 µl glycerol stock and incubated for at least 6 hours at 37° C., 250 rpm. The cells were pelleted and the media discarded. Plasmid DNA was prepared from the pellets using the Qiagen miniprep kit, and the sequences determined by Sanger sequencing at Genewiz.

Expression and Purification of Binders

Positives identified from the ELISA using the secreted binders were subcloned into pET vectors containing an N- or C-terminal Cysteine, or a C-terminal linker, followed by a Cysteine (GGGGSGGGGSGGGC). Nomenclature for these constructs involves placing the C in front of the binder number or a C or LC after the binder number to denote N- or C-terminal Cys or linker-Cys, respectively. For example, the GFP binder 860 with a linker-Cys at the C-terminus is named P860LC. For the C-term Cys constructs, the CBM cDNA, including its N-terminal 6-His tag, was amplified from the pComb3X phagemid clones prepared in the previous section using primers 391 F and 450 R, in a 25 µl reaction containing 12.5 µl ClonAmp HiFi PCR Mix, and cycling 30 times 98° C. for 10 s, 65° C. for 10 sec, and 72°

Figure 4:
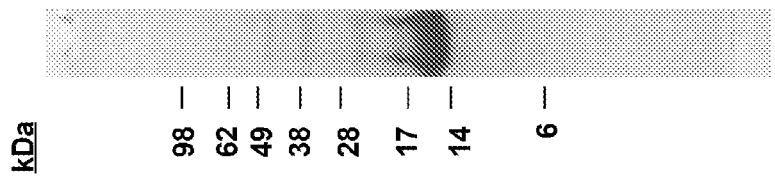
FIG. 4 is an image showing a segment of a polyacrylamide gel containing a purified CBM scaffold protein of library 2 and with a molecular weight of 15.6 kDa that has been separated by electrophoresis.

C. for 30 sec. A pET15b (Novagen) vector containing native CBM M929L was used as template (although pET15b could be used) for amplifying the vector using primers 390 R and 387 F in a 50 µl reaction containing 25 µl ClonAmp HiFi PCR Mix, cycling the same way. For the N-terminal Cys constructs, the cloning was carried out exactly the same way, except the CBM was amplified with primers 508 F and 392 R, and the vector amplified with 387 F and 507 R (except in the case of PC896 and PC923, in which the CBM was amplified with 493 F and 392 R, and the vector amplified with 387 F and 494 R). For the C-terminal linker-Cys constructs, the cloning was carried out exactly the same way, except the CBM was amplified with 391A F and 527 R, and the vector amplified with 540 F and 390A R (see FIG. 13 for primer sequences). These two amplicons were gel purified on 1.1% agarose gel using Qiagen minelute gel purification kits. Between 20 and 100 ng of insert and vector were fusion cloned in a 5 µl InFusion reaction at 50° C., 15 min (Clontech). Chemically competent BL21 DE3 *E. coli* were heat-shocked with 1.5 µl of the InFusion reaction and recovered in 500 µl SOC for 1 h, 37° C., 250 rpm. The cells were plated on 2×YT/glu/carb and incubated overnight at 37° C. Individual colonies were grown up in 3 ml 2×YT/glu/carb cultures for at least 7 h, after which plasmid was purified for sequencing to confirm insertion of the CBM cDNA. Meanwhile, the cultures were seeded into 100 ml 2×YT/carb and grown to an $OD_{600}$ of 0.8 at 37° C., 250 rpm, induced to 0.5 mM IPTG and incubated overnight at 30° C., 250 rpm. The overnight cultures were pelleted at 10 k×g, 10 min, at 4° C., and the media discarded. The pellets were lysed in 10 ml 6 M Guanidine-HCl, 0.1 M $NaH_2PO_4$, 10 mM Tris, pH 8 (Buffer A), and incubated overnight rotating at room temperature. The insoluble material was pelleted at 30 k×g, 10 min, at 4° C., and the supernatant transferred to a clean tube containing 1 ml Ni-NTA SF (Qiagen) equilibrated in the same buffer, and incubated overnight rotating at rm temp. The beads were pelleted at 1 k×g, 1 min, and the flow through discarded. The beads were washed three times with 5 ml 8 M Urea, 0.1 M $NaH_2PO_4$, 10 mM Tris, pH 8 (Buffer B) including 20 mM imidazole, and 5 mM beta-mercaptoethanol (B-me), and another three times with the same buffer with no B-me. The protein was eluted with five 1 ml aliquots of Buffer A including 250 mM imidazole, and pooled in one tube. The protein was quantified by measuring the absorbance at 280 nm using an extinction coefficient of 33,690$M^{-1}$ $cm^{-1}$. Purity was assessed by buffer exchanging a small portion of the protein into Buffer B by ultrafiltration with a cutoff of 3000 Da, then analyzing ten or more micrograms of protein on a 12% Bis-Tris NuPage stained with GelCode Blue (FIG. 4).

Conjugation of Binders to Chromatography Resin

The purified protein in Buffer A was directly conjugated to Sulfolink beaded agarose (Thermo). Briefly, 100 µl of packed resin was equilibrated by washing the beads three times with at least five bed volumes of Buffer A, and transferring to a 1.3 ml column. The protein was added at a concentration between 2 and 12 mg/ml in a volume of 220 µl, and incubated rotating at rm temp for 15 min. The columns were stood upright for 30 min, and allowed to drain. The columns were washed three times with 600 µl Buffer A, then incubated with 800 µl 50 mM L-Cys and incubated rotating for 15 min, stood upright for an additional 15 min, and drained to the bed. The resin was washed two times with 800 µl 1 M NaCl, and the protein refolded on the column by washing with four times 800 µl 20 mM MoPS, 150 mM NaCl, 1 mM $CaCl_2$, pH 6.5. The beads were transferred to a clean tube and azide added to the MOPS buffer at 0.05% to inhibit microbial growth.

Figure 5A:
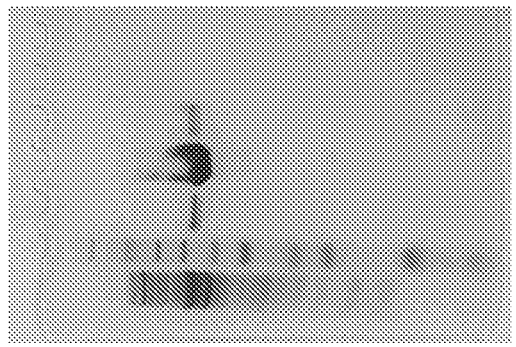
FIGS. 5A and 5B are images of two polyacrylamide gels displaying the results of a column purification using a CBM affinity scaffold protein containing specific VLRs from library 2 that target maltose binding protein (MBP).
Figure 5B:
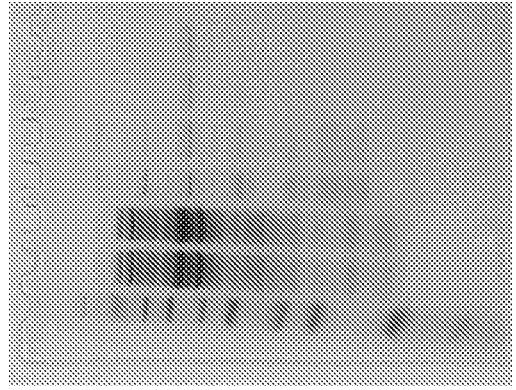

Affinity Purification of Antigen from *E. coli* Whole Cell Lysate Using Binder Conjugated to Cross-Linked Agarose Beads BL21DE3 *E. coli* cells were grown to an $OD_{600}$ of 4.9, pelleted at 10 k×g, 10 min, 4° C., the media discarded and the pellets frozen. A whole cell lysate was prepared by lysing pellets from 70 ml of culture with 18 ml BPER (Pierce), and incubating 20 min rotating at rm temp. The insoluble material was pelleted at 30 k×g, 10 min, 4 C, and the supernatant transferred to a clean tube. The cleared lysate was diluted to 50 ml with 20 mM MOPS, 150 mM NaCl, pH 6.5 (MOPS buffer) and spiked with antigen (maltose binding protein, MBP, in this case) to a final concentration of 0.018 mg/ml. The final "$OD_{600}$" of the spiked lysate was 6.5 (calculated as final OD if cells were not lysed). To prepare the affinity resin, 700 µl of packed beads, prepared as described above, was washed three times with 10 ml of MOPS buffer including 1 mM $CaCl_2$. The spiked lysate was incubated with the resin rotating at 4° C. for 2 h. The beads were pelleted at 1 k×g, 10 min, and the FT removed by aspiration. The beads were washed five times with 10 ml MOPS buffer with 1 mM $CaCl_2$ and 0.05% Tween20, with the last wash containing no $CaCl_2$ or Tween20. The beads were transferred to a column with the wash buffer and drained. The column was washed with four times 700 µl MOPS buffer plus 0.1 M EDTA and the washes collected. The bound protein was eluted with seven times with 700 µl Polyol elution buffer (10 mM Tris, 1 mM EDTA, 0.75 M ammonium sulfate, 40% propylene glycol, pH 7.9), and the fractions collected. The washes and eluted fraction were analyzed on 12% Bis-Tris NuPAGE SDS-PAGE in SDS gels (Invitrogen) in MES running buffer-sample reducing buffer after boiling for 5 min, as described (FIG. 5).

Figure 6:
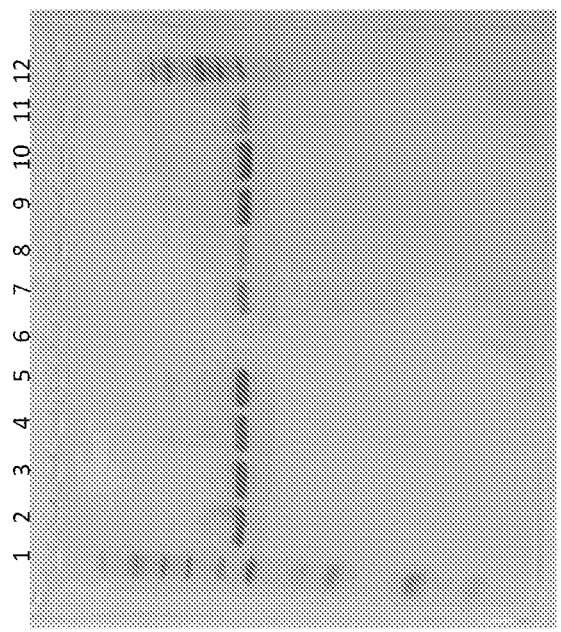
FIG. 6 is an image of a polyacrylamide gel displaying resultant purified green fluorescent protein (GFP) following purification with one of ten specific CBM variants from library 2 targeting GFP, where lane 1 is a molecular weight marker; lanes 2-11 each contain resultant purified GFP from one of the ten CBMs selected; and lane 12 is total protein lysate from E. coli spiked with GFP (60 ng/μl).

FIG. 6 shows a similar purification of green fluorescent protein (GFP) from an *E. coli* whole cell lysate using several different GFP binders bound to sulfolink resin. Briefly, GFP binders were conjugated to sulfolink resin as described above, and 50 µl of packed resin used to purify GFP from 1.2 ml *E. coli* lysate spiked with 60 ng/µl GFP. The beads were incubated in the spiked lysate for 2 h at 4 C. The beads were washed four times with 1 ml MOPS buffer with 1 mM $CaCl_2$ and 0.05% Tween20, and eluted with 250 µl Polyol elution buffer. The eluted fractions and the spiked lysate were analyzed by SDS-PAGE in SDS-sample reducing buffer after boiling 5 min, as described.

Examples of proteins of the invention from Library 2 that were identified as binding MBP include those below:

```
819, SEQ ID NO: 17:
NPSLIRSESWFLWIGNEANLLDGDDNTGVWYWRWWGEKSLAGEFIGLDLG

KEIKLDGIRFVIGKNGGGSSDKWNKFKLEYSLDNESWTTIKEYDKTGAPA

GKDVIEESFETPISAKYIRLTNLEQSWTNLTFSEFAIVSD

822, SEQ ID NO: 18:
NPSLIRSESWQLNNGNEANLLDGDDNTGVWYVANVGTQSLAGEFIGLDLG

KEIKLDGIRFVIGKNGGGSSDKWNKFKLEYSLDNESWTTIKEYDKTGAPA

GKDVIEESFETPISAKYIRLTNLETSGWGLTFSEFAIVSD
```

-continued

824, SEQ ID NO: 19:
NPSLIRSESWYPWVGNEANLLDGDDNTGVWYWHAWGAPSLAGEFIGLDLG

KEIKLDGIRFVIGKNGGGSSDKWNKFKLEYSLDNESWTTIKEYDKTGAPA

GKDVIEESFETPISAKYIRLTNLEQIFAHLTFSEFAIVSD

Example 2. A Derivative CBM 32 Scaffold Protein for Specific Binding of Target Molecules (Library 1)

Library 1 variablizes the following residues of SEQ ID NO: 1: 817 (Q), 839-844 (TLNGDT), 931-935 (NINKW), 872-878 (GGGSSDK), and 902-907 (TGAPAG). We isolated phage displaying selective binders from this library but had difficulty expressing the resulting proteins at high levels in *E. coli*.

FIG. 8 shows a recombinant binder from Library 1, ME3-C11, specifically binding to maltose binding protein in a Western blot application. In this experiment, whole cell soluble bacterial lysates from *E. coli* strain DH10bT1R (7 μg per lanes 1, 3, 5, 7, 9, and 11) and 100 ng recombinant maltose binding protein (0.1 μg per lanes 2, 4, 6, 8, 10, and 12) were electrophoresed on 12% Bis-Tris SDS-PAGE and either stained with Coomassie blue (Panel B), or transferred to a PVDF membrane. The membrane was blocked, incubated for 1 h with ME3-C11 at the indicated concentration, washed, and incubated with secondary anti-flag-HRP (lanes 1-8), or anti-MBP-HRP (lanes 9 and 10), for 1 h. The membrane was washed and developed with TMB for membranes (Panel A).

Examples of proteins of the invention from Library 1 that bind MBP include those below:

ME3-A9, SEQ ID NO: 20:
NPSLIRSESWTVYEGNEANLLDGDDNTGVWYKYVPSTDSLAGEFIGLDLG

KEIKLDGIRFVIGKNVFFRPVIWNKFKLEYSLDNESWTTIKEYDKFLPDV

AKDVIEESFETPISAKYIRLTNMEGYGISLTFSEFAIVSD

ME3-C7, SEQ ID NO: 21:
NPSLIRSESWIVYEGNEANLLDGDDNTGVWYKPLDFPFSLAGEFIGLDLG

KEIKLDGIRFVIGKNASCGFDAWNKFKLEYSLDNESWTTIKEYDKISPSY

SKDVIEESFETPISAKYIRLTNMEICVCFLTFSEFAIVSD

ME3-C11, SEQ ID NO: 22:
NPSLIRSESWCVYEGNEANLLDGDDNTGVWYKLCPSPFSLAGEFIGLDLG

KEIKLDGIRFVIGKNGYLGSDAWNKFKLEYSLDNESWTTIKEYDKNHNST

HKDVIEESFETPISAKYIRLTNMEFCLSDLTFSEFAIVSD

Example 3. Thermostable CR Mutants

Table 2 summarizes the results of a thermal shift assay (TSA) analysis of protein scaffold CBM (PDB 2W1Q), residues 807-946, and various mutants. All proteins contained an N-terminal His-tag.

TABLE 2

| CBM Protein | Tm (° C.) | Buffer |
|---|---|---|
| nCBM | 57.2 | 87.5 mM Citrate, 0.5M NaCl, pH 5.5 |
| G834F | 60.5 | 87.5 mM Citrate, 0.5M NaCl, pH 5.6 |
| K860P | 56 | 87.5 mM Citrate, 0.5M NaCl, pH 5.7 |
| S815R | 55.5 | 87.5 mM Citrate, 0.5M NaCl, pH 5.8 |
| E849D | 55.5 | 87.5 mM Citrate, 0.5M NaCl, pH 5.9 |
| K922R | 59 | 87.5 mM Citrate, 0.5M NaCl, pH 5.10 |
| G834F, K922R | 62.5 | 98 mM Citrate, 100 mM NaCl, pH 5.5 |
| G834F, K922R, S815R, E849D | 62 | 100 mM Citrate, 250 mM NaCl, 5 mM CaCl2, pH 5.5 |
| nCBM | 63.5 | 100 mM Citrate, 250 mM NaCl, 5 mM CaCl2, pH 5.5 |
| G834F | 65 | 100 mM Citrate, 250 mM NaCl, 5 mM CaCl2, pH 5.5 |
| K922R | 64 | 100 mM Citrate, 250 mM NaCl, 5 mM CaCl2, pH 5.5 |
| G834F, K922R, S815R, E849D | 62 | 100 mM Citrate, 250 mM NaCl, 5 mM CaCl2, pH 5.5 |
| G834F, K922R, F882Y | 64.5 | 100 mM Citrate, 250 mM NaCl, 5 mM CaCl2, pH 5.5 |
| G834F, K922R, L888K | 65 | 100 mM Citrate, 250 mM NaCl, 5 mM CaCl2, pH 5.5 |
| G834F, K922R, E891K | 65 | 100 mM Citrate, 250 mM NaCl, 5 mM CaCl2, pH 5.5 |
| G834F, K922R, V944R | 64.5 | 100 mM Citrate, 250 mM NaCl, 5 mM CaCl2, pH 5.5 |
| nCBM | 57 | 20 mM MOPS, 150 mM NaCl, pH 6.5 |
| K922R | 57 | 21 mM MOPS, 150 mM NaCl, pH 6.5 |
| G834F, K922R, V944R, M929K | 52 | 22 mM MOPS, 150 mM NaCl, pH 6.5 |
| G834F, K922R, V944R, M929L | 52 | 23 mM MOPS, 150 mM NaCl, pH 6.5 |
| G834F, K922R, V944R, M929R | 51 | 24 mM MOPS, 150 mM NaCl, pH 6.5 |
| K922R, V944R | 53 | 25 mM MOPS, 150 mM NaCl, pH 6.5 |
| K922R, M929K | 57 | 26 mM MOPS, 150 mM NaCl, pH 6.5 |
| K922R, M929L | 58 | 27 mM MOPS, 150 mM NaCl, pH 6.5 |
| K922R, M929R | 55 | 28 mM MOPS, 150 mM NaCl, pH 6.5 |

Example 4. Validation of Binders Generated Against Various Target Antigens

CBM binders were generated against a set of target antigens (e.g., GFP, MBP, murine IgG, rabbit IgG, beta-D-galactosidase, NusA, Sumo, thioredoxin, neutravidin, streptavidin, V5 epitope, mCherry, cmyc, and FLAG) and validated by SDS-PAGE analysis and/or ELISA, according to the methods described in Example 1. The amino acid sequences of each of the validated binders are provided below, with the strongest candidate binder for each target listed as the primary binder. Also provided, for each target antigen, are the amino acid sequences of the antigen, the amino acid sequences of antigens validated, applications tested in the experiments described herein, and/or the amino acid sequences of additional binders for that target antigen.

FIG. 9 shows the results of SDS-PAGE analysis of antigens purified from whole E. coli cell lysates using the CBM based binders generated in Examples 1, 2, and 5. With respect to the data shown in FIG. 9, Table 3 below summarizes the various conditions used for the affinity purification of antigens from E. coli lysates using binder-conjugated affinity resins. Affinity purification was performed as described in Example 1, with the following exceptions. The 1M salt wash following conjugation of the binders to the sulfolink beads was omitted. Instead of the high salt wash, the beads were refolded directly after closing out any remaining active sites with L-Cys by washing 2×800 µl 20 mM MoPS, 150 mM NaCl, pH 6.5 to remove the phosphate, and then 4× with the same buffer plus 1 mM $CaCl_2$ to refold the binders on the beads. During the affinity purification of antigens from E. coli lysates, after draining the lysate to the resin bed, the beads were washed between 4 and 8 times with several column volumes of PBS or PBS-T, and eluted with polyol elution buffer (or 8M Urea, 0.1 M $NaH_2PO_4$, 10 mM Tris, pH 8) as described in detail in Table 3. This protocol was scaled as necessary depending on the quantity of resin required.

Figure 10:
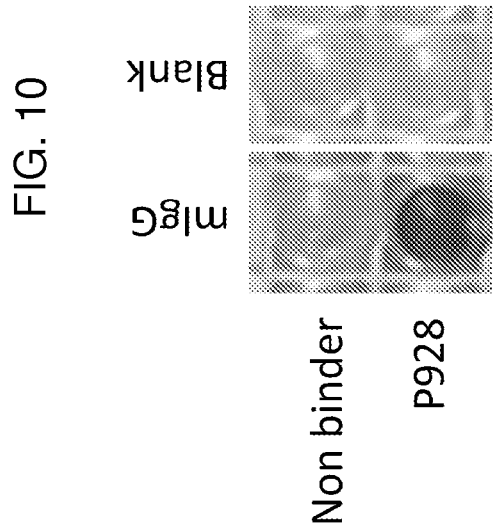
FIG. 10 is an image showing ELISA analysis of P928 against immobilized mIgG. Neutravidin coated microtiter plates were coated with biotinylated mIgG or PBS and blocked with 2% M-PBS-T. Primary antibody solution was applied in the form of media from cultures of E. coli harboring phagemid containing gP3 fusion constructs of binders possessing a 6-His tag and an amber stop codon. The primary antibody was probed with secondary anti-His-HRP and stained with TMB.
Figure 11:
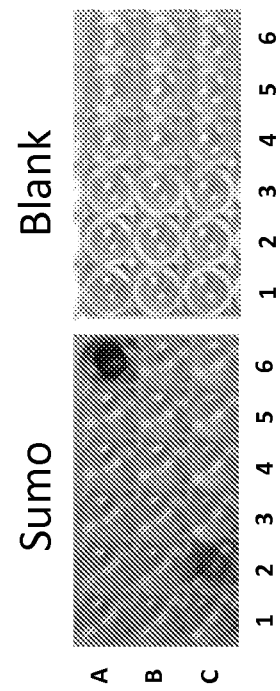
FIG. 11 is an image showing ELISA analysis of P971 and P973 against immobilized Sumo. Neutravidin coated microtiter plates were coated with Biotinylated Sumo or PBS (Blank) and blocked with 2% M-PBS-T. Primary antibody solution was applied in the form of media from cultures of E. coli harboring phagemid containing gP3 fusion constructs of binders possessing a 6-His tag and an amber stop codon. The primary antibody was probed with secondary anti-His-HRP and stained with TMB. Wells A6 and C2 represent clones P971 and P973, respectively. The clones tested in all the other wells shown were negative (non-Sumo binders).
Figure 12:
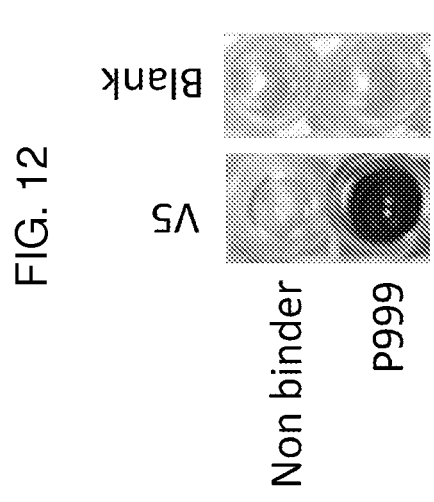
FIG. 12 is an image showing ELISA analysis of P999 against immobilized V5 peptide. Maleimide activated microtiter plates were coated with V5 peptide containing a single C-terminal Cys or PBS (Blank) and blocked with 2% M-PBS-T. Primary antibody solution was applied in the form of media from cultures of E. coli harboring phagemid containing gP3 fusion constructs of binders possessing a 6-His tag and an amber stop codon. The primary antibody was probed with secondary anti-His-HRP and stained with TMB.

Several of the remaining CBM based binders were validated by ELISA. For example, ELISA data for the mIgG binder P928 is shown in FIG. 10. ELISA data for the SUMO binders P971 and P973 is shown in FIG. 11. ELISA data for the V5 binder P999 is shown in FIG. 12. The set of primers used to construct the CBM phage library are shown in FIG. 13.

TABLE 3

Figure 9 Key—Conditions for affinity purification of antigens from E. coli lysates using CBM affinity resins.

Figures 9A, 9B, 9C, 9D, 9E, 9F, 9G, 9H:
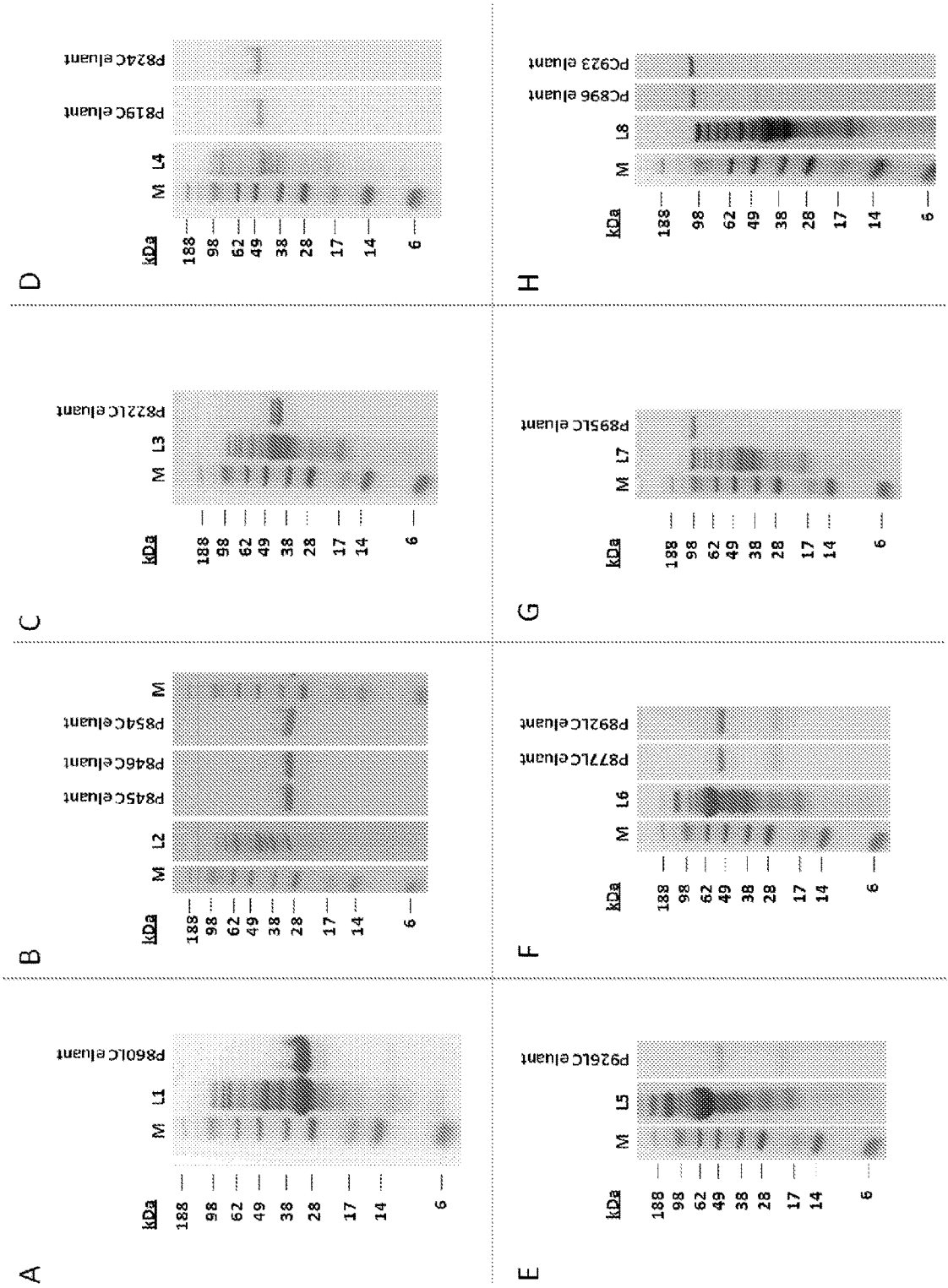
FIGS. 9A-9T are images showing SDS-PAGE analysis of affinity purification of antigens from E. coli BL21 DE3 whole cell lysates using CBM based binders conjugated to agarose beads. E. coli were lysed with BPER (Thermo), cleared by centrifugation, and diluted with 20 mM MOPS, 150 mM NaCl, pH 6.5. The lysate was spiked with recombinant antigen (unless lysate contained overexpressed antigen), and incubated with cross-linked agarose beads conjugated to indicated binders. Beads were washed and eluted with polyol elution buffer. The affinity purification details for each experiment are detailed in Example 4 and tabulated in Table 3 below. Lane M=marker. L1-L20 indicate E. coli lysates detailed in Table 3. Eluants from specific affinity resins are indicated above the lanes. For example, P860LC eluant denotes the eluant from P860LC affinity resin incubated with lysate L1. A and B: GFP binders, C and D: MBP binders, E: mIgG binder, F: rIgG binders, G and H: beta-D-galactosidase binders, I and J: NusA binders, K: SUMO binder, L and M: thioredoxin binders, N and O: neutravidin binders, P: streptavidin binder, Q: 3X-V5 epitope binder, R: mCherry binder, S: 3X-cmyc binder, T: Flag epitope binder.
Figures 9I, 9J, 9K, 9L, 9M, 9N, 9O, 9P:
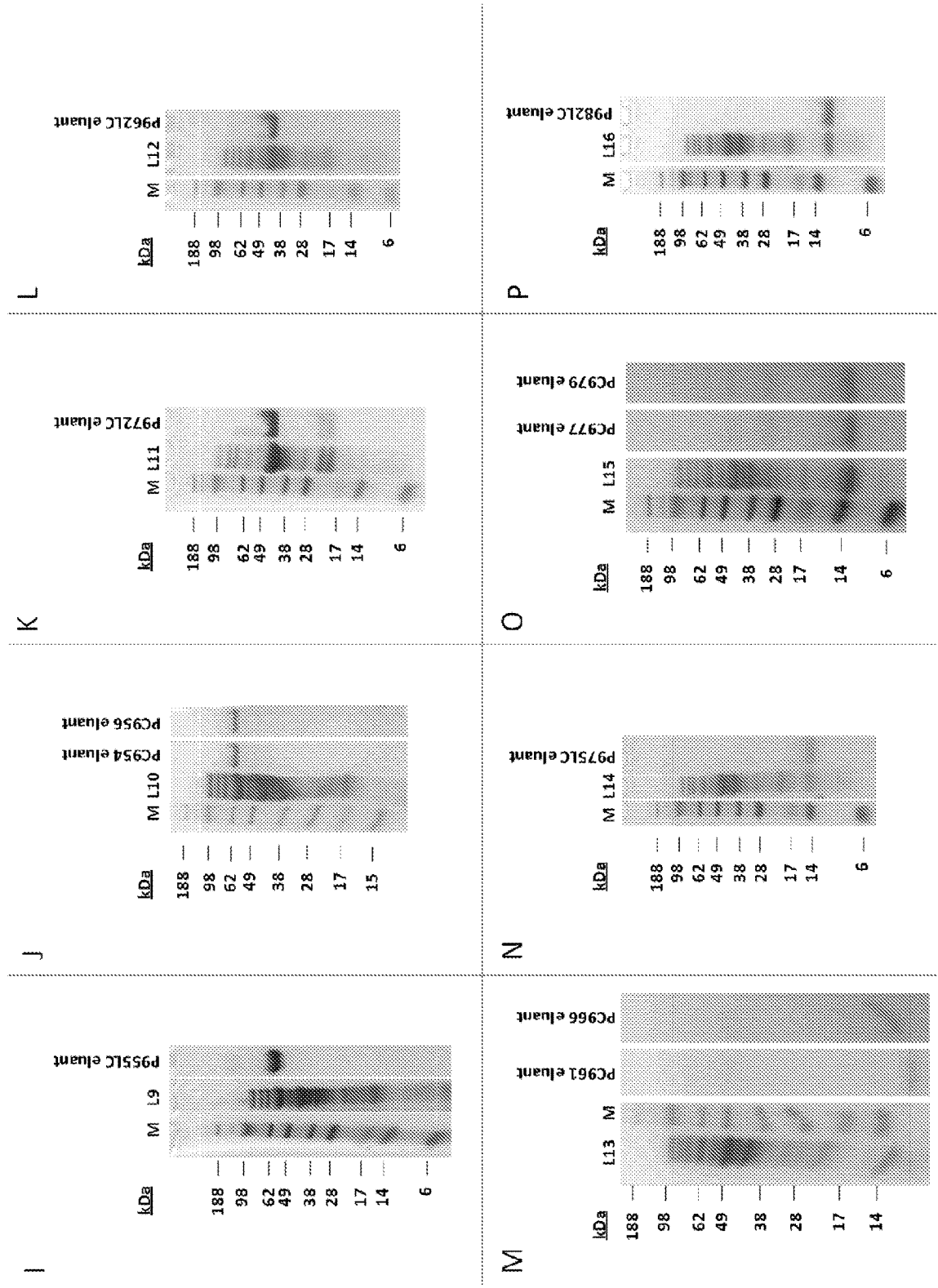
Figures 9Q, 9R, 9S, 9T:
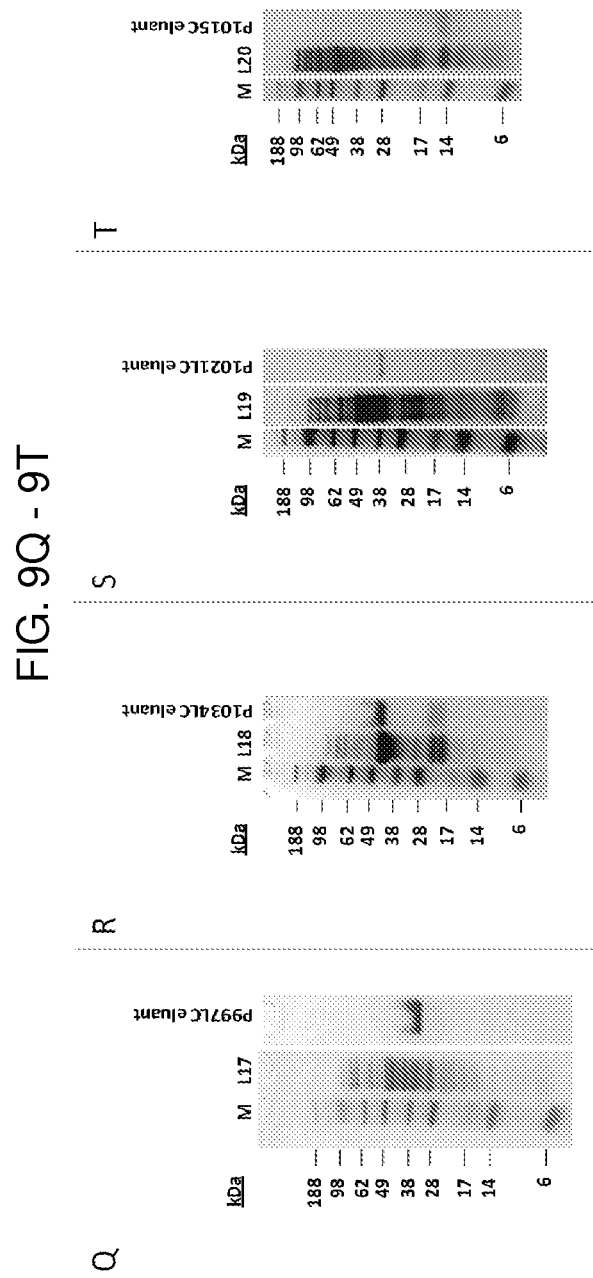

| Figure | Affinity Resin | Antigen | Resin vol (µl) | Lysate name | Spiked E.coli lysate equivalent $OD_{600}$ | Concentration of antigen in spiked lysate (mg/ml) | Spiked lysate vol applied to affinity resin (ml) | Vol of polyol eluate (µl) | Final BPER % in lysate | Vol of eluant loaded on SDS-PAGE (µl) |
|---|---|---|---|---|---|---|---|---|---|---|
| FIG 9A | P860LC | GFP | 20 | L1 | 8 | n.a. * | 0.8 | 180 | 11 | 13 |
| FIG 9B | P845C | GFP | 50 | L2 | 12 | 0.06 | 1.2 | 250 | 30 | 16 |
| FIG 9B | P846C | GFP | 50 | L2 | 12 | 0.06 | 1.2 | 250 | 30 | 16 |
| FIG 9B | P854C | GFP | 50 | L2 | 12 | 0.06 | 1.2 | 250 | 30 | 16 |
| FIG 9C | P822LC | MBP | 20 | L3 | 8 | 0.06 | 0.75 | 120 | 20 | 16 |
| FIG 9D | P819C | MBP | 50 | L4 | 6.5 | 0.018 | 1.1 | 100 | 30 | 16 |
| FIG 9D | P824C | MBP | 50 | L4 | 6.5 | 0.018 | 1.1 | 100 | 30 | 16 |
| FIG 9E | P926LC | mIgG | 20 | L5 | 8 | 0.06 | 0.75 | 120 | 20 | 16 |
| FIG 9F | P877LC | rIgG | 20 | L6 | 8 | 0.06 | 0.75 | 120 | 20 | 16 |
| FIG 9F | P892LC | rIgG | 20 | L6 | 8 | 0.06 | 0.75 | 120 | 20 | 16 |
| FIG 9G | P895LC | Bgal | 20 | L7 | 8 | 0.06 | 0.75 | 120 | 20 | 16 |
| FIG 9H | PC896 | Bgal | 10 | L8 | 12.4 | 0.04 | 1.0 | 40 | 32 | 16 |
| FIG 9H | PC923 | Bgal | 10 | L8 | 12.4 | 0.04 | 1.0 | 40 | 32 | 16 |
| FIG 9I | P955LC | NusA | 20 | L9 | 16 | 0.06 | 0.75 | 120 | 20 | 16 |
| FIG 9J | PC954 | NusA | 50 | L10 | 15.6 | 0.06 | 0.75 | 200 ** | 20 | 16 |
| FIG 9J | PC956 | NusA | 50 | L10 | 15.6 | 0.06 | 0.75 | 200 ** | 20 | 16 |
| FIG 9K | P972LC | SUMO | 200 | L11 | 8 | n.a. * | 5.0 | 1160 | 20 | 16 |
| FIG 9L | P962LC | Trx-GFPMut2 | 20 | L12 | 8 | n.a. * | 1.0 | 120 | 20 | 16 |
| FIG 9M | PC961 | Trx | 50 | L13 | 15.6 | 0.06 | 0.75 | 200 ** | 20 | 16 |
| FIG 9M | PC966 | Trx | 50 | L13 | 15.6 | 0.06 | 0.75 | 200 ** | 20 | 16 |
| FIG 9N | P975LC | Neutravidin | 20 | L14 | 8 | 0.06 | 0.75 | 120 | 20 | 16 |
| FIG 9O | PC977 | Neutravidin | 10 | L15 | 15.6 | 0.38 | 0.4 | 80 | 20 | 16 |
| FIG 9O | PC979 | Neutravidin | 10 | L15 | 15.6 | 0.38 | 0.4 | 80 | 20 | 16 |
| FIG 9P | P982LC | Streptavidin | 20 | L16 | 8 | 0.06 | 0.75 | 120 | 20 | 16 |
| FIG 9Q | P997LC | GFPMut2-3X-V5 | 20 | L17 | 8 | n.a. * | 1.0 | 120 | 20 | 16 |
| FIG 9R | P1034LC | mCherry | 20 | L18 | 8 | n.a. * | 1.0 | 120 | 20 | 16 |
| FIG 9S | P1021LC | GFPMut2-3X-cmyc | 20 | L19 | 8 | n.a. * | 0.75 | 100 *** | 11 | 16 |
| FIG 9T | P1015C | VHH-flag | 20 | L20 | 15.6 | 0.1 | 0.9 | 150 | 20 | 16 |

* BL21DE3 cells overexpressing antigen: concentration of antigen in lysate not measured
** Eluted with 8M Urea, 100 mM $NaH_2PO_4$, 10 mM Tris, pH 8
*** Eluted with 0.1M glycine, pH 2.

1. Binders to GFP
Primary Binder: P860LC
MGSSHHHHHHNPSLIRSESWDEWFGNEANLLDGDDNTGVWYVSFADNYSLAGEFIGLDLGKEIKLDGIR

FVIGKNGGGSSDKWNKFKLEYSLDNESWTTIKEYDKTGAPAGKDVIEESFETPISAKYIRLTNLENRWSYL

TFSEFAIVSDGGGGSGGGGSGGGC

Antigen: GFPMut2; biotinylated, C-term Avitag-6His (GFP S65A, V68L, S72A;
derived from Accession #ABN41558)
MSKGEELFTGVVPILVELDGDVNGHKFSVSGEGEGDATYGKLTLKFICTTGKLPVPWPTLVTTFAYGLQC

FARYPDHMKQHDFFKSAMPEGYVQERTIFFKDDGNYKTRAEVKFEGDTLVNRIELKGIDFKEDGNILGHK

LEYNYNSHNVYIMADKQKNGIKVNFKIRHNIEDGSVQLADHYQQNTPIGDGPVLLPDNHYLSTQSALSKDP

NEKRDHMVLLEFVTAAGITHGMDELYKGGGLNDIFEAQKIEWHEGAHHHHHH

Validated Reactivity: GFP
MSKGEELFTGVVPILVELDGDVNGHKFSVSGEGEGDATYGKLTLKFICTTGKLPVPWPTLVTTFSYGVQC

FSRYPDHMKQHDFFKSAMPEGYVQERTIFFKDDGNYKTRAEVKFEGDTLVNRIELKGIDFKEDGNILGHK

LEYNYNSHNVYIMADKQKNGIKVNFKIRHNIEDGSVQLADHYQQNTPIGDGPVLLPDNHYLSTQSALSKDP

NEKRDHMVLLEFVTAAGITHGMDELYK
Applications Tested
Immunoprecipitation (IP) (FIG. 9A)

Additional GFP Binders (FIG. 9B)
>P845C
MGSSHHHHHHNPSLIRSESWARWAGNEANLLDGDDNTGVWYWAKKNNISLAGEFIGLDLGKEIKLDGIR

FVIGKNGGGSSDKWNKFKLEYSLDNESWTTIKEYDKTGAPAGKDVIEESFETPISAKYIRLTNLETTFGGLT

FSEFAIVSDC

>P846C
MGSSHHHHHHNPSLIRSESWATWHGNEANLLDGDDNTGVWYWDDDYNNSLAGEFIGLDLGKEIKLDGI

RFVIGKNGGGSSDKWNKFKLEYSLDNESWTTIKEYDKTGAPAGKDVIEESFETPISAKYIRLTNLEPQWG

GLTFSEFAIVSDC

>P854C
MGSSHHHHHHNPSLIRSESWSAWIGNEANLLDGDDNTGVWYYNYAKNWSLAGEFIGLDLGKEIKLDGIR

FVIGKNGGGSSDKWNKFKLEYSLDNESWTTIKEYDKTGAPAGKDVIEESFETPISAKYIRLTNLEEKWSYL

TFSEFAIVSDC

2. Binders to MBP
Primary Binder: P822LC
MGSSHHHHHHNPSLIRSESWQLNNGNEANLLDGDDNTGVWYVANVGTQSLAGEFIGLDLGKEIKLDGIR

FVIGKNGGGSSDKWNKFKLEYSLDNESWTTIKEYDKTGAPAGKDVIEESFETPISAKYIRLTNLETSGWGL

TFSEFAIVSDC

Antigen: Maltose Binding Protein (MBP); biotinylated and C-term avitagged
(Derived from Accession # EDV67340, 26-392, with mutations: A26M, I28T,
Q334E, D335E, D348E, A385E)
MKTEEGKLVIWINGDKGYNGLAEVGKKFEKDTGIKVTVEHPDKLEEKFPQVAATGDGPDIIFWAHDRFGG

YAQSGLLAEITPDKAFQDKLYPFTWDAVRYNGKLIAYPIAVEALSLIYNKDLLPNPPKTWEEIPALDKELKA

KGKSALMFNLQEPYFTWPLIAADGGYAFKYENGKYDIKDVGVDNAGAKAGLTFLVDLIKNKHMNADTDYS

IAEAAFNKGETAMTINGPWAWSNIDTSKVNYGVTVLPTFKGQPSKPFVGVLSAGINAASPNKELAKEFLEN

YLLTDEGLEAVNKDKPLGAVALKSYEEELAKDPRIAATMENAQKGEIMPNIPQMSAFWYAVRTAVINAAS

GRQTVDEALKDAQTNSSSGSLSTPPTPSPSTPPTGLNDIFEAQKIEWHE

Validated Reactivity: MBP-C, derived from Accession # EDV67340, 26-392,
with mutations: A26M, Q334E, D335E, D348E, A385E, and Cterm additional
sequence from pMAL-c5X, and a C-term Cys
MKIEEGKLVIWINGDKGYNGLAEVGKKFEKDTGIKVTVEHPDKLEEKFPQVAATGDGPDIIFWAHDRFGG

YAQSGLLAEITPDKAFQDKLYPFTWDAVRYNGKLIAYPIAVEALSLIYNKDLLPNPPKTWEEIPALDKELKA

-continued

```
KGKSALMFNLQEPYFTWPLIAADGGYAFKYENGKYDIKDVGVDNAGAKAGLTFLVDLIKNKHMNADTDYS

IAEAAFNKGETAMTINGPWAWSNIDTSKVNYGVTVLPTFKGQPSKPFVGVLSAGINAASPNKELAKEFLEN

YLLTDEGLEAVNKDKPLGAVALKSYEEELVKDPRIAATMENAQKGEIMPNIPQMSAFWYAVRTAVINAAS

GRQTVDEALKDAQTNSSSNNNNNNNNNNLGIEGRC
```
Applications Tested
IP (FIG. 9C)

Additional MBP binders (FIG. 9D)
>P819C
```
MGSSHHHHHHNPSLIRSESWFLWIGNEANLLDGDDNTGVWYVVRWWGEKSLAGEFIGLDLGKEIKLDGI

RFVIGKNGGGSSDKWNKFKLEYSLDNESWTTIKEYDKTGAPAGKDVIEESFETPISAKYIRLTNLEQSWTN

LTFSEFAIVSDC
```

>P824C
```
MGSSHHHHHHNPSLIRSESWYPWVGNEANLLDGDDNTGVWYWHAWGAPSLAGEFIGLDLGKEIKLDGI

RFVIGKNGGGSSDKWNKFKLEYSLDNESWTTIKEYDKTGAPAGKDVIEESFETPISAKYIRLTNLEQIFAHL

TFSEFAIVSDC
```

3. Binders to IgG (mouse)
Primary Binder: P926LC
```
MGSSHHHHHHNPSLIRSESWRPFYGNEANLLDGDDNTGVWYNSKLHWRSLAGEFIGLDLGKEIKLDGIR

FVIGKNGGGSSDKWNKFKLEYSLDNESWTTIKEYDKTGAPAGKDVIEESFETPISAKYIRLTNLEQSSYGL

TFSEFAIVSDGGGGSGGGGSGGGC
```
Antigen: IgG, mouse (normal), biotinylated (Santa Cruz sc-2762)
Applications Tested
IP (FIG. 9E)

Additional mIgG binder (FIG. 10)
>P928
```
MKKTAIAIAVALAGFATVAQAAGSSHHHHHHNPSLIRSESWVRTIGNEANLLDGDDNTGVWYLPYKRAKS

LAGEFIGLDLGKEIKLDGIRFVIGKNGGGSSDKWNKFKLEYSLDNESWTTIKEYDKTGAPAGKDVIEESFET

PISAKYIRLTNLENIWTYLTFSEFAIVSDDYKDDDDKG
```

4. Binders to IgG (rabbit)
Primary Binder: P877LC
```
MGSSHHHHHHNPSLIRSESWYILGGNEANLLDGDDNTGVWYAPYWEVDSLAGEFIGLDLGKEIKLDGIRF

VIGKNGGGSSDKWNKFKLEYSLDNESWTTIKEYDKTGAPAGKDVIEESFETPISAKYIRLTNLEDRYFSLTF

SEFAIVSDGGGGSGGGGSGGGC
```
Antigen: IgG, rabbit anti-goat and anti-mouse IgG H&L, biotinylated
(Abcam ab6740, ab6727)
Applications Tested
IP (FIG. 9F)

Additional rIgG binder (FIG. 9F)
>P892LC
```
MGSSHHHHHHNPSLIRSESWYAEWGNEANLLDGDDNTGVWYVKFNQEPSLAGEFIGLDLGKEIKLDGIR

FVIGKNGGGSSDKWNKFKLEYSLDNESWTTIKEYDKTGAPAGKDVIEESFETPISAKYIRLTNLEADFVHLT

FSEFAIVSDGGGGSGGGGSGGGC
```

Binders to beta-D-galactosidase (BgaI)
Primary Binder: P895LC
```
MGSSHHHHHHNPSLIRSESWWTRYGNEANLLDGDDNTGVWYEKPYQVASLAGEFIGLDLGKEIKLDGIR

FVIGKNGGGSSDKWNKFKLEYSLDNESWTTIKEYDKTGAPAGKDVIEESFETPISAKYIRLTNLETYFSYLT

FSEFAIVSDGGGGSGGGGSGGGC
```

Antigen: beta-D-galactosidase; biotinylated (Rockland Chemical,
B000-17, Derived from Accession # NP_414878)
```
MTMITDSLAVVLQRRDWENPGVTQLNRLAAHPPFASWRNSEEARTDRPSQQLRSLNGEWRFAWFPAP

EAVPESWLECDLPEADTVVVPSNWQMHGYDAPIYTNVTYPITVNPPFVPTENPTGCYSLTFNVDESWLQ

EGQTRIIFDGVNSAFHLWCNGRWVGYGQDSRLPSEFDLSAFLRAGENRLAVMVLRWSDGSYLEDQDM

WRMSGIFRDVSLLHKPTTQISDFHVATRFNDDFSRAVLEAEVQMCGELRDYLRVTVSLWQGETQVASGT
```

-continued

APFGGEIIDERGGYADRVTLRLNVENPKLWSAEIPNLYRAVVELHTADGTLIEAEACDVGFREVRIENGLLL

LNGKPLLIRGVNRHEHHPLHGQVMDEQTMVQDILLMKQNNFNAVRCSHYPNHPLWYTLCDRYGLYVVD

EANIETHGMVPMNRLTDDPRWLPAMSERVTRMVQRDRNHPSVIIWSLGNESGHGANHDALYRWIKSVD

PSRPVQYEGGGADTTATDIICPMYARVDEDQPFPAVPKWSIKKWLSLPGETRPLILCEYAHAMGNSLGGF

AKYWQAFRQYPRLQGGFVWDWVDQSLIKYDENGNPWSAYGGDFGDTPNDRQFCMNGLVFADRTPHP

ALTEAKHQQQFFQFRLSGQTIEVTSEYLFRHSDNELLHWMVALDGKPLASGEVPLDVAPQGKQLIELPEL

PQPESAGQLWLTVRVVQPNATAWSEAGHISAWQQWRLAENLSVTLPAASHAIPHLTTSEMDFCIELGNK

RWQFNRQSGFLSQMWIGDKKQLLTPLRDQFTRAPLDNDIGVSEATRIDPNAWVERWKAAGHYQAEAAL

LQCTADTLADAVLITTAHAWQHQGKTLFISRKTYRIDGSGQMAITVDVEVASDTPHPARIGLNCQLAQVAE

RVNWLGLGPQENYPDRLTAACFDRWDLPLSDMYTPYVFPSENGLRCGTRELNYGPHQWRGDFQFNIS

RYSQQQLMETSHRHLLHAEEGTWLNIDGFHMGIGGDDSWSPSVSAEFQLSAGRYHYQLVWCQK
Validated Reactivity: N/A
Applications Tested
IP (FIG. 9G)

Additional BgaI binders (FIG. 9H)
>PC896
MCSSHHHHHHNPSLIRSESWQVYEGNEANLLDGDDNTGVWYKKAKNLASLAGEFIGLDLGKEIKLDGIRF

VIGKNGGGSSDKWNKFKLEYSLDNESWTTIKEYDKTGAPAGKDVIEESFETPISAKYIRLTNLESYFNFLTF

SEFAIVSD

>PC923
MCSSHHHHHHNPSLIRSESWQLIEGNEANLLDGDDNTGVWYFKDWHTASLAGEFIGLDLGKEIKLDGIRF

VIGKNGGGSSDKWNKFKLEYSLDNESWTTIKEYDKTGAPAGKDVIEESFETPISAKYIRLTNLESYFEYLTF

SEFAIVSD

Binders to NusA
Primary Binder: P955LC
MGSSHHHHHHNPSLIRSESWRYDFGNEANLLDGDDNTGVWYKKHHVKNSLAGEFIGLDLGKEIKLDGIR

FVIGKNGGGSSDKWNKFKLEYSLDNESWTTIKEYDKTGAPAGKDVIEESFETPISAKYIRLTNLEKKLTSLT

FSEFAIVSDGGGGSGGGGSGGGC

Antigen: NusA; biotinylated, N-term 6His tagged
(Derived from Accession number WP_044694313)
MGSSHHHHHHGTNKEILAVVEAVSNEKALPREKIFEALESALATATKKKY

EQEIDVRVQIDRKSGDFDTFRRWLVVDEVTQPTKEITLEAARYEDESLNL

GDYVEDQIESVTFDRITTQTAKQVIVQKVREAERAMVVDQFREHEGEIIT

GVVKKVNRDNISLDLGNNAEAVILREDMLPRENFRPGDRVRGVLYSVRPE

ARGAQLFVTRSKPEMLIELFRIEVPEIGEEVIEIKAAARDPGSRAKIAVK

TNDKRIDPVGACVGMRGARVQAVSTELGGERIDIVLWDDNPAQFVINAMA

PADVASIVVDEDKHTMDIAVEAGNLAQAIGRNGQNVRLASQLSGWELNVM

TVDDLQAKHQAEAHAAIDTFTKYLDIDEDFATVLVEEGFSTLEELAYVPM

KELLEIEGLDEPTVEALRERAKNALATIAQAQEESLGDNKPADDLLNLEG

VDRDLAFKLAARGVCTLEDLAEQGIDDLADIEGLTDEKAGALIMAARNIC

WFGDEAGTDYDIPTTENLYFQG

Validated Reactivity: NusA-GFPMut2
MGSSHHHHHHGTNKEILAVVEAVSNEKALPREKIFEALESALATATKKKYEQEIDVRVQIDRKSGDFDTFR

RWLVVDEVTQPTKEITLEAARYEDESLNLGDYVEDQIESVTFDRITTQTAKQVIVQKVREAERAMVVDQFR

EHEGEIITGVVKKVNRDNISLDLGNNAEAVILREDMLPRENFRPGDRVRGVLYSVRPEARGAQLFVTRSK

PEMLIELFRIEVPEIGEEVIEIKAAARDPGSRAKIAVKTNDKRIDPVGACVGMRGARVQAVSTELGGERIDIV

-continued

```
LWDDNPAQFVINAMAPADVASIVVDEDKHTMDIAVEAGNLAQAIGRNGQNVRLASQLSGWELNVMTVDD

LQAKHQAEAHAAIDTFTKYLDIDEDFATVLVEEGFSTLEELAYVPMKELLEIEGLDEPTVEALRERAKNALA

TIAQAQEESLGDNKPADDLLNLEGVDRDLAFKLAARGVCTLEDLAEQGIDDLADIEGLTDEKAGALIMAAR

NICWFGDEAGTDYDIPTTENLYFQGSKGEELFTGVVPILVELDGDVNGHKFSVSGEGEGDATYGKLTLKFI

CTTGKLPVPWPTLVTTFAYGLQCFARYPDHMKQHDFFKSAMPEGYVQERTIFFKDDGNYKTRAEVKFEG

DTLVNRIELKGIDFKEDGNILGHKLEYNYNSHNVYIMADKQKNGIKVNFKIRHNIEDGSVQLADHYQQNTPI

GDGPVLLPDNHYLSTQSALSKDPNEKRDHMVLLEFVTAAGITHGMDELYKIEGRGGKPIPNPLLGLDST
Applications Tested
IP (FIG. 9I)

Additional NusA binders (FIG. 9J)
>PC954
MGCSHHHHHHNPSLIRSESWAVLKGNEANLLDGDDNTGVWYANYKIQKSLAGEFIGLDLGKEIKLDGIRF

VIGKNGGGSSDKWNKFKLEYSLDNESWTTIKEYDKTGAPAGKDVIEESFETPISAKYIRLTNLEQAFLVLTF

SEFAIVSD

>PC956
MGCSHHHHHHNPSLIRSESWVFSIGNEANLLDGDDNTGVWYVAWWPETSLAGEFIGLDLGKEIKLDGIR

FVIGKNGGGSSDKWNKFKLEYSLDNESWTTIKEYDKTGAPAGKDVIEESFETPISAKYIRLTNLETYFHELT

FSEFAIVSD

Binders to Sumo
Primary Binder: P972LC
MGSSHHHHHHNPSLIRSESWEDIKGNEANLLDGDDNTGVWYFNEVFYESLAGEFIGLDLGKEIKLDGIRF

VIGKNGGGSSDKWNKFKLEYSLDNESWTTIKEYDKTGAPAGKDVIEESFETPISAKYIRLTNLEDKILFLTF

SEFAIVSDGGGGSGGGGSGGGC

Antigen: SUMO; biotinylated, 6His tagged Saccharomyces cerevisiae SUMO
protein SMT3 (Derived from Accession number BAO66634)
MGSSHHHHHHMSDSEVNQEAKPEVKPEVKPETHINLKVSDGSSEIFFKIKKTTPLRRLME

AFAKRQGKEMDSLRFLYDGIRIQADQTPEDLDMEDNDIIEAHREQIGGHMASMTGGQQ

Validated Reactivity: SUMO-mCherry
MSDSEVNQEAKPEVKPEVKPETHINLKVSDGSSEIFFKIKKTTPLRRLMEAFAKRQGKEMDSLRFLYDGIR

IQADQTPEDLDMEDNDIIEAHREQIGGSSGLVPRGSHMVSKGEEDNMAIIKEFMRFKVHMEGSVNGHEFE

IEGEGEGRPYEGTQTAKLKVTKGGPLPFAWDILSPQFMYGSKAYVKHPADIPDYLKLSFPEGFKWERVM

NFEDGGVVTVTQDSSLQDGEFIYKVKLRGTNFPSDGPVMQKKTMGWEASSERMYPEDGALKGEIKQRL

KLKDGGHYDAEVKTTYKAKKPVQLPGAYNVNIKLDITSHNEDYTIVEQYERAEGRHSTGGMDELYK
Applications Tested
IP (FIG. 9K)

Additional Sumo binders (FIG. 11)
>P971
MKKTAIAIAVALAGFATVAQAAGSSHHHHHHNPSLIRSESWAAVYGNEANLLDGDDNTGVWYFNDDVYE

SLAGEFIGLDLGKEIKLDGIRFVIGKNGGGSSDKWNKFKLEYSLDNESWTTIKEYDKTGAPAGKDVIEESF

ETPISAKYIRLTNLEHEAIWLTFSEFAIVSDDYKDDDDKG

>P973
MKKTAIAIAVALAGFATVAQAAGSSHHHHHHNPSLIRSESWTVEYGNEANLLDGDDNTGVWYKKWWDA

KSLAGEFIGLDLGKEIKLDGIRFVIGKNGGGSSDKWNKFKLEYSLDNESWTTIKEYDKTGAPAGKDVIEES

FETPISAKYIRLTNLEWLFDELTFSEFAIVSDDYKDDDDKG

Binders to thioredoxin
Primary Binder: P962LC
MGSSHHHHHHNPSLIRSESWHTYNGNEANLLDGDDNTGVWYNNNSWFSSLAGEFIGLDLGKEIKLDGIR

FVIGKNGGGSSDKWNKFKLEYSLDNESWTTIKEYDKTGAPAGKDVIEESFETPISAKYIRLTNLEAKNNLTF

SEFAIVSDGGGGSGGGGSGGGC
```

```
Antigen: Thioredoxin; biotinylated, N-term 6His (Excellgen Cat# EG-5,
derivative of Accession #AAN83133)
MKIEMHHHHHHAMGSDKIIHLTDDSFDTDVLKADGAILVDFWAEWCGPCKMIAPILDEIADEYQGKLTVAK

LNIDQNPGTAPKYGIRGIPTLLLFKNGEVAATKVGALSKGQLKEFLDANLA

Validated Reactivity: Thioredoxin-GFPMut2
MGSSHHHHHHAMGSDKIIHLTDDSFDTDVLKADGAILVDFWAEWCGPCKMIAPILDEIADEYQGKLTVAKL

NIDQNPGTAPKYGIRGIPTLLLFKNGEVAATKVGALSKGQLKEFLDANLALYFQGSKGEELFTGVVPILVEL

DGDVNGHKFSVSGEGEGDATYGKLTLKFICTTGKLPVPWPTLVTTFAYGLQCFARYPDHMKQHDFFKSA

MPEGYVQERTIFFKDDGNYKTRAEVKFEGDTLVNRIELKGIDFKEDGNILGHKLEYNYNSHNVYIMADKQK

NGIKVNFKIRHNIEDGSVQLADHYWNTPIGDGPVLLPDNHYLSTQSALSKDPNEKRDHMVLLEFVTAAGI

THGMDELYKIEGRGGKPIPNPLLGLDST
Applications Tested
IP (FIG. 9L)

Additional Trx binders (FIG. 9M)
>PC961
MGCSHHHHHHNPSLIRSESWPVYGNEANLLDGDDNTGVWYYSSGTYFSLAGEFIGLDLGKEIKLDGIRFV

IGKNGGGSSDKWNKFKLEYSLDNESWTTIKEYDKTGAPAGKDVIEESFETPISAKYIRLTNLELKYYGLTFS

EFAIVSD

>PC966
MGCSHHHHHHNPSLIRSESWYIGVGNEANLLDGDDNTGVWYEKYHLYVSLAGEFIGLDLGKEIKLDGIRF

VIGKNGGGSSDKWNKFKLEYSLDNESWTTIKEYDKTGAPAGKDVIEESFETPISAKYIRLTNLEVGRKSLT

FSEFAIVSD

Binders to Neutravidin
Primary Binder: P975LC
MGSSHHHHHHNPSLIRSESWWIRSGNEANLLDGDDNTGVWYDNLYWYRSLAGEFIGLDLGKEIKLDGIR

FVIGKNGGGSSDKWNKFKLEYSLDNESWTTIKEYDKTGAPAGKDVIEESFETPISAKYIRLTNLENKYGILT

FSEFAIVSDGGGGSGGGGSGGGC
Antigen: Neutravidin (deglycosylated avidin from egg-whites): Neutravidin
coated magnetic particles (Spherotech NVM-20-05)
Validated Reactivity: Neutravidin (Pierce Neutravidin Protein Cat #31000)
Applications Tested
IP (FIG. 9N)

Additional Neutravidin binders (FIG. 9O)
>PC977
MGCSHHHHHHNPSLIRSESWRRWSGNEANLLDGDDNTGVWYVTWPFSESLAGEFIGLDLGKEIKLDGIR

FVIGKNGGGSSDKWNKFKLEYSLDNESWTTIKEYDKTGAPAGKDVIEESFETPISAKYIRLTNLENINKWLT

FSEFAIVSD

>PC979
MGCSHHHHHHNPSLIRSESWYAIFGNEANLLDGDDNTGVWYHSRNYYKSLAGEFIGLDLGKEIKLDGIRF

VIGKNGGGSSDKWNKFKLEYSLDNESWTTIKEYDKTGAPAGKDVIEESFETPISAKYIRLTNLEHLWGHLT

FSEFAIVSD

Binders to Streptavidin
Primary Binder: P982LC
MGSSHHHHHHNPSLIRSESWGVIAGNEANLLDGDDNTGVWYTKSNNHLSLAGEFIGLDLGKEIKLDGIRF

VIGKNGGGSSDKWNKFKLEYSLDNESWTTIKEYDKTGAPAGKDVIEESFETPISAKYIRLTNLEAVFFNLTF

SEFAIVSDGGGGSGGGGSGGGC

Antigen: Streptavidin; recombinant (Dynabeads MyOne Streptavidin T1
(Invitrogen))
Validated Reactivity: Streptavidin (Streptavidin isolated from
Streptomyces avidinii. NEB N7021S)
Applications Tested
IP (FIG. 9P)
```

```
Binders to V5 epitope
Primary Binder: P997LC
MGSSHHHHHHNPSLIRSESWVKYFGNEANLLDGDDNTGVWYFWHTASSLAGEFIGLDLGKEIKLDGIRF

VIGKNGGGSSDKWNKFKLEYSLDNESWTTIKEYDKTGAPAGKDVIEESFETPISAKYIRLTNLEQYINILTFS

EFAIVSDGGGGSGGGGSGGGC

Antigen: V5 peptide (CGKPIPNPLLGLDST)
Validated Reactivity: 6His-GFPMut2-V5, 6His-GFPMut2-3xV5
Applications Tested
IP (FIG. 9Q)
Additional V5 binder (FIG. 12)
>P999
MKKTAIAIAVALAGFATVAQAAGSSHHHHHHNPSLIRSESWTKIRGNEANLLDGDDNTGVWYALTFKNIHE

WYWVVSSLAGEFIGLDLGKEIKLDGIRFVIGKNGGGSSDKWNKFKLEYSLDNESWTTIKEYDKTGAPAGK

DVIEESFETPISAKYIRLTNLEDYIYDLTFSEFAIVSDG

Binders to mCherry
Primary Binder: P1034LC
MGSSHHHHHHNPSLIRSESWVGSKGNEANLLDGDDNTGVWYPWFPKAIFFKNREFGSLAGEFIGLDLGK

EIKLDGIRFVIGKNGGGSSDKWNKFKLEYSLDNESWTTIKEYDKTGAPAGKDVIEESFETPISAKYIRLTNL

EYVSVILTFSEFAIVSDGGGGSGGGGSGGGC

Antigen: mCherry; biotinylated, N-term 6 His (Derived from Accession #
AHH01498)
MGSSHHHHHHSSGLVPRGSHMVSKGEEDNMAIIKEFMRFKVHMEGSVNGHEFEIEGEGEGRPYEGTQT

AKLKVTKGGPLPFAWDILSPQFMYGSKAYVKHPADIPDYLKLSFPEGFKWERVMNFEDGGVVTVTQDSS

LQDGEFIYKVKLRGTNFPSDGPVMQKKTMGWEASSERMYPEDGALKGEIKQRLKLKDGGHYDAEVKTT

YKAKKPVQLPGAYNVNIKLDITSHNEDYTIVEQYERAEGRHSTGGMDELYK

Validated Reactivity: SUMO-mCherry
MSDSEVNQEAKPEVKPEVKPETHINLKVSDGSSEIFFKIKKTTPLRRLMEAFAKRQGKEMDSLRFLYDGIR

IQADQTPEDLDMEDNDIIEAHREQIGGSSGLVPRGSHMVSKGEEDNMAIIKEFMRFKVHMEGSVNGHEFE

IEGEGEGRPYEGTQTAKLKVTKGGPLPFAWDILSPQFMYGSKAYVKHPADIPDYLKLSFPEGFKWERVM

NFEDGGVVTVTQDSSLQDGEFIYKVKLRGTNFPSDGPVMQKKTMGWEASSERMYPEDGALKGEIKQRL

KLKDGGHYDAEVKTTYKAKKPVQLPGAYNVNIKLDITSHNEDYTIVEQYERAEGRHSTGGMDELYK
Applications Tested
IP (FIG. 9R)

Binders to cmyc
Primary Binder: P1021LC
MGSSHHHHHHNPSLIRSESWDTTAGNEANLLDGDDNTGVWYITGWVHRRYVWETQLSLAGEFIGLDLG

KEIKLDGIRFVIGKNGGGSSDKWNKFKLEYSLDNESWTTIKEYDKTGAPAGKDVIEESFETPISAKYIRLTN

MENINKWLTFSEFAIVSDGGGGSGGGGSGGGC

Antigen: cmyc epitope tag (CEQKLISEEDL)

Validated reactivity: GFPMut2-3X-cmyc
MGSSHHHHHHSKGEELFTGVVPILVELDGDVNGHKFSVSGEGEGDATYGKLTLKFICTTGKLPVPWPTL

VTTFAYGLQCFARYPDHMKQHDFFKSAMPEGYVQERTIFFKDDGNYKTRAEVKFEGDTLVNRIELKGIDF

KEDGNILGHKLEYNYNSHNVYIMADKQKNGIKVNFKIRHNIEDGSVQLADHYQQNTPIGDGPVLLPDNHYL

STQSALSKDPNEKRDHMVLLEFVTAAGITHGMDELYKIEGRGEQKLISEEDLGEQKLISEEDLGEQKLISE

EDL
Applications Tested
IP (FIG. 9S)

Binders to Flag
Primary Binder: P1015C
MGSSHHHHHHNPSLIRSESWAHIWGNEANLLDGDDNTGVWYWVGVSLAGEFIGLDLGKEIKLDGIRFVIG

KNGGGSSDKWNKFKLEYSLDNESWTTIKEYDKTGAPAGKDVIEESFETPISAKYIRLTNLEFGTGSLTFSE
```

-continued

FAIVSDC

Antigen: Flag tag (CDYKDDDDK)

Validated reactivity: VHH-flag
QVQLVQSGGGLVQPGGSLRLSCAASDYGQQGYTTPWTFMSWVRQAPGKALEWIGYIHHSGSTNYNPS

LKSRVTISRDNSKNTLYLQMNTLRAEDTAMYYCARGNLAIRYWGQGTLVTVSSSGQAGHHHHHHGDYK

DDDDKG
Applications Tested
IP (FIG. 9T)

Example 5. Generation of Library 3

Library 3 is a variation of Library 2, in which Loop W was elongated to 15 total residues and the Flag tag C-terminal to the CBM was removed, while keeping the same surrounding constant regions. To remove the Flag-tag, 200 ng of Library 2 phagemid was amplified with overlapping primers 517 F and 518 R at final concentrations of 0.4 uM in a total reaction volume of 1 ml using 2× CloneAmp HiFi PCR premix. The reaction was cycled 20 times at 98° C. for 10 sec, 65° C. for 10 sec and 72° C. for 30 sec. The amplicon was gel purified on a 1.1% agarose gel and purified using a Qiaquick gel extraction kit (Qiagen). The purified DNA was Gibson cloned using the overlapping regions of the primers to generate the library phagemid with no flag-tag by incubating 1.35 ug of DNA with 135 ul Gibson Assembly Master Mix in a total reaction volume of 270 ul for 15 min at 50° C., and subsequently purified using Minelute PCRprep columns. This DNA was used as template to elongate Loop W by amplifying 400 ng of it with phosphoramidite trimer primer 512T F (which contains 15 random codons in Loop W) and primer 523 R at final concentrations of 0.4 uM with 500 ul of 2× CloneAmp HiFi PCR premix in a total reaction volume of 1 ml and cycled 15× at 98° C. for 10 sec, 65° C. for 10 sec, and 72° C. for 30 sec. The amplicon was gel purified on a 1% agarose gel using 8 Qiaquick gel purification columns, then concentrated using 2 PCR Miniprep columns. This DNA, which contains overlapping end regions, was circularized by Gibson cloning 5 ug in a total reaction volume of 1 ml for 15 min at 50° C., after which the enzyme was removed and the DNA purified by PCRprep minelute columns. The DNA was desalted using a nitrocellulose membrane (VSWP 0.025 um membrane) on ddH2O for 30 min, changing the water and repeating, yielding a final phagemid DNA concentration of 124 ng/ul. This DNA was used to electroporate electrocompetent TG1 cells as described above, yielding a library with a theoretical diversity of 1.24e10 CFU. The library was panned and screened as described above, and binders derived from this library were produced and characterized as described above.

OTHER EMBODIMENTS

Various modifications and variations of the described methods and compositions of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications mentioned in this specification are herein incorporated by reference to the same extent as if each independent publication was specifically and individually incorporated by reference.

The invention claimed is:

1. An affinity scaffold, said affinity scaffold having the following formula:

CR1-V-CR2-W-CR3-Z-CR4, wherein:
said V, W, and Z are each independently not present or comprise one or more amino acids; and
said CR1-CR4 have amino acid sequences that have at least 95% identity to SEQ ID NOs: 2, 4, 6, and 8, respectively;
wherein said affinity scaffold does not comprise the sequence of SEQ ID NO: 1.

2. An affinity scaffold, said affinity scaffold having the following formula:

CR1-V-CR2-W-CR5-X-CR6-Y-CR7-Z-CR4, wherein:
said V, W, X, Y, and Z are each independently not present or comprise one or more amino; and
said CR1, CR2, CR5, CR6, CR7, and CR4 have amino acid sequences that have at least 95% identity to SEQ ID NOs: 2, 4, 9, 11, 13, and 8, respectively;
wherein said affinity scaffold does not comprise the sequence of SEQ ID NO: 1.

3. The affinity scaffold of claim 1, wherein said CR1-CR4 have the amino acid sequences of SEQ ID NOs: 2, 4, 6, and 8, respectively.

4. An isolated cDNA sequence encoding the affinity scaffold of claim 1 in an expression-conducive context.

5. The affinity scaffold of claim 2, wherein said CR1, CR2, CR5, CR6, CR7, and CR4 have the amino acid sequences of SEQ ID NOs: 2, 4, 9, 11, 13, and 8, respectively.

* * * * *

SEQUENCE LISTING

```
<160> NUMBER OF SEQ ID NOS: 113

<210> SEQ ID NO 1
<211> LENGTH: 140
<212> TYPE: PRT
<213> ORGANISM: Artificial Sequence
<220> FEATURE:
<223> OTHER INFORMATION: Synthetic Construct

<400> SEQUENCE: 1

Asn Pro Ser Leu Ile Arg Ser Glu Ser Trp Gln Val Tyr Glu Gly Asn
1               5                   10                  15

Glu Ala Asn Leu Leu Asp Gly Asp Asn Thr Gly Val Trp Tyr Lys
            20                  25                  30

Thr Leu Asn Gly Asp Thr Ser Leu Ala Gly Glu Phe Ile Gly Leu Asp
        35                  40                  45

Leu Gly Lys Glu Ile Lys Leu Asp Gly Ile Arg Phe Val Ile Gly Lys
    50                  55                  60

Asn Gly Gly Gly Ser Ser Asp Lys Trp Asn Lys Phe Lys Leu Glu Tyr
65                  70                  75                  80
```

```
Ser Leu Asp Asn Glu Ser Trp Thr Thr Ile Lys Glu Tyr Asp Lys Thr
                85                  90                  95

Gly Ala Pro Ala Gly Lys Asp Val Ile Glu Ser Phe Glu Thr Pro
            100                 105                 110

Ile Ser Ala Lys Tyr Ile Arg Leu Thr Asn Met Glu Asn Ile Asn Lys
        115                 120                 125

Trp Leu Thr Phe Ser Glu Phe Ala Ile Val Ser Asp
    130                 135                 140

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Asn Pro Ser Leu Ile Arg Ser Glu Ser Trp
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Gln Val Tyr Glu
1

<210> SEQ ID NO 4
<211> LENGTH: 17
<212> TYPE: PRT
<213> ORGANISM: Artificial Sequence
<220> FEATURE:
<223> OTHER INFORMATION: Synthetic Construct

<400> SEQUENCE: 4

Gly Asn Glu Ala Asn Leu Leu Asp Gly Asp Asn Thr Gly Val Trp
1               5                   10                  15

Tyr

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Lys Thr Leu Asn Gly Asp Thr
1               5

<210> SEQ ID NO 6
<211> LENGTH: 86
<212> TYPE: PRT
<213> ORGANISM: Artificial Sequence
<220> FEATURE:
<223> OTHER INFORMATION: Synthetic Construct

<400> SEQUENCE: 6

Ser Leu Ala Gly Glu Phe Ile Gly Leu Asp Leu Gly Lys Glu Ile Lys
1               5                   10                  15
```

Leu Asp Gly Ile Arg Phe Val Ile Gly Lys Asn Gly Gly Ser Ser
            20                  25                  30

Asp Lys Trp Asn Lys Phe Lys Leu Glu Tyr Ser Leu Asp Asn Glu Ser
        35                  40                  45

Trp Thr Thr Ile Lys Glu Tyr Asp Lys Thr Gly Ala Pro Ala Gly Lys
 50                  55                  60

Asp Val Ile Glu Glu Ser Phe Glu Thr Pro Ile Ser Ala Lys Tyr Ile
65                  70                  75                  80

Arg Leu Thr Asn Met Glu
                85

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Asn Ile Asn Lys Trp
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Leu Thr Phe Ser Glu Phe Ala Ile Val Ser Asp
1               5                   10

<210> SEQ ID NO 9
<211> LENGTH: 27
<212> TYPE: PRT
<213> ORGANISM: Artificial Sequence
<220> FEATURE:
<223> OTHER INFORMATION: Synthetic Construct

<400> SEQUENCE: 9

Ser Leu Ala Gly Glu Phe Ile Gly Leu Asp Leu Gly Lys Glu Ile Lys
1               5                   10                  15

Leu Asp Gly Ile Arg Phe Val Ile Gly Lys Asn
            20                  25

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Gly Gly Gly Ser Ser Asp Lys
1               5

<210> SEQ ID NO 11
<211> LENGTH: 23
<212> TYPE: PRT
<213> ORGANISM: Artificial Sequence
<220> FEATURE:
<223> OTHER INFORMATION: Synthetic Construct

```
<400> SEQUENCE: 11

Trp Asn Lys Phe Lys Leu Glu Tyr Ser Leu Asp Asn Glu Ser Trp Thr
1               5                   10                  15

Thr Ile Lys Glu Tyr Asp Lys
            20

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Thr Gly Ala Pro Ala Gly
1               5

<210> SEQ ID NO 13
<211> LENGTH: 23
<212> TYPE: PRT
<213> ORGANISM: Artificial Sequence
<220> FEATURE:
<223> OTHER INFORMATION: Synthetic Construct

<400> SEQUENCE: 13

Lys Asp Val Ile Glu Glu Ser Phe Glu Thr Pro Ile Ser Ala Lys Tyr
1               5                   10                  15

Ile Arg Leu Thr Asn Met Glu
            20

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct

<400> SEQUENCE: 14

Gln Leu Asn Asn
1

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

Val Ala Asn Val Gly Thr Gln
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Thr Ser Gly Trp Gly
1               5

<210> SEQ ID NO 17
<211> LENGTH: 140
```

```
<212> TYPE: PRT
<213> ORGANISM: Artificial Sequence
<220> FEATURE:
<223> OTHER INFORMATION: Synthetic Construct

<400> SEQUENCE: 17

Asn Pro Ser Leu Ile Arg Ser Glu Ser Trp Phe Leu Trp Ile Gly Asn
1               5                   10                  15

Glu Ala Asn Leu Leu Asp Gly Asp Asn Thr Gly Val Trp Tyr Trp
            20                  25                  30

Arg Trp Trp Gly Glu Lys Ser Leu Ala Gly Glu Phe Ile Gly Leu Asp
            35                  40                  45

Leu Gly Lys Glu Ile Lys Leu Asp Gly Ile Arg Phe Val Ile Gly Lys
        50                  55                  60

Asn Gly Gly Gly Ser Ser Asp Lys Trp Asn Lys Phe Lys Leu Glu Tyr
65                  70                  75                  80

Ser Leu Asp Asn Glu Ser Trp Thr Thr Ile Lys Glu Tyr Asp Lys Thr
                85                  90                  95

Gly Ala Pro Ala Gly Lys Asp Val Ile Glu Glu Ser Phe Glu Thr Pro
            100                 105                 110

Ile Ser Ala Lys Tyr Ile Arg Leu Thr Asn Leu Glu Gln Ser Trp Thr
        115                 120                 125

Asn Leu Thr Phe Ser Glu Phe Ala Ile Val Ser Asp
    130                 135                 140

<210> SEQ ID NO 18
<211> LENGTH: 140
<212> TYPE: PRT
<213> ORGANISM: Artificial Sequence
<220> FEATURE:
<223> OTHER INFORMATION: Synthetic Construct

<400> SEQUENCE: 18

Asn Pro Ser Leu Ile Arg Ser Glu Ser Trp Gln Leu Asn Asn Gly Asn
1               5                   10                  15

Glu Ala Asn Leu Leu Asp Gly Asp Asn Thr Gly Val Trp Tyr Val
            20                  25                  30

Ala Asn Val Gly Thr Gln Ser Leu Ala Gly Glu Phe Ile Gly Leu Asp
        35                  40                  45

Leu Gly Lys Glu Ile Lys Leu Asp Gly Ile Arg Phe Val Ile Gly Lys
        50                  55                  60

Asn Gly Gly Gly Ser Ser Asp Lys Trp Asn Lys Phe Lys Leu Glu Tyr
65                  70                  75                  80

Ser Leu Asp Asn Glu Ser Trp Thr Thr Ile Lys Glu Tyr Asp Lys Thr
                85                  90                  95

Gly Ala Pro Ala Gly Lys Asp Val Ile Glu Glu Ser Phe Glu Thr Pro
            100                 105                 110

Ile Ser Ala Lys Tyr Ile Arg Leu Thr Asn Leu Glu Thr Ser Gly Trp
        115                 120                 125

Gly Leu Thr Phe Ser Glu Phe Ala Ile Val Ser Asp
    130                 135                 140

<210> SEQ ID NO 19
<211> LENGTH: 140
<212> TYPE: PRT
<213> ORGANISM: Artificial Sequence
<220> FEATURE:
<223> OTHER INFORMATION: Synthetic Construct
```

<400> SEQUENCE: 19

Asn Pro Ser Leu Ile Arg Ser Glu Ser Trp Tyr Pro Trp Val Gly Asn
1               5                   10                  15

Glu Ala Asn Leu Leu Asp Gly Asp Asn Thr Gly Val Trp Tyr Trp
            20                  25                  30

His Ala Trp Gly Ala Pro Ser Leu Ala Gly Glu Phe Ile Gly Leu Asp
        35                  40                  45

Leu Gly Lys Glu Ile Lys Leu Asp Gly Ile Arg Phe Val Ile Gly Lys
    50                  55                  60

Asn Gly Gly Ser Ser Asp Lys Trp Asn Lys Phe Lys Leu Glu Tyr
65              70                  75                  80

Ser Leu Asp Asn Glu Ser Trp Thr Thr Ile Lys Glu Tyr Asp Lys Thr
                85                  90                  95

Gly Ala Pro Ala Gly Lys Asp Val Ile Glu Glu Ser Phe Glu Thr Pro
            100                 105                 110

Ile Ser Ala Lys Tyr Ile Arg Leu Thr Asn Leu Glu Gln Ile Phe Ala
        115                 120                 125

His Leu Thr Phe Ser Glu Phe Ala Ile Val Ser Asp
    130                 135                 140

<210> SEQ ID NO 20
<211> LENGTH: 140
<212> TYPE: PRT
<213> ORGANISM: Artificial Sequence
<220> FEATURE:
<223> OTHER INFORMATION: Synthetic Construct

<400> SEQUENCE: 20

Asn Pro Ser Leu Ile Arg Ser Glu Ser Trp Thr Val Tyr Glu Gly Asn
1               5                   10                  15

Glu Ala Asn Leu Leu Asp Gly Asp Asn Thr Gly Val Trp Tyr Lys
            20                  25                  30

Tyr Val Pro Ser Thr Asp Ser Leu Ala Gly Glu Phe Ile Gly Leu Asp
        35                  40                  45

Leu Gly Lys Glu Ile Lys Leu Asp Gly Ile Arg Phe Val Ile Gly Lys
    50                  55                  60

Asn Val Phe Phe Arg Pro Val Ile Trp Asn Lys Phe Lys Leu Glu Tyr
65              70                  75                  80

Ser Leu Asp Asn Glu Ser Trp Thr Thr Ile Lys Glu Tyr Asp Lys Phe
                85                  90                  95

Leu Pro Asp Val Ala Lys Asp Val Ile Glu Glu Ser Phe Glu Thr Pro
            100                 105                 110

Ile Ser Ala Lys Tyr Ile Arg Leu Thr Asn Met Glu Gly Tyr Gly Ile
        115                 120                 125

Ser Leu Thr Phe Ser Glu Phe Ala Ile Val Ser Asp
    130                 135                 140

<210> SEQ ID NO 21
<211> LENGTH: 140
<212> TYPE: PRT
<213> ORGANISM: Artificial Sequence
<220> FEATURE:
<223> OTHER INFORMATION: Synthetic Construct

<400> SEQUENCE: 21

Asn Pro Ser Leu Ile Arg Ser Glu Ser Trp Ile Val Tyr Glu Gly Asn
1               5                   10                  15

-continued

Glu Ala Asn Leu Leu Asp Gly Asp Asn Thr Gly Val Trp Tyr Lys
            20                  25                  30

Pro Leu Asp Phe Pro Phe Ser Leu Ala Gly Glu Phe Ile Gly Leu Asp
        35                  40                  45

Leu Gly Lys Glu Ile Lys Leu Asp Gly Ile Arg Phe Val Ile Gly Lys
    50                  55                  60

Asn Ala Ser Cys Gly Phe Asp Ala Trp Asn Lys Phe Lys Leu Glu Tyr
65                  70                  75                  80

Ser Leu Asp Asn Glu Ser Trp Thr Thr Ile Lys Glu Tyr Asp Lys Ile
                85                  90                  95

Ser Pro Ser Tyr Ser Lys Asp Val Ile Glu Glu Ser Phe Glu Thr Pro
            100                 105                 110

Ile Ser Ala Lys Tyr Ile Arg Leu Thr Asn Met Glu Ile Cys Val Cys
        115                 120                 125

Phe Leu Thr Phe Ser Glu Phe Ala Ile Val Ser Asp
    130                 135                 140

<210> SEQ ID NO 22
<211> LENGTH: 140
<212> TYPE: PRT
<213> ORGANISM: Artificial Sequence
<220> FEATURE:
<223> OTHER INFORMATION: Synthetic Construct

<400> SEQUENCE: 22

Asn Pro Ser Leu Ile Arg Ser Glu Ser Trp Cys Val Tyr Glu Gly Asn
1               5                   10                  15

Glu Ala Asn Leu Leu Asp Gly Asp Asn Thr Gly Val Trp Tyr Lys
            20                  25                  30

Leu Cys Pro Ser Pro Phe Ser Leu Ala Gly Glu Phe Ile Gly Leu Asp
        35                  40                  45

Leu Gly Lys Glu Ile Lys Leu Asp Gly Ile Arg Phe Val Ile Gly Lys
    50                  55                  60

Asn Gly Tyr Leu Gly Ser Asp Ala Trp Asn Lys Phe Lys Leu Glu Tyr
65                  70                  75                  80

Ser Leu Asp Asn Glu Ser Trp Thr Thr Ile Lys Glu Tyr Asp Lys Asn
                85                  90                  95

His Asn Ser Thr His Lys Asp Val Ile Glu Glu Ser Phe Glu Thr Pro
            100                 105                 110

Ile Ser Ala Lys Tyr Ile Arg Leu Thr Asn Met Glu Phe Cys Leu Ser
        115                 120                 125

Asp Leu Thr Phe Ser Glu Phe Ala Ile Val Ser Asp
    130                 135                 140

<210> SEQ ID NO 23
<211> LENGTH: 21
<212> TYPE: PRT
<213> ORGANISM: Artificial Sequence
<220> FEATURE:
<223> OTHER INFORMATION: Synthetic Construct

<400> SEQUENCE: 23

Val Tyr Glu Gly Asn Glu Ala Asn Leu Leu Asp Gly Asp Asn Thr
1               5                   10                  15

Gly Val Trp Tyr Lys
            20

<210> SEQ ID NO 24

```
<211> LENGTH: 15
<212> TYPE: PRT
<213> ORGANISM: Artificial Sequence
<220> FEATURE:
<223> OTHER INFORMATION: Synthetic Construct

<400> SEQUENCE: 24

Gly Leu Asn Asp Ile Phe Glu Ala Gln Lys Ile Glu Trp His Glu
1               5                   10                  15

<210> SEQ ID NO 25
<211> LENGTH: 26
<212> TYPE: PRT
<213> ORGANISM: Artificial Sequence
<220> FEATURE:
<223> OTHER INFORMATION: Synthetic Construct

<400> SEQUENCE: 25

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 26
<211> LENGTH: 6
<212> TYPE: PRT
<213> ORGANISM: Artificial Sequence
<220> FEATURE:
<223> OTHER INFORMATION: Synthetic Construct

<400> SEQUENCE: 26

Glu Glu Glu Glu Glu Glu
1               5

<210> SEQ ID NO 27
<211> LENGTH: 13
<212> TYPE: PRT
<213> ORGANISM: Artificial Sequence
<220> FEATURE:
<223> OTHER INFORMATION: Synthetic Construct

<400> SEQUENCE: 27

Gly Ala Pro Val Pro Tyr Pro Asp Pro Leu Glu Pro Arg
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Synthetic Construct

<400> SEQUENCE: 28

Asp Tyr Lys Asp Asp Asp Asp Lys
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Tyr Pro Tyr Asp Val Pro Asp Tyr Ala
1               5
```

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct

<400> SEQUENCE: 30

His His His His His His
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic Construct

<400> SEQUENCE: 31

Glu Gln Lys Leu Ile Ser Glu Glu Asp Leu
1               5                   10

<210> SEQ ID NO 32
<211> LENGTH: 15
<212> TYPE: PRT
<213> ORGANISM: Artificial Sequence
<220> FEATURE:
<223> OTHER INFORMATION: Synthetic Construct

<400> SEQUENCE: 32

Lys Glu Thr Ala Ala Ala Lys Phe Glu Arg Gln His Met Asp Ser
1               5                   10                  15

<210> SEQ ID NO 33
<211> LENGTH: 38
<212> TYPE: PRT
<213> ORGANISM: Artificial Sequence
<220> FEATURE:
<223> OTHER INFORMATION: Synthetic Construct

<400> SEQUENCE: 33

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 34
<211> LENGTH: 13
<212> TYPE: PRT
<213> ORGANISM: Artificial Sequence
<220> FEATURE:
<223> OTHER INFORMATION: Synthetic Construct

<400> SEQUENCE: 34

Ser Leu Ala Glu Leu Leu Asn Ala Gly Leu Gly Gly Ser
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 35

Thr Gln Asp Pro Ser Arg Val Gly
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Trp Ser His Pro Gln Phe Glu Lys
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic Construct

<400> SEQUENCE: 37

Cys Cys Pro Gly Cys Cys
1               5

<210> SEQ ID NO 38
<211> LENGTH: 14
<212> TYPE: PRT
<213> ORGANISM: Artificial Sequence
<220> FEATURE:
<223> OTHER INFORMATION: Synthetic Construct

<400> SEQUENCE: 38

Gly Lys Pro Ile Pro Asn Pro Leu Leu Gly Leu Asp Ser Thr
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic Construct

<400> SEQUENCE: 39

Tyr Thr Asp Ile Glu Met Asn Arg Leu Gly Lys
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct

<400> SEQUENCE: 40

Asp Leu Tyr Asp Asp Asp Asp Lys
1               5

<210> SEQ ID NO 41
<211> LENGTH: 16
<212> TYPE: PRT
<213> ORGANISM: Artificial Sequence
<220> FEATURE:
<223> OTHER INFORMATION: Synthetic Construct

<400> SEQUENCE: 41
```

Thr Asp Lys Asp Met Thr Ile Thr Phe Thr Asn Lys Lys Asp Ala Glu
1               5                   10                  15

<210> SEQ ID NO 42
<211> LENGTH: 13
<212> TYPE: PRT
<213> ORGANISM: Artificial Sequence
<220> FEATURE:
<223> OTHER INFORMATION: Synthetic Construct

<400> SEQUENCE: 42

Ala His Ile Val Met Val Asp Ala Tyr Lys Pro Thr Lys
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Synthetic Construct

<400> SEQUENCE: 43

Gly Gly Gly Gly Ser Gly Gly Gly Gly Ser Gly Gly Gly Cys
1               5                   10

<210> SEQ ID NO 44
<211> LENGTH: 6
<212> TYPE: PRT
<213> ORGANISM: Artificial Sequence
<220> FEATURE:
<223> OTHER INFORMATION: Synthetic Construct

<400> SEQUENCE: 44

Thr Leu Asn Gly Asp Thr
1               5

<210> SEQ ID NO 45
<211> LENGTH: 164
<212> TYPE: PRT
<213> ORGANISM: Artificial Sequence
<220> FEATURE:
<223> OTHER INFORMATION: Synthetic Construct

<400> SEQUENCE: 45

Met Gly Ser Ser His His His His His His Asn Pro Ser Leu Ile Arg
1               5                   10                  15

Ser Glu Ser Trp Asp Glu Trp Phe Gly Asn Glu Ala Asn Leu Leu Asp
            20                  25                  30

Gly Asp Asp Asn Thr Gly Val Trp Tyr Val Ser Phe Ala Asp Asn Tyr
        35                  40                  45

Ser Leu Ala Gly Glu Phe Ile Gly Leu Asp Leu Gly Lys Glu Ile Lys
    50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
            100                 105                 110

Asp Val Ile Glu Glu Ser Phe Glu Thr Pro Ile Ser Ala Lys Tyr Ile
        115                 120                 125

Arg Leu Thr Asn Leu Glu Asn Arg Trp Ser Tyr Leu Thr Phe Ser Glu
    130                 135                 140

Phe Ala Ile Val Ser Asp Gly Gly Gly Ser Gly Gly Gly Ser
145                 150                 155                 160

Gly Gly Gly Cys

<210> SEQ ID NO 46
<211> LENGTH: 263
<212> TYPE: PRT
<213> ORGANISM: Artificial Sequence
<220> FEATURE:
<223> OTHER INFORMATION: Synthetic Construct

<400> SEQUENCE: 46

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ala Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Gly Gly
225                 230                 235                 240

Gly Leu Asn Asp Ile Phe Glu Ala Gln Lys Ile Glu Trp His Glu Gly
                245                 250                 255

Ala His His His His His His
            260

<210> SEQ ID NO 47
<211> LENGTH: 238
<212> TYPE: PRT
<213> ORGANISM: Artificial Sequence
<220> FEATURE:
<223> OTHER INFORMATION: Synthetic Construct

<400> SEQUENCE: 47

Met Ser Lys Gly Glu Glu Leu Phe Thr Gly Val Val Pro Ile Leu Val
1               5                   10                  15

```
Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
 50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 48
<211> LENGTH: 151
<212> TYPE: PRT
<213> ORGANISM: Artificial Sequence
<220> FEATURE:
<223> OTHER INFORMATION: Synthetic Construct

<400> SEQUENCE: 48

Met Gly Ser Ser His His His His His His Asn Pro Ser Leu Ile Arg
  1               5                  10                  15

Ser Glu Ser Trp Ala Arg Trp Ala Gly Asn Glu Ala Asn Leu Leu Asp
             20                  25                  30

Gly Asp Asp Asn Thr Gly Val Trp Tyr Trp Ala Lys Lys Asn Asn Ile
         35                  40                  45

Ser Leu Ala Gly Glu Phe Ile Gly Leu Asp Leu Gly Lys Glu Ile Lys
 50                  55                  60

Leu Asp Gly Ile Arg Phe Val Ile Gly Lys Asn Gly Gly Ser Ser
 65                  70                  75                  80

Asp Lys Trp Asn Lys Phe Lys Leu Glu Tyr Ser Leu Asp Asn Glu Ser
                 85                  90                  95

Trp Thr Thr Ile Lys Glu Tyr Asp Lys Thr Gly Ala Pro Ala Gly Lys
            100                 105                 110

Asp Val Ile Glu Glu Ser Phe Glu Thr Pro Ile Ser Ala Lys Tyr Ile
        115                 120                 125

Arg Leu Thr Asn Leu Glu Thr Thr Phe Gly Gly Leu Thr Phe Ser Glu
130                 135                 140
```

Phe Ala Ile Val Ser Asp Cys
145                 150

<210> SEQ ID NO 49
<211> LENGTH: 151
<212> TYPE: PRT
<213> ORGANISM: Artificial Sequence
<220> FEATURE:
<223> OTHER INFORMATION: Synthetic Construct

<400> SEQUENCE: 49

Met Gly Ser Ser His His His His His Asn Pro Ser Leu Ile Arg
1               5                   10                  15

Ser Glu Ser Trp Ala Thr Trp His Gly Asn Glu Ala Asn Leu Leu Asp
                20                  25                  30

Gly Asp Asn Thr Gly Val Trp Tyr Trp Asp Asp Tyr Asn Asn
            35                  40                  45

Ser Leu Ala Gly Glu Phe Ile Gly Leu Asp Leu Gly Lys Glu Ile Lys
50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
                100                 105                 110

Asp Val Ile Glu Glu Ser Phe Glu Thr Pro Ile Ser Ala Lys Tyr Ile
                115                 120                 125

Arg Leu Thr Asn Leu Glu Pro Gln Trp Gly Gly Leu Thr Phe Ser Glu
                130                 135                 140

Phe Ala Ile Val Ser Asp Cys
145                 150

<210> SEQ ID NO 50
<211> LENGTH: 151
<212> TYPE: PRT
<213> ORGANISM: Artificial Sequence
<220> FEATURE:
<223> OTHER INFORMATION: Synthetic Construct

<400> SEQUENCE: 50

Met Gly Ser Ser His His His His His Asn Pro Ser Leu Ile Arg
1               5                   10                  15

Ser Glu Ser Trp Ser Ala Trp Ile Gly Asn Glu Ala Asn Leu Leu Asp
                20                  25                  30

Gly Asp Asp Asn Thr Gly Val Trp Tyr Tyr Asn Tyr Ala Lys Asn Trp
            35                  40                  45

Ser Leu Ala Gly Glu Phe Ile Gly Leu Asp Leu Gly Lys Glu Ile Lys
50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
                100                 105                 110

Asp Val Ile Glu Glu Ser Phe Glu Thr Pro Ile Ser Ala Lys Tyr Ile
                115                 120                 125

Arg Leu Thr Asn Leu Glu Glu Lys Trp Ser Tyr Leu Thr Phe Ser Glu

Phe Ala Ile Val Ser Asp Cys
145                 150

<210> SEQ ID NO 51
<211> LENGTH: 151
<212> TYPE: PRT
<213> ORGANISM: Artificial Sequence
<220> FEATURE:
<223> OTHER INFORMATION: Synthetic Construct

<400> SEQUENCE: 51

Met Gly Ser Ser His His His His His Asn Pro Ser Leu Ile Arg
1               5                   10                  15

Ser Glu Ser Trp Gln Leu Asn Asn Gly Asn Glu Ala Asn Leu Leu Asp
                20                  25                  30

Gly Asp Asp Asn Thr Gly Val Trp Tyr Val Ala Asn Val Gly Thr Gln
            35                  40                  45

Ser Leu Ala Gly Glu Phe Ile Gly Leu Asp Leu Gly Lys Glu Ile Lys
        50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
                100                 105                 110

Asp Val Ile Glu Glu Ser Phe Glu Thr Pro Ile Ser Ala Lys Tyr Ile
            115                 120                 125

Arg Leu Thr Asn Leu Glu Thr Ser Gly Trp Gly Leu Thr Phe Ser Glu
        130                 135                 140

Phe Ala Ile Val Ser Asp Cys
145                 150

<210> SEQ ID NO 52
<211> LENGTH: 402
<212> TYPE: PRT
<213> ORGANISM: Artificial Sequence
<220> FEATURE:
<223> OTHER INFORMATION: Synthetic Construct

<400> SEQUENCE: 52

Met Lys Thr Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

```
Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
                195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
        355                 360                 365

Ser Ser Ser Gly Ser Leu Ser Thr Pro Pro Thr Pro Ser Pro Ser Thr
370                 375                 380

Pro Pro Thr Gly Leu Asn Asp Ile Phe Glu Ala Gln Lys Ile Glu Trp
385                 390                 395                 400

His Glu

<210> SEQ ID NO 53
<211> LENGTH: 388
<212> TYPE: PRT
<213> ORGANISM: Artificial Sequence
<220> FEATURE:
<223> OTHER INFORMATION: Synthetic Construct

<400> SEQUENCE: 53

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
```

```
            85                  90                  95
Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
            130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
                195                 200                 205

Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
                275                 280                 285

Glu Gly Leu Glu Ala Val Asn Lys Asp Lys Pro Leu Gly Ala Val Ala
            290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
            370                 375                 380

Glu Gly Arg Cys
385

<210> SEQ ID NO 54
<211> LENGTH: 151
<212> TYPE: PRT
<213> ORGANISM: Artificial Sequence
<220> FEATURE:
<223> OTHER INFORMATION: Synthetic Construct

<400> SEQUENCE: 54

Met Gly Ser Ser His His His His His Asn Pro Ser Leu Ile Arg
1               5                   10                  15

Ser Glu Ser Trp Phe Leu Trp Ile Gly Asn Glu Ala Asn Leu Leu Asp
                20                  25                  30

Gly Asp Asp Asn Thr Gly Val Trp Tyr Trp Arg Trp Trp Gly Glu Lys
            35                  40                  45

Ser Leu Ala Gly Glu Phe Ile Gly Leu Asp Leu Gly Lys Glu Ile Lys
```

```
Leu Asp Gly Ile Arg Phe Val Ile Gly Lys Asn Gly Gly Ser Ser
 65                  70                  75                  80

Asp Lys Trp Asn Lys Phe Lys Leu Glu Tyr Ser Leu Asp Asn Glu Ser
                 85                  90                  95

Trp Thr Thr Ile Lys Glu Tyr Asp Lys Thr Gly Ala Pro Ala Gly Lys
                100                 105                 110

Asp Val Ile Glu Glu Ser Phe Glu Thr Pro Ile Ser Ala Lys Tyr Ile
            115                 120                 125

Arg Leu Thr Asn Leu Glu Gln Ser Trp Thr Asn Leu Thr Phe Ser Glu
        130                 135                 140

Phe Ala Ile Val Ser Asp Cys
145                 150

<210> SEQ ID NO 55
<211> LENGTH: 151
<212> TYPE: PRT
<213> ORGANISM: Artificial Sequence
<220> FEATURE:
<223> OTHER INFORMATION: Synthetic Construct

<400> SEQUENCE: 55

Met Gly Ser Ser His His His His His Asn Pro Ser Leu Ile Arg
 1               5                  10                  15

Ser Glu Ser Trp Tyr Pro Trp Val Gly Asn Glu Ala Asn Leu Leu Asp
                 20                  25                  30

Gly Asp Asp Asn Thr Gly Val Trp Tyr Trp His Ala Trp Gly Ala Pro
             35                  40                  45

Ser Leu Ala Gly Glu Phe Ile Gly Leu Asp Leu Gly Lys Glu Ile Lys
         50                  55                  60

Leu Asp Gly Ile Arg Phe Val Ile Gly Lys Asn Gly Gly Ser Ser
 65                  70                  75                  80

Asp Lys Trp Asn Lys Phe Lys Leu Glu Tyr Ser Leu Asp Asn Glu Ser
                 85                  90                  95

Trp Thr Thr Ile Lys Glu Tyr Asp Lys Thr Gly Ala Pro Ala Gly Lys
                100                 105                 110

Asp Val Ile Glu Glu Ser Phe Glu Thr Pro Ile Ser Ala Lys Tyr Ile
            115                 120                 125

Arg Leu Thr Asn Leu Glu Gln Ile Phe Ala His Leu Thr Phe Ser Glu
        130                 135                 140

Phe Ala Ile Val Ser Asp Cys
145                 150

<210> SEQ ID NO 56
<211> LENGTH: 164
<212> TYPE: PRT
<213> ORGANISM: Artificial Sequence
<220> FEATURE:
<223> OTHER INFORMATION: Synthetic Construct

<400> SEQUENCE: 56

Met Gly Ser Ser His His His His His Asn Pro Ser Leu Ile Arg
 1               5                  10                  15

Ser Glu Ser Trp Arg Pro Phe Tyr Gly Asn Glu Ala Asn Leu Leu Asp
                 20                  25                  30

Gly Asp Asp Asn Thr Gly Val Trp Tyr Asn Ser Lys Leu His Trp Arg
             35                  40                  45
```

```
Ser Leu Ala Gly Glu Phe Ile Gly Leu Asp Leu Gly Lys Glu Ile Lys
 50                  55                  60

Leu Asp Gly Ile Arg Phe Val Ile Gly Lys Asn Gly Gly Ser Ser
 65                  70                  75                  80

Asp Lys Trp Asn Lys Phe Lys Leu Glu Tyr Ser Leu Asp Asn Glu Ser
                 85                  90                  95

Trp Thr Thr Ile Lys Glu Tyr Asp Lys Thr Gly Ala Pro Ala Gly Lys
                100                 105                 110

Asp Val Ile Glu Glu Ser Phe Glu Thr Pro Ile Ser Ala Lys Tyr Ile
                115                 120                 125

Arg Leu Thr Asn Leu Glu Gln Ser Ser Tyr Gly Leu Thr Phe Ser Glu
            130                 135                 140

Phe Ala Ile Val Ser Asp Gly Gly Gly Ser Gly Gly Gly Ser
145                 150                 155                 160

Gly Gly Gly Cys
```

<210> SEQ ID NO 57
<211> LENGTH: 180
<212> TYPE: PRT
<213> ORGANISM: Artificial Sequence
<220> FEATURE:
<223> OTHER INFORMATION: Synthetic Construct

<400> SEQUENCE: 57

```
Met Lys Lys Thr Ala Ile Ala Ile Ala Val Ala Leu Ala Gly Phe Ala
 1               5                  10                  15

Thr Val Ala Gln Ala Ala Gly Ser Ser His His His His His His Asn
                20                  25                  30

Pro Ser Leu Ile Arg Ser Glu Ser Trp Val Arg Thr Ile Gly Asn Glu
             35                  40                  45

Ala Asn Leu Leu Asp Gly Asp Asp Asn Thr Gly Val Trp Tyr Leu Pro
 50                  55                  60

Tyr Lys Arg Ala Lys Ser Leu Ala Gly Glu Phe Ile Gly Leu Asp Leu
 65                  70                  75                  80

Gly Lys Glu Ile Lys Leu Asp Gly Ile Arg Phe Val Ile Gly Lys Asn
                 85                  90                  95

Gly Gly Gly Ser Ser Asp Lys Trp Asn Lys Phe Lys Leu Glu Tyr Ser
                100                 105                 110

Leu Asp Asn Glu Ser Trp Thr Thr Ile Lys Glu Tyr Asp Lys Thr Gly
            115                 120                 125

Ala Pro Ala Gly Lys Asp Val Ile Glu Glu Ser Phe Glu Thr Pro Ile
130                 135                 140

Ser Ala Lys Tyr Ile Arg Leu Thr Asn Leu Glu Asn Ile Trp Thr Tyr
145                 150                 155                 160

Leu Thr Phe Ser Glu Phe Ala Ile Val Ser Asp Tyr Lys Asp Asp
                165                 170                 175

Asp Asp Lys Gly
            180
```

<210> SEQ ID NO 58
<211> LENGTH: 164
<212> TYPE: PRT
<213> ORGANISM: Artificial Sequence
<220> FEATURE:
<223> OTHER INFORMATION: Synthetic Construct

<400> SEQUENCE: 58

Met Gly Ser Ser His His His His His Asn Pro Ser Leu Ile Arg
1               5                   10                  15

Ser Glu Ser Trp Tyr Ile Leu Gly Gly Asn Glu Ala Asn Leu Leu Asp
                20                  25                  30

Gly Asp Asp Asn Thr Gly Val Trp Tyr Ala Pro Tyr Trp Glu Val Asp
            35                  40                  45

Ser Leu Ala Gly Glu Phe Ile Gly Leu Asp Leu Gly Lys Glu Ile Lys
50                  55                  60

Leu Asp Gly Ile Arg Phe Val Ile Gly Lys Asn Gly Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
                100                 105                 110

Asp Val Ile Glu Glu Ser Phe Glu Thr Pro Ile Ser Ala Lys Tyr Ile
            115                 120                 125

Arg Leu Thr Asn Leu Glu Asp Arg Tyr Phe Ser Leu Thr Phe Ser Glu
        130                 135                 140

Phe Ala Ile Val Ser Asp Gly Gly Gly Ser Gly Gly Gly Gly Ser
145                 150                 155                 160

Gly Gly Gly Cys

<210> SEQ ID NO 59
<211> LENGTH: 164
<212> TYPE: PRT
<213> ORGANISM: Artificial Sequence
<220> FEATURE:
<223> OTHER INFORMATION: Synthetic Construct

<400> SEQUENCE: 59

Met Gly Ser Ser His His His His His Asn Pro Ser Leu Ile Arg
1               5                   10                  15

Ser Glu Ser Trp Tyr Ala Glu Trp Gly Asn Glu Ala Asn Leu Leu Asp
                20                  25                  30

Gly Asp Asp Asn Thr Gly Val Trp Tyr Val Lys Phe Asn Gln Glu Pro
            35                  40                  45

Ser Leu Ala Gly Glu Phe Ile Gly Leu Asp Leu Gly Lys Glu Ile Lys
50                  55                  60

Leu Asp Gly Ile Arg Phe Val Ile Gly Lys Asn Gly Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
                100                 105                 110

Asp Val Ile Glu Glu Ser Phe Glu Thr Pro Ile Ser Ala Lys Tyr Ile
            115                 120                 125

Arg Leu Thr Asn Leu Glu Ala Asp Phe Val His Leu Thr Phe Ser Glu
        130                 135                 140

Phe Ala Ile Val Ser Asp Gly Gly Gly Ser Gly Gly Gly Gly Ser
145                 150                 155                 160

Gly Gly Gly Cys

<210> SEQ ID NO 60
<211> LENGTH: 164
<212> TYPE: PRT
<213> ORGANISM: Artificial Sequence -continued

```
<220> FEATURE:
<223> OTHER INFORMATION: Synthetic Construct

<400> SEQUENCE: 60

Met Gly Ser Ser His His His His His His Asn Pro Ser Leu Ile Arg
1               5                   10                  15

Ser Glu Ser Trp Trp Thr Arg Tyr Gly Asn Glu Ala Asn Leu Leu Asp
            20                  25                  30

Gly Asp Asp Asn Thr Gly Val Trp Tyr Glu Lys Pro Tyr Gln Val Ala
        35                  40                  45

Ser Leu Ala Gly Glu Phe Ile Gly Leu Asp Leu Gly Lys Glu Ile Lys
    50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
            100                 105                 110

Asp Val Ile Glu Glu Ser Phe Glu Thr Pro Ile Ser Ala Lys Tyr Ile
        115                 120                 125

Arg Leu Thr Asn Leu Glu Thr Tyr Phe Ser Tyr Leu Thr Phe Ser Glu
    130                 135                 140

Phe Ala Ile Val Ser Asp Gly Gly Gly Ser Gly Gly Gly Gly Ser
145                 150                 155                 160

Gly Gly Gly Cys

<210> SEQ ID NO 61
<211> LENGTH: 1024
<212> TYPE: PRT
<213> ORGANISM: Artificial Sequence
<220> FEATURE:
<223> OTHER INFORMATION: Synthetic Construct

<400> SEQUENCE: 61

Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Trp Leu Glu Cys Asp Leu Pro
65                  70                  75                  80

Glu Ala Asp Thr Val Val Val Pro Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Asn Pro Thr Gly Cys Tyr Ser Leu Thr Phe
        115                 120                 125

Asn Val Asp Glu Ser Trp Leu Gln Glu Gly Gln Thr Arg Ile Ile Phe
    130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175
```

```
Phe Leu Arg Ala Gly Glu Asn Arg Leu Ala Val Met Val Leu Arg Trp
            180                 185                 190

Ser Asp Gly Ser Tyr Leu Glu Asp Gln Asp Met Trp Arg Met Ser Gly
            195                 200                 205

Ile Phe Arg Asp Val Ser Leu Leu His Lys Pro Thr Thr Gln Ile Ser
210                 215                 220

Asp Phe His Val Ala Thr Arg Phe Asn Asp Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
            260                 265                 270

Ala Pro Phe Gly Gly Glu Ile Ile Asp Glu Arg Gly Gly Tyr Ala Asp
            275                 280                 285

Arg Val Thr Leu Arg Leu Asn Val Glu Asn Pro Lys Leu Trp Ser Ala
290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Leu Asn Gly Lys Pro Leu Leu Ile
            340                 345                 350

Arg Gly Val Asn Arg His Glu His His Pro Leu His Gly Gln Val Met
            355                 360                 365

Asp Glu Gln Thr Met Val Gln Asp Ile Leu Leu Met Lys Gln Asn Asn
            370                 375                 380

Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
                405                 410                 415

Glu Thr His Gly Met Val Pro Met Asn Arg Leu Thr Asp Asp Pro Arg
            420                 425                 430

Trp Leu Pro Ala Met Ser Glu Arg Val Thr Arg Met Val Gln Arg Asp
            435                 440                 445

Arg Asn His Pro Ser Val Ile Ile Trp Ser Leu Gly Asn Glu Ser Gly
450                 455                 460

His Gly Ala Asn His Asp Ala Leu Tyr Arg Trp Ile Lys Ser Val Asp
465                 470                 475                 480

Pro Ser Arg Pro Val Gln Tyr Glu Gly Gly Gly Ala Asp Thr Thr Ala
                485                 490                 495

Thr Asp Ile Ile Cys Pro Met Tyr Ala Arg Val Asp Glu Asp Gln Pro
            500                 505                 510

Phe Pro Ala Val Pro Lys Trp Ser Ile Lys Lys Trp Leu Ser Leu Pro
            515                 520                 525

Gly Glu Thr Arg Pro Leu Ile Leu Cys Glu Tyr Ala His Ala Met Gly
            530                 535                 540

Asn Ser Leu Gly Gly Phe Ala Lys Tyr Trp Gln Ala Phe Arg Gln Tyr
545                 550                 555                 560

Pro Arg Leu Gln Gly Gly Phe Val Trp Asp Trp Val Asp Gln Ser Leu
                565                 570                 575

Ile Lys Tyr Asp Glu Asn Gly Asn Pro Trp Ser Ala Tyr Gly Gly Asp
            580                 585                 590
```

-continued

Phe Gly Asp Thr Pro Asn Asp Arg Gln Phe Cys Met Asn Gly Leu Val
            595                 600                 605

Phe Ala Asp Arg Thr Pro His Pro Ala Leu Thr Glu Ala Lys His Gln
        610                 615                 620

Gln Gln Phe Phe Gln Phe Arg Leu Ser Gly Gln Thr Ile Glu Val Thr
625                 630                 635                 640

Ser Glu Tyr Leu Phe Arg His Ser Asp Asn Glu Leu Leu His Trp Met
                645                 650                 655

Val Ala Leu Asp Gly Lys Pro Leu Ala Ser Gly Glu Val Pro Leu Asp
            660                 665                 670

Val Ala Pro Gln Gly Lys Gln Leu Ile Glu Leu Pro Glu Leu Pro Gln
        675                 680                 685

Pro Glu Ser Ala Gly Gln Leu Trp Leu Thr Val Arg Val Val Gln Pro
    690                 695                 700

Asn Ala Thr Ala Trp Ser Glu Ala Gly His Ile Ser Ala Trp Gln Gln
705                 710                 715                 720

Trp Arg Leu Ala Glu Asn Leu Ser Val Thr Leu Pro Ala Ala Ser His
                725                 730                 735

Ala Ile Pro His Leu Thr Thr Ser Glu Met Asp Phe Cys Ile Glu Leu
            740                 745                 750

Gly Asn Lys Arg Trp Gln Phe Asn Arg Gln Ser Gly Phe Leu Ser Gln
        755                 760                 765

Met Trp Ile Gly Asp Lys Lys Gln Leu Leu Thr Pro Leu Arg Asp Gln
770                 775                 780

Phe Thr Arg Ala Pro Leu Asp Asn Asp Ile Gly Val Ser Glu Ala Thr
785                 790                 795                 800

Arg Ile Asp Pro Asn Ala Trp Val Glu Arg Trp Lys Ala Ala Gly His
                805                 810                 815

Tyr Gln Ala Glu Ala Ala Leu Leu Gln Cys Thr Ala Asp Thr Leu Ala
            820                 825                 830

Asp Ala Val Leu Ile Thr Thr Ala His Ala Trp Gln His Gln Gly Lys
        835                 840                 845

Thr Leu Phe Ile Ser Arg Lys Thr Tyr Arg Ile Asp Gly Ser Gly Gln
    850                 855                 860

Met Ala Ile Thr Val Asp Val Glu Val Ala Ser Asp Thr Pro His Pro
865                 870                 875                 880

Ala Arg Ile Gly Leu Asn Cys Gln Leu Ala Gln Val Ala Glu Arg Val
                885                 890                 895

Asn Trp Leu Gly Leu Gly Pro Gln Glu Asn Tyr Pro Asp Arg Leu Thr
            900                 905                 910

Ala Ala Cys Phe Asp Arg Trp Asp Leu Pro Leu Ser Asp Met Tyr Thr
        915                 920                 925

Pro Tyr Val Phe Pro Ser Glu Asn Gly Leu Arg Cys Gly Thr Arg Glu
    930                 935                 940

Leu Asn Tyr Gly Pro His Gln Trp Arg Gly Asp Phe Gln Phe Asn Ile
945                 950                 955                 960

Ser Arg Tyr Ser Gln Gln Gln Leu Met Glu Thr Ser His Arg His Leu
                965                 970                 975

Leu His Ala Glu Glu Gly Thr Trp Leu Asn Ile Asp Gly Phe His Met
            980                 985                 990

Gly Ile Gly Gly Asp Asp Ser Trp Ser Pro Ser Val Ser Ala Glu Phe
        995                 1000                1005

Gln Leu Ser Ala Gly Arg Tyr His Tyr Gln Leu Val Trp Cys Gln

```
                    1010                1015                1020
Lys

<210> SEQ ID NO 62
<211> LENGTH: 150
<212> TYPE: PRT
<213> ORGANISM: Artificial Sequence
<220> FEATURE:
<223> OTHER INFORMATION: Synthetic Construct

<400> SEQUENCE: 62

Met Cys Ser Ser His His His His His His Asn Pro Ser Leu Ile Arg
1               5                   10                  15

Ser Glu Ser Trp Gln Val Tyr Glu Gly Asn Glu Ala Asn Leu Leu Asp
            20                  25                  30

Gly Asp Asp Asn Thr Gly Val Trp Tyr Lys Lys Ala Lys Asn Leu Ala
        35                  40                  45

Ser Leu Ala Gly Glu Phe Ile Gly Leu Asp Leu Gly Lys Glu Ile Lys
50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
            100                 105                 110

Asp Val Ile Glu Glu Ser Phe Glu Thr Pro Ile Ser Ala Lys Tyr Ile
        115                 120                 125

Arg Leu Thr Asn Leu Glu Ser Tyr Phe Asn Phe Leu Thr Phe Ser Glu
    130                 135                 140

Phe Ala Ile Val Ser Asp
145                 150

<210> SEQ ID NO 63
<211> LENGTH: 150
<212> TYPE: PRT
<213> ORGANISM: Artificial Sequence
<220> FEATURE:
<223> OTHER INFORMATION: Synthetic Construct

<400> SEQUENCE: 63

Met Cys Ser Ser His His His His His His Asn Pro Ser Leu Ile Arg
1               5                   10                  15

Ser Glu Ser Trp Gln Leu Ile Glu Gly Asn Glu Ala Asn Leu Leu Asp
            20                  25                  30

Gly Asp Asp Asn Thr Gly Val Trp Tyr Phe Lys Asp Trp His Thr Ala
        35                  40                  45

Ser Leu Ala Gly Glu Phe Ile Gly Leu Asp Leu Gly Lys Glu Ile Lys
50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
            100                 105                 110

Asp Val Ile Glu Glu Ser Phe Glu Thr Pro Ile Ser Ala Lys Tyr Ile
        115                 120                 125

Arg Leu Thr Asn Leu Glu Ser Tyr Phe Glu Tyr Leu Thr Phe Ser Glu
```

Phe Ala Ile Val Ser Asp
145             150

<210> SEQ ID NO 64
<211> LENGTH: 164
<212> TYPE: PRT
<213> ORGANISM: Artificial Sequence
<220> FEATURE:
<223> OTHER INFORMATION: Synthetic Construct

<400> SEQUENCE: 64

Met Gly Ser Ser His His His His His Asn Pro Ser Leu Ile Arg
1               5                   10                  15

Ser Glu Ser Trp Arg Tyr Asp Phe Gly Asn Glu Ala Asn Leu Leu Asp
                20                  25                  30

Gly Asp Asp Asn Thr Gly Val Trp Tyr Lys Lys His His Val Lys Asn
            35                  40                  45

Ser Leu Ala Gly Glu Phe Ile Gly Leu Asp Leu Gly Lys Glu Ile Lys
        50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
            100                 105                 110

Asp Val Ile Glu Glu Ser Phe Glu Thr Pro Ile Ser Ala Lys Tyr Ile
        115                 120                 125

Arg Leu Thr Asn Leu Glu Lys Lys Leu Thr Ser Leu Thr Phe Ser Glu
    130                 135                 140

Phe Ala Ile Val Ser Asp Gly Gly Gly Ser Gly Gly Gly Gly Ser
145                 150                 155                 160

Gly Gly Gly Cys

<210> SEQ ID NO 65
<211> LENGTH: 522
<212> TYPE: PRT
<213> ORGANISM: Artificial Sequence
<220> FEATURE:
<223> OTHER INFORMATION: Synthetic Construct

<400> SEQUENCE: 65

Met Gly Ser Ser His His His His His Gly Thr Asn Lys Glu Ile
1               5                   10                  15

Leu Ala Val Val Glu Ala Val Ser Asn Glu Lys Ala Leu Pro Arg Glu
                20                  25                  30

Lys Ile Phe Glu Ala Leu Glu Ser Ala Leu Ala Thr Ala Thr Lys Lys
        35                  40                  45

Lys Tyr Glu Gln Glu Ile Asp Val Arg Val Gln Ile Asp Arg Lys Ser
    50                  55                  60

Gly Asp Phe Asp Thr Phe Arg Arg Trp Leu Val Val Asp Glu Val Thr
65                  70                  75                  80

Gln Pro Thr Lys Glu Ile Thr Leu Glu Ala Ala Arg Tyr Glu Asp Glu
                85                  90                  95

Ser Leu Asn Leu Gly Asp Tyr Val Glu Asp Gln Ile Glu Ser Val Thr
            100                 105                 110

Phe Asp Arg Ile Thr Thr Gln Thr Ala Lys Gln Val Ile Val Gln Lys

Val Arg Glu Ala Glu Arg Ala Met Val Val Asp Gln Phe Arg Glu His
130                 135                 140

Glu Gly Glu Ile Ile Thr Gly Val Val Lys Val Asn Arg Asp Asn
145                 150                 155                 160

Ile Ser Leu Asp Leu Gly Asn Asn Ala Glu Ala Val Ile Leu Arg Glu
                165                 170                 175

Asp Met Leu Pro Arg Glu Asn Phe Arg Pro Gly Asp Arg Val Arg Gly
            180                 185                 190

Val Leu Tyr Ser Val Arg Pro Glu Ala Arg Gly Ala Gln Leu Phe Val
        195                 200                 205

Thr Arg Ser Lys Pro Glu Met Leu Ile Glu Leu Phe Arg Ile Glu Val
210                 215                 220

Pro Glu Ile Gly Glu Val Ile Glu Ile Lys Ala Ala Ala Arg Asp
225                 230                 235                 240

Pro Gly Ser Arg Ala Lys Ile Ala Val Lys Thr Asn Asp Lys Arg Ile
                245                 250                 255

Asp Pro Val Gly Ala Cys Val Gly Met Arg Gly Ala Arg Val Gln Ala
            260                 265                 270

Val Ser Thr Glu Leu Gly Gly Glu Arg Ile Asp Ile Val Leu Trp Asp
        275                 280                 285

Asp Asn Pro Ala Gln Phe Val Ile Asn Ala Met Ala Pro Ala Asp Val
290                 295                 300

Ala Ser Ile Val Val Asp Glu Asp Lys His Thr Met Asp Ile Ala Val
305                 310                 315                 320

Glu Ala Gly Asn Leu Ala Gln Ala Ile Gly Arg Asn Gly Gln Asn Val
                325                 330                 335

Arg Leu Ala Ser Gln Leu Ser Gly Trp Glu Leu Asn Val Met Thr Val
            340                 345                 350

Asp Asp Leu Gln Ala Lys His Gln Ala Glu Ala His Ala Ala Ile Asp
        355                 360                 365

Thr Phe Thr Lys Tyr Leu Asp Ile Asp Glu Asp Phe Ala Thr Val Leu
370                 375                 380

Val Glu Glu Gly Phe Ser Thr Leu Glu Glu Leu Ala Tyr Val Pro Met
385                 390                 395                 400

Lys Glu Leu Leu Glu Ile Glu Gly Leu Asp Glu Pro Thr Val Glu Ala
                405                 410                 415

Leu Arg Glu Arg Ala Lys Asn Ala Leu Ala Thr Ile Ala Gln Ala Gln
            420                 425                 430

Glu Glu Ser Leu Gly Asp Asn Lys Pro Ala Asp Asp Leu Leu Asn Leu
        435                 440                 445

Glu Gly Val Asp Arg Asp Leu Ala Phe Lys Leu Ala Ala Arg Gly Val
450                 455                 460

Cys Thr Leu Glu Asp Leu Ala Glu Gln Gly Ile Asp Asp Leu Ala Asp
465                 470                 475                 480

Ile Glu Gly Leu Thr Asp Glu Lys Ala Gly Ala Leu Ile Met Ala Ala
                485                 490                 495

Arg Asn Ile Cys Trp Phe Gly Asp Glu Ala Gly Thr Tyr Asp Ile
            500                 505                 510

Pro Thr Thr Glu Asn Leu Tyr Phe Gln Gly
        515                 520

<210> SEQ ID NO 66

<211> LENGTH: 778
<212> TYPE: PRT
<213> ORGANISM: Artificial Sequence
<220> FEATURE:
<223> OTHER INFORMATION: Synthetic Construct

<400> SEQUENCE: 66

Met Gly Ser Ser His His His His His His Gly Thr Asn Lys Glu Ile
1               5                   10                  15

Leu Ala Val Val Glu Ala Val Ser Asn Glu Lys Ala Leu Pro Arg Glu
            20                  25                  30

Lys Ile Phe Glu Ala Leu Glu Ser Ala Leu Ala Thr Ala Thr Lys Lys
        35                  40                  45

Lys Tyr Glu Gln Glu Ile Asp Val Arg Val Gln Ile Asp Arg Lys Ser
    50                  55                  60

Gly Asp Phe Asp Thr Phe Arg Arg Trp Leu Val Val Asp Glu Val Thr
65                  70                  75                  80

Gln Pro Thr Lys Glu Ile Thr Leu Glu Ala Ala Arg Tyr Glu Asp Glu
                85                  90                  95

Ser Leu Asn Leu Gly Asp Tyr Val Glu Asp Gln Ile Glu Ser Val Thr
            100                 105                 110

Phe Asp Arg Ile Thr Thr Gln Thr Ala Lys Gln Val Ile Val Gln Lys
        115                 120                 125

Val Arg Glu Ala Glu Arg Ala Met Val Val Asp Gln Phe Arg Glu His
130                 135                 140

Glu Gly Glu Ile Ile Thr Gly Val Val Lys Lys Val Asn Arg Asp Asn
145                 150                 155                 160

Ile Ser Leu Asp Leu Gly Asn Asn Ala Glu Ala Val Ile Leu Arg Glu
                165                 170                 175

Asp Met Leu Pro Arg Glu Asn Phe Arg Pro Gly Asp Arg Val Arg Gly
            180                 185                 190

Val Leu Tyr Ser Val Arg Pro Glu Ala Arg Gly Ala Gln Leu Phe Val
        195                 200                 205

Thr Arg Ser Lys Pro Glu Met Leu Ile Glu Leu Phe Arg Ile Glu Val
    210                 215                 220

Pro Glu Ile Gly Glu Glu Val Ile Glu Ile Lys Ala Ala Ala Arg Asp
225                 230                 235                 240

Pro Gly Ser Arg Ala Lys Ile Ala Val Lys Thr Asn Asp Lys Arg Ile
                245                 250                 255

Asp Pro Val Gly Ala Cys Val Gly Met Arg Gly Ala Arg Val Gln Ala
            260                 265                 270

Val Ser Thr Glu Leu Gly Gly Glu Arg Ile Asp Ile Val Leu Trp Asp
        275                 280                 285

Asp Asn Pro Ala Gln Phe Val Ile Asn Ala Met Ala Pro Ala Asp Val
    290                 295                 300

Ala Ser Ile Val Val Asp Glu Asp Lys His Thr Met Asp Ile Ala Val
305                 310                 315                 320

Glu Ala Gly Asn Leu Ala Gln Ala Ile Gly Arg Asn Gly Gln Asn Val
                325                 330                 335

Arg Leu Ala Ser Gln Leu Ser Gly Trp Glu Leu Asn Val Met Thr Val
            340                 345                 350

Asp Asp Leu Gln Ala Lys His Gln Ala Glu Ala His Ala Ala Ile Asp
        355                 360                 365

Thr Phe Thr Lys Tyr Leu Asp Ile Asp Glu Asp Phe Ala Thr Val Leu
    370                 375                 380

```
Val Glu Glu Gly Phe Ser Thr Leu Glu Glu Leu Ala Tyr Val Pro Met
385                 390                 395                 400

Lys Glu Leu Leu Glu Ile Glu Gly Leu Asp Glu Pro Thr Val Glu Ala
            405                 410                 415

Leu Arg Glu Arg Ala Lys Asn Ala Leu Ala Thr Ile Ala Gln Ala Gln
        420                 425                 430

Glu Glu Ser Leu Gly Asp Asn Lys Pro Ala Asp Leu Leu Asn Leu
        435                 440                 445

Glu Gly Val Asp Arg Asp Leu Ala Phe Lys Leu Ala Ala Arg Gly Val
    450                 455                 460

Cys Thr Leu Glu Asp Leu Ala Glu Gln Gly Ile Asp Asp Leu Ala Asp
465                 470                 475                 480

Ile Glu Gly Leu Thr Asp Glu Lys Ala Gly Ala Leu Ile Met Ala Ala
                485                 490                 495

Arg Asn Ile Cys Trp Phe Gly Asp Glu Ala Gly Thr Asp Tyr Asp Ile
                500                 505                 510

Pro Thr Thr Glu Asn Leu Tyr Phe Gln Gly Ser Lys Gly Glu Glu Leu
            515                 520                 525

Phe Thr Gly Val Val Pro Ile Leu Val Glu Leu Asp Gly Asp Val Asn
        530                 535                 540

Gly His Lys Phe Ser Val Ser Gly Glu Gly Glu Gly Asp Ala Thr Tyr
545                 550                 555                 560

Gly Lys Leu Thr Leu Lys Phe Ile Cys Thr Thr Gly Lys Leu Pro Val
                565                 570                 575

Pro Trp Pro Thr Leu Val Thr Thr Phe Ala Tyr Gly Leu Gln Cys Phe
            580                 585                 590

Ala Arg Tyr Pro Asp His Met Lys Gln His Asp Phe Phe Lys Ser Ala
        595                 600                 605

Met Pro Glu Gly Tyr Val Gln Glu Arg Thr Ile Phe Phe Lys Asp Asp
    610                 615                 620

Gly Asn Tyr Lys Thr Arg Ala Glu Val Lys Phe Glu Gly Asp Thr Leu
625                 630                 635                 640

Val Asn Arg Ile Glu Leu Lys Gly Ile Asp Phe Lys Glu Asp Gly Asn
                645                 650                 655

Ile Leu Gly His Lys Leu Glu Tyr Asn Tyr Asn Ser His Asn Val Tyr
                660                 665                 670

Ile Met Ala Asp Lys Gln Lys Asn Gly Ile Lys Val Asn Phe Lys Ile
            675                 680                 685

Arg His Asn Ile Glu Asp Gly Ser Val Gln Leu Ala Asp His Tyr Gln
        690                 695                 700

Gln Asn Thr Pro Ile Gly Asp Gly Pro Val Leu Leu Pro Asp Asn His
705                 710                 715                 720

Tyr Leu Ser Thr Gln Ser Ala Leu Ser Lys Asp Pro Asn Glu Lys Arg
                725                 730                 735

Asp His Met Val Leu Leu Glu Phe Val Thr Ala Ala Gly Ile Thr His
            740                 745                 750

Gly Met Asp Glu Leu Tyr Lys Ile Glu Gly Arg Gly Gly Lys Pro Ile
        755                 760                 765

Pro Asn Pro Leu Leu Gly Leu Asp Ser Thr
    770                 775

<210> SEQ ID NO 67
<211> LENGTH: 150
```

<212> TYPE: PRT
<213> ORGANISM: Artificial Sequence
<220> FEATURE:
<223> OTHER INFORMATION: Synthetic Construct

<400> SEQUENCE: 67

```
Met Gly Cys Ser His His His His His Asn Pro Ser Leu Ile Arg
1               5                   10                  15

Ser Glu Ser Trp Ala Val Leu Lys Gly Asn Glu Ala Asn Leu Leu Asp
            20                  25                  30

Gly Asp Asp Asn Thr Gly Val Trp Tyr Ala Asn Tyr Lys Ile Gln Lys
                35                  40                  45

Ser Leu Ala Gly Glu Phe Ile Gly Leu Asp Leu Gly Lys Glu Ile Lys
        50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
                100                 105                 110

Asp Val Ile Glu Glu Ser Phe Glu Thr Pro Ile Ser Ala Lys Tyr Ile
            115                 120                 125

Arg Leu Thr Asn Leu Glu Gln Ala Phe Leu Val Leu Thr Phe Ser Glu
        130                 135                 140

Phe Ala Ile Val Ser Asp
145                 150
```

<210> SEQ ID NO 68
<211> LENGTH: 150
<212> TYPE: PRT
<213> ORGANISM: Artificial Sequence
<220> FEATURE:
<223> OTHER INFORMATION: Synthetic Construct

<400> SEQUENCE: 68

```
Met Gly Cys Ser His His His His His Asn Pro Ser Leu Ile Arg
1               5                   10                  15

Ser Glu Ser Trp Val Phe Ser Ile Gly Asn Glu Ala Asn Leu Leu Asp
            20                  25                  30

Gly Asp Asp Asn Thr Gly Val Trp Tyr Val Ala Trp Trp Pro Glu Thr
                35                  40                  45

Ser Leu Ala Gly Glu Phe Ile Gly Leu Asp Leu Gly Lys Glu Ile Lys
        50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
                100                 105                 110

Asp Val Ile Glu Glu Ser Phe Glu Thr Pro Ile Ser Ala Lys Tyr Ile
            115                 120                 125

Arg Leu Thr Asn Leu Glu Thr Tyr Phe His Glu Leu Thr Phe Ser Glu
        130                 135                 140

Phe Ala Ile Val Ser Asp
145                 150
```

<210> SEQ ID NO 69

```
<211> LENGTH: 164
<212> TYPE: PRT
<213> ORGANISM: Artificial Sequence
<220> FEATURE:
<223> OTHER INFORMATION: Synthetic Construct

<400> SEQUENCE: 69

Met Gly Ser Ser His His His His His Asn Pro Ser Leu Ile Arg
1               5                   10                  15

Ser Glu Ser Trp Glu Asp Ile Lys Gly Asn Glu Ala Asn Leu Leu Asp
                20                  25                  30

Gly Asp Asp Asn Thr Gly Val Trp Tyr Phe Asn Glu Val Phe Tyr Glu
            35                  40                  45

Ser Leu Ala Gly Glu Phe Ile Gly Leu Asp Leu Gly Lys Glu Ile Lys
50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
            100                 105                 110

Asp Val Ile Glu Glu Ser Phe Glu Thr Pro Ile Ser Ala Lys Tyr Ile
        115                 120                 125

Arg Leu Thr Asn Leu Glu Asp Lys Ile Leu Phe Leu Thr Phe Ser Glu
130                 135                 140

Phe Ala Ile Val Ser Asp Gly Gly Gly Ser Gly Gly Gly Ser
145                 150                 155                 160

Gly Gly Gly Cys

<210> SEQ ID NO 70
<211> LENGTH: 118
<212> TYPE: PRT
<213> ORGANISM: Artificial Sequence
<220> FEATURE:
<223> OTHER INFORMATION: Synthetic Construct

<400> SEQUENCE: 70

Met Gly Ser Ser His His His His His His Met Ser Asp Ser Glu Val
1               5                   10                  15

Asn Gln Glu Ala Lys Pro Glu Val Lys Pro Glu Val Lys Pro Glu Thr
                20                  25                  30

His Ile Asn Leu Lys Val Ser Asp Gly Ser Ser Glu Ile Phe Phe Lys
            35                  40                  45

Ile Lys Lys Thr Thr Pro Leu Arg Arg Leu Met Glu Ala Phe Ala Lys
50                  55                  60

Arg Gln Gly Lys Glu Met Asp Ser Leu Arg Phe Leu Tyr Asp Gly Ile
65                  70                  75                  80

Arg Ile Gln Ala Asp Gln Thr Pro Glu Asp Leu Asp Met Glu Asp Asn
                85                  90                  95

Asp Ile Ile Glu Ala His Arg Glu Gln Ile Gly Gly His Met Ala Ser
            100                 105                 110

Met Thr Gly Gly Gln Gln
        115

<210> SEQ ID NO 71
<211> LENGTH: 344
<212> TYPE: PRT
<213> ORGANISM: Artificial Sequence
```

```
<220> FEATURE:
<223> OTHER INFORMATION: Synthetic Construct

<400> SEQUENCE: 71

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly Ser Ser Gly Leu Val Pro Arg Gly Ser His Met Val Ser Lys
            100                 105                 110

Gly Glu Glu Asp Asn Met Ala Ile Ile Lys Glu Phe Met Arg Phe Lys
        115                 120                 125

Val His Met Glu Gly Ser Val Asn Gly His Glu Phe Glu Ile Glu Gly
    130                 135                 140

Glu Gly Glu Gly Arg Pro Tyr Glu Gly Thr Gln Thr Ala Lys Leu Lys
145                 150                 155                 160

Val Thr Lys Gly Gly Pro Leu Pro Phe Ala Trp Asp Ile Leu Ser Pro
                165                 170                 175

Gln Phe Met Tyr Gly Ser Lys Ala Tyr Val Lys His Pro Ala Asp Ile
            180                 185                 190

Pro Asp Tyr Leu Lys Leu Ser Phe Pro Glu Gly Phe Lys Trp Glu Arg
        195                 200                 205

Val Met Asn Phe Glu Asp Gly Gly Val Val Thr Val Thr Gln Asp Ser
    210                 215                 220

Ser Leu Gln Asp Gly Glu Phe Ile Tyr Lys Val Lys Leu Arg Gly Thr
225                 230                 235                 240

Asn Phe Pro Ser Asp Gly Pro Val Met Gln Lys Lys Thr Met Gly Trp
                245                 250                 255

Glu Ala Ser Ser Glu Arg Met Tyr Pro Glu Asp Gly Ala Leu Lys Gly
            260                 265                 270

Glu Ile Lys Gln Arg Leu Lys Leu Lys Asp Gly Gly His Tyr Asp Ala
        275                 280                 285

Glu Val Lys Thr Thr Tyr Lys Ala Lys Lys Pro Val Gln Leu Pro Gly
    290                 295                 300

Ala Tyr Asn Val Asn Ile Lys Leu Asp Ile Thr Ser His Asn Glu Asp
305                 310                 315                 320

Tyr Thr Ile Val Glu Gln Tyr Glu Arg Ala Glu Gly Arg His Ser Thr
                325                 330                 335

Gly Gly Met Asp Glu Leu Tyr Lys
            340

<210> SEQ ID NO 72
<211> LENGTH: 180
<212> TYPE: PRT
<213> ORGANISM: Artificial Sequence
<220> FEATURE:
<223> OTHER INFORMATION: Synthetic Construct
```

```
<400> SEQUENCE: 72

Met Lys Lys Thr Ala Ile Ala Ile Ala Val Ala Leu Ala Gly Phe Ala
1               5                   10                  15

Thr Val Ala Gln Ala Ala Gly Ser Ser His His His His His His Asn
            20                  25                  30

Pro Ser Leu Ile Arg Ser Glu Ser Trp Ala Ala Val Tyr Gly Asn Glu
        35                  40                  45

Ala Asn Leu Leu Asp Gly Asp Asn Thr Gly Val Trp Tyr Phe Asn
    50                  55                  60

Asp Asp Val Tyr Glu Ser Leu Ala Gly Glu Phe Ile Gly Leu Asp Leu
65                  70                  75                  80

Gly Lys Glu Ile Lys Leu Asp Gly Ile Arg Phe Val Ile Gly Lys Asn
                85                  90                  95

Gly Gly Gly Ser Ser Asp Lys Trp Asn Lys Phe Lys Leu Glu Tyr Ser
            100                 105                 110

Leu Asp Asn Glu Ser Trp Thr Thr Ile Lys Glu Tyr Asp Lys Thr Gly
        115                 120                 125

Ala Pro Ala Gly Lys Asp Val Ile Glu Glu Ser Phe Glu Thr Pro Ile
    130                 135                 140

Ser Ala Lys Tyr Ile Arg Leu Thr Asn Leu Glu His Glu Ala Ile Trp
145                 150                 155                 160

Leu Thr Phe Ser Glu Phe Ala Ile Val Ser Asp Asp Tyr Lys Asp Asp
                165                 170                 175

Asp Asp Lys Gly
            180

<210> SEQ ID NO 73
<211> LENGTH: 180
<212> TYPE: PRT
<213> ORGANISM: Artificial Sequence
<220> FEATURE:
<223> OTHER INFORMATION: Synthetic Construct

<400> SEQUENCE: 73

Met Lys Lys Thr Ala Ile Ala Ile Ala Val Ala Leu Ala Gly Phe Ala
1               5                   10                  15

Thr Val Ala Gln Ala Ala Gly Ser Ser His His His His His His Asn
            20                  25                  30

Pro Ser Leu Ile Arg Ser Glu Ser Trp Thr Val Glu Tyr Gly Asn Glu
        35                  40                  45

Ala Asn Leu Leu Asp Gly Asp Asn Thr Gly Val Trp Tyr Lys Lys
    50                  55                  60

Trp Trp Asp Ala Lys Ser Leu Ala Gly Glu Phe Ile Gly Leu Asp Leu
65                  70                  75                  80

Gly Lys Glu Ile Lys Leu Asp Gly Ile Arg Phe Val Ile Gly Lys Asn
                85                  90                  95

Gly Gly Gly Ser Ser Asp Lys Trp Asn Lys Phe Lys Leu Glu Tyr Ser
            100                 105                 110

Leu Asp Asn Glu Ser Trp Thr Thr Ile Lys Glu Tyr Asp Lys Thr Gly
        115                 120                 125

Ala Pro Ala Gly Lys Asp Val Ile Glu Glu Ser Phe Glu Thr Pro Ile
    130                 135                 140

Ser Ala Lys Tyr Ile Arg Leu Thr Asn Leu Glu Trp Leu Phe Asp Glu
145                 150                 155                 160

Leu Thr Phe Ser Glu Phe Ala Ile Val Ser Asp Asp Tyr Lys Asp Asp
```

165                 170                 175

Asp Asp Lys Gly
            180

<210> SEQ ID NO 74
<211> LENGTH: 163
<212> TYPE: PRT
<213> ORGANISM: Artificial Sequence
<220> FEATURE:
<223> OTHER INFORMATION: Synthetic Construct

<400> SEQUENCE: 74

Met Gly Ser Ser His His His His His Asn Pro Ser Leu Ile Arg
1               5                   10                  15

Ser Glu Ser Trp His Thr Tyr Asn Gly Asn Glu Ala Asn Leu Leu Asp
            20                  25                  30

Gly Asp Asp Asn Thr Gly Val Trp Tyr Asn Asn Ser Trp Phe Ser
        35                  40                  45

Ser Leu Ala Gly Glu Phe Ile Gly Leu Asp Leu Gly Lys Glu Ile Lys
    50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
                100                 105                 110

Asp Val Ile Glu Glu Ser Phe Glu Thr Pro Ile Ser Ala Lys Tyr Ile
            115                 120                 125

Arg Leu Thr Asn Leu Glu Ala Lys Asn Asn Leu Thr Phe Ser Glu Phe
        130                 135                 140

Ala Ile Val Ser Asp Gly Gly Gly Ser Gly Gly Gly Ser Gly
145                 150                 155                 160

Gly Gly Cys

<210> SEQ ID NO 75
<211> LENGTH: 122
<212> TYPE: PRT
<213> ORGANISM: Artificial Sequence
<220> FEATURE:
<223> OTHER INFORMATION: Synthetic Construct

<400> SEQUENCE: 75

Met Lys Ile Glu Met His His His His His Ala Met Gly Ser Asp
1               5                   10                  15

Lys Ile Ile His Leu Thr Asp Asp Ser Phe Asp Thr Asp Val Leu Lys
            20                  25                  30

Ala Asp Gly Ala Ile Leu Val Asp Phe Trp Ala Glu Trp Cys Gly Pro
        35                  40                  45

Cys Lys Met Ile Ala Pro Ile Leu Asp Glu Ile Ala Asp Glu Tyr Gln
    50                  55                  60

Gly Lys Leu Thr Val Ala Lys Leu Asn Ile Asp Gln Asn Pro Gly Thr
65                  70                  75                  80

Ala Pro Lys Tyr Gly Ile Arg Gly Ile Pro Thr Leu Leu Leu Phe Lys
                85                  90                  95

Asn Gly Glu Val Ala Ala Thr Lys Val Gly Ala Leu Ser Lys Gly Gln
                100                 105                 110

Leu Lys Glu Phe Leu Asp Ala Asn Leu Ala 115                 120

<210> SEQ ID NO 76
<211> LENGTH: 382
<212> TYPE: PRT
<213> ORGANISM: Artificial Sequence
<220> FEATURE:
<223> OTHER INFORMATION: Synthetic Construct

<400> SEQUENCE: 76

Met Gly Ser Ser His His His His His His Ala Met Gly Ser Asp Lys
1               5                   10                  15

Ile Ile His Leu Thr Asp Asp Ser Phe Asp Thr Asp Val Leu Lys Ala
            20                  25                  30

Asp Gly Ala Ile Leu Val Asp Phe Trp Ala Glu Trp Cys Gly Pro Cys
        35                  40                  45

Lys Met Ile Ala Pro Ile Leu Asp Glu Ile Ala Asp Glu Tyr Gln Gly
    50                  55                  60

Lys Leu Thr Val Ala Lys Leu Asn Ile Asp Gln Asn Pro Gly Thr Ala
65                  70                  75                  80

Pro Lys Tyr Gly Ile Arg Gly Ile Pro Thr Leu Leu Leu Phe Lys Asn
                85                  90                  95

Gly Glu Val Ala Ala Thr Lys Val Gly Ala Leu Ser Lys Gly Gln Leu
            100                 105                 110

Lys Glu Phe Leu Asp Ala Asn Leu Ala Leu Tyr Phe Gln Gly Ser Lys
        115                 120                 125

Gly Glu Glu Leu Phe Thr Gly Val Val Pro Ile Leu Val Glu Leu Asp
130                 135                 140

Gly Asp Val Asn Gly His Lys Phe Ser Val Ser Gly Glu Gly Glu Gly
145                 150                 155                 160

Asp Ala Thr Tyr Gly Lys Leu Thr Leu Lys Phe Ile Cys Thr Thr Gly
                165                 170                 175

Lys Leu Pro Val Pro Trp Pro Thr Leu Val Thr Thr Phe Ala Tyr Gly
            180                 185                 190

Leu Gln Cys Phe Ala Arg Tyr Pro Asp His Met Lys Gln His Asp Phe
        195                 200                 205

Phe Lys Ser Ala Met Pro Glu Gly Tyr Val Gln Glu Arg Thr Ile Phe
    210                 215                 220

Phe Lys Asp Asp Gly Asn Tyr Lys Thr Arg Ala Glu Val Lys Phe Glu
225                 230                 235                 240

Gly Asp Thr Leu Val Asn Arg Ile Glu Leu Lys Gly Ile Asp Phe Lys
                245                 250                 255

Glu Asp Gly Asn Ile Leu Gly His Lys Leu Glu Tyr Asn Tyr Asn Ser
            260                 265                 270

His Asn Val Tyr Ile Met Ala Asp Lys Gln Lys Asn Gly Ile Lys Val
        275                 280                 285

Asn Phe Lys Ile Arg His Asn Ile Glu Asp Gly Ser Val Gln Leu Ala
    290                 295                 300

Asp His Tyr Gln Gln Asn Thr Pro Ile Gly Asp Gly Pro Val Leu Leu
305                 310                 315                 320

Pro Asp Asn His Tyr Leu Ser Thr Gln Ser Ala Leu Ser Lys Asp Pro
                325                 330                 335

Asn Glu Lys Arg Asp His Met Val Leu Leu Glu Phe Val Thr Ala Ala
            340                 345                 350

Gly Ile Thr His Gly Met Asp Glu Leu Tyr Lys Ile Glu Gly Arg Gly

```
                355                 360                 365
Gly Lys Pro Ile Pro Asn Pro Leu Leu Gly Leu Asp Ser Thr
    370                 375                 380

<210> SEQ ID NO 77
<211> LENGTH: 149
<212> TYPE: PRT
<213> ORGANISM: Artificial Sequence
<220> FEATURE:
<223> OTHER INFORMATION: Synthetic Construct

<400> SEQUENCE: 77

Met Gly Cys Ser His His His His His Asn Pro Ser Leu Ile Arg
1               5                   10                  15

Ser Glu Ser Trp Pro Val Tyr Gly Asn Glu Ala Asn Leu Leu Asp Gly
            20                  25                  30

Asp Asp Asn Thr Gly Val Trp Tyr Tyr Ser Ser Gly Thr Tyr Phe Ser
        35                  40                  45

Leu Ala Gly Glu Phe Ile Gly Leu Asp Leu Gly Lys Glu Ile Lys Leu
    50                  55                  60

Asp Gly Ile Arg Phe Val Ile Gly Lys Asn Gly Gly Ser Ser Asp
65                  70                  75                  80

Lys Trp Asn Lys Phe Lys Leu Glu Tyr Ser Leu Asp Asn Glu Ser Trp
                85                  90                  95

Thr Thr Ile Lys Glu Tyr Asp Lys Thr Gly Ala Pro Ala Gly Lys Asp
            100                 105                 110

Val Ile Glu Glu Ser Phe Glu Thr Pro Ile Ser Ala Lys Tyr Ile Arg
        115                 120                 125

Leu Thr Asn Leu Glu Leu Lys Tyr Tyr Gly Leu Thr Phe Ser Glu Phe
    130                 135                 140

Ala Ile Val Ser Asp
145

<210> SEQ ID NO 78
<211> LENGTH: 150
<212> TYPE: PRT
<213> ORGANISM: Artificial Sequence
<220> FEATURE:
<223> OTHER INFORMATION: Synthetic Construct

<400> SEQUENCE: 78

Met Gly Cys Ser His His His His His Asn Pro Ser Leu Ile Arg
1               5                   10                  15

Ser Glu Ser Trp Tyr Ile Gly Val Gly Asn Glu Ala Asn Leu Leu Asp
            20                  25                  30

Gly Asp Asp Asn Thr Gly Val Trp Tyr Glu Lys Tyr His Leu Tyr Val
        35                  40                  45

Ser Leu Ala Gly Glu Phe Ile Gly Leu Asp Leu Gly Lys Glu Ile Lys
    50                  55                  60

Leu Asp Gly Ile Arg Phe Val Ile Gly Lys Asn Gly Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
            100                 105                 110

Asp Val Ile Glu Glu Ser Phe Glu Thr Pro Ile Ser Ala Lys Tyr Ile
        115                 120                 125
```

```
Arg Leu Thr Asn Leu Glu Val Gly Arg Lys Ser Leu Thr Phe Ser Glu
            130                 135                 140

Phe Ala Ile Val Ser Asp
145                 150

<210> SEQ ID NO 79
<211> LENGTH: 164
<212> TYPE: PRT
<213> ORGANISM: Artificial Sequence
<220> FEATURE:
<223> OTHER INFORMATION: Synthetic Construct

<400> SEQUENCE: 79

Met Gly Ser Ser His His His His His His Asn Pro Ser Leu Ile Arg
1               5                   10                  15

Ser Glu Ser Trp Trp Ile Arg Ser Gly Asn Glu Ala Asn Leu Leu Asp
            20                  25                  30

Gly Asp Asp Asn Thr Gly Val Trp Tyr Asp Asn Leu Tyr Trp Tyr Arg
            35                  40                  45

Ser Leu Ala Gly Glu Phe Ile Gly Leu Asp Leu Gly Lys Glu Ile Lys
    50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
            100                 105                 110

Asp Val Ile Glu Glu Ser Phe Glu Thr Pro Ile Ser Ala Lys Tyr Ile
            115                 120                 125

Arg Leu Thr Asn Leu Glu Asn Lys Tyr Gly Ile Leu Thr Phe Ser Glu
            130                 135                 140

Phe Ala Ile Val Ser Asp Gly Gly Gly Ser Gly Gly Gly Ser
145                 150                 155                 160

Gly Gly Gly Cys

<210> SEQ ID NO 80
<211> LENGTH: 150
<212> TYPE: PRT
<213> ORGANISM: Artificial Sequence
<220> FEATURE:
<223> OTHER INFORMATION: Synthetic Construct

<400> SEQUENCE: 80

Met Gly Cys Ser His His His His His His Asn Pro Ser Leu Ile Arg
1               5                   10                  15

Ser Glu Ser Trp Arg Arg Trp Ser Gly Asn Glu Ala Asn Leu Leu Asp
            20                  25                  30

Gly Asp Asp Asn Thr Gly Val Trp Tyr Val Thr Trp Pro Phe Ser Glu
            35                  40                  45

Ser Leu Ala Gly Glu Phe Ile Gly Leu Asp Leu Gly Lys Glu Ile Lys
    50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
            100                 105                 110
```

```
Asp Val Ile Glu Glu Ser Phe Glu Thr Pro Ile Ser Ala Lys Tyr Ile
            115                 120                 125

Arg Leu Thr Asn Leu Glu Asn Ile Asn Lys Trp Leu Thr Phe Ser Glu
        130                 135                 140

Phe Ala Ile Val Ser Asp
145                 150

<210> SEQ ID NO 81
<211> LENGTH: 150
<212> TYPE: PRT
<213> ORGANISM: Artificial Sequence
<220> FEATURE:
<223> OTHER INFORMATION: Synthetic Construct

<400> SEQUENCE: 81

Met Gly Cys Ser His His His His His Asn Pro Ser Leu Ile Arg
1               5                   10                  15

Ser Glu Ser Trp Tyr Ala Ile Phe Gly Asn Glu Ala Asn Leu Leu Asp
            20                  25                  30

Gly Asp Asp Asn Thr Gly Val Trp Tyr His Ser Arg Asn Tyr Tyr Lys
        35                  40                  45

Ser Leu Ala Gly Glu Phe Ile Gly Leu Asp Leu Gly Lys Glu Ile Lys
    50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
            100                 105                 110

Asp Val Ile Glu Glu Ser Phe Glu Thr Pro Ile Ser Ala Lys Tyr Ile
        115                 120                 125

Arg Leu Thr Asn Leu Glu His Leu Trp Gly His Leu Thr Phe Ser Glu
    130                 135                 140

Phe Ala Ile Val Ser Asp
145                 150

<210> SEQ ID NO 82
<211> LENGTH: 164
<212> TYPE: PRT
<213> ORGANISM: Artificial Sequence
<220> FEATURE:
<223> OTHER INFORMATION: Synthetic Construct

<400> SEQUENCE: 82

Met Gly Ser Ser His His His His His His Asn Pro Ser Leu Ile Arg
1               5                   10                  15

Ser Glu Ser Trp Gly Val Ile Ala Gly Asn Glu Ala Asn Leu Leu Asp
            20                  25                  30

Gly Asp Asp Asn Thr Gly Val Trp Tyr Thr Lys Ser Asn Asn His Leu
        35                  40                  45

Ser Leu Ala Gly Glu Phe Ile Gly Leu Asp Leu Gly Lys Glu Ile Lys
    50                  55                  60

Leu Asp Gly Ile Arg Phe Val Ile Gly Lys Asn Gly Gly Ser Ser
65                  70                  75                  80

Asp Lys Trp Asn Lys Phe Lys Leu Glu Tyr Ser Leu Asp Asn Glu Ser
                85                  90                  95

Trp Thr Thr Ile Lys Glu Tyr Asp Lys Thr Gly Ala Pro Ala Gly Lys
            100                 105                 110
```

```
Asp Val Ile Glu Glu Ser Phe Glu Thr Pro Ile Ser Ala Lys Tyr Ile
            115                 120                 125

Arg Leu Thr Asn Leu Glu Ala Val Phe Phe Asn Leu Thr Phe Ser Glu
        130                 135                 140

Phe Ala Ile Val Ser Asp Gly Gly Gly Ser Gly Gly Gly Gly Gly Ser
145                 150                 155                 160

Gly Gly Gly Cys
```

<210> SEQ ID NO 83
<211> LENGTH: 163
<212> TYPE: PRT
<213> ORGANISM: Artificial Sequence
<220> FEATURE:
<223> OTHER INFORMATION: Synthetic Construct

<400> SEQUENCE: 83

```
Met Gly Ser Ser His His His His His His Asn Pro Ser Leu Ile Arg
1               5                   10                  15

Ser Glu Ser Trp Val Lys Tyr Phe Gly Asn Glu Ala Asn Leu Leu Asp
            20                  25                  30

Gly Asp Asp Asn Thr Gly Val Trp Tyr Phe Trp His Thr Ala Ser Ser
        35                  40                  45

Leu Ala Gly Glu Phe Ile Gly Leu Asp Leu Gly Lys Glu Ile Lys Leu
    50                  55                  60

Asp Gly Ile Arg Phe Val Ile Gly Lys Asn Gly Gly Ser Ser Asp
65                  70                  75                  80

Lys Trp Asn Lys Phe Lys Leu Glu Tyr Ser Leu Asp Asn Glu Ser Trp
                85                  90                  95

Thr Thr Ile Lys Glu Tyr Asp Lys Thr Gly Ala Pro Ala Gly Lys Asp
            100                 105                 110

Val Ile Glu Glu Ser Phe Glu Thr Pro Ile Ser Ala Lys Tyr Ile Arg
        115                 120                 125

Leu Thr Asn Leu Glu Gln Tyr Ile Asn Ile Leu Thr Phe Ser Glu Phe
    130                 135                 140

Ala Ile Val Ser Asp Gly Gly Gly Ser Gly Gly Gly Gly Gly Ser Gly
145                 150                 155                 160

Gly Gly Cys
```

<210> SEQ ID NO 84
<211> LENGTH: 180
<212> TYPE: PRT
<213> ORGANISM: Artificial Sequence
<220> FEATURE:
<223> OTHER INFORMATION: Synthetic Construct

<400> SEQUENCE: 84

```
Met Lys Lys Thr Ala Ile Ala Ile Ala Val Ala Leu Ala Gly Phe Ala
1               5                   10                  15

Thr Val Ala Gln Ala Ala Gly Ser Ser His His His His His His Asn
            20                  25                  30

Pro Ser Leu Ile Arg Ser Glu Ser Trp Thr Lys Ile Arg Gly Asn Glu
        35                  40                  45

Ala Asn Leu Leu Asp Gly Asp Asp Asn Thr Gly Val Trp Tyr Ala Leu
    50                  55                  60

Thr Phe Lys Asn Ile His Glu Trp Tyr Trp Val Val Ser Ser Leu Ala
65                  70                  75                  80
```

Gly Glu Phe Ile Gly Leu Asp Leu Gly Lys Glu Ile Lys Leu Asp Gly
            85                  90                  95

Ile Arg Phe Val Ile Gly Lys Asn Gly Gly Ser Ser Asp Lys Trp
            100                 105                 110

Asn Lys Phe Lys Leu Glu Tyr Ser Leu Asp Asn Glu Ser Trp Thr Thr
            115                 120                 125

Ile Lys Glu Tyr Asp Lys Thr Gly Ala Pro Ala Gly Lys Asp Val Ile
            130                 135                 140

Glu Glu Ser Phe Glu Thr Pro Ile Ser Ala Lys Tyr Ile Arg Leu Thr
145                 150                 155                 160

Asn Leu Glu Asp Tyr Ile Tyr Asp Leu Thr Phe Ser Glu Phe Ala Ile
            165                 170                 175

Val Ser Asp Gly
            180

<210> SEQ ID NO 85
<211> LENGTH: 172
<212> TYPE: PRT
<213> ORGANISM: Artificial Sequence
<220> FEATURE:
<223> OTHER INFORMATION: Synthetic Construct

<400> SEQUENCE: 85

Met Gly Ser Ser His His His His His His Asn Pro Ser Leu Ile Arg
1               5                   10                  15

Ser Glu Ser Trp Val Gly Ser Lys Gly Asn Glu Ala Asn Leu Leu Asp
            20                  25                  30

Gly Asp Asp Asn Thr Gly Val Trp Tyr Pro Trp Phe Pro Lys Ala Ile
            35                  40                  45

Phe Phe Lys Asn Arg Glu Phe Gly Ser Leu Ala Gly Glu Phe Ile Gly
            50                  55                  60

Leu Asp Leu Gly Lys Glu Ile Lys Leu Asp Gly Ile Arg Phe Val Ile
65                  70                  75                  80

Gly Lys Asn Gly Gly Ser Ser Asp Lys Trp Asn Lys Phe Lys Leu
            85                  90                  95

Glu Tyr Ser Leu Asp Asn Glu Ser Trp Thr Thr Ile Lys Glu Tyr Asp
            100                 105                 110

Lys Thr Gly Ala Pro Ala Gly Lys Asp Val Ile Glu Glu Ser Phe Glu
            115                 120                 125

Thr Pro Ile Ser Ala Lys Tyr Ile Arg Leu Thr Asn Leu Glu Tyr Val
            130                 135                 140

Ser Val Ile Leu Thr Phe Ser Glu Phe Ala Ile Val Ser Asp Gly Gly
145                 150                 155                 160

Gly Gly Ser Gly Gly Gly Gly Ser Gly Gly Cys
            165                 170

<210> SEQ ID NO 86
<211> LENGTH: 256
<212> TYPE: PRT
<213> ORGANISM: Artificial Sequence
<220> FEATURE:
<223> OTHER INFORMATION: Synthetic Construct

<400> SEQUENCE: 86

Met Gly Ser Ser His His His His His His Ser Ser Gly Leu Val Pro
1               5                   10                  15

Arg Gly Ser His Met Val Ser Lys Gly Glu Glu Asp Asn Met Ala Ile
            20                  25                  30

Ile Lys Glu Phe Met Arg Phe Lys Val His Met Glu Gly Ser Val Asn
         35                  40                  45

Gly His Glu Phe Glu Ile Glu Gly Glu Gly Arg Pro Tyr Glu
     50                  55                  60

Gly Thr Gln Thr Ala Lys Leu Lys Val Thr Lys Gly Gly Pro Leu Pro
 65                  70                  75                  80

Phe Ala Trp Asp Ile Leu Ser Pro Gln Phe Met Tyr Gly Ser Lys Ala
                 85                  90                  95

Tyr Val Lys His Pro Ala Asp Ile Pro Asp Tyr Leu Lys Leu Ser Phe
                100                 105                 110

Pro Glu Gly Phe Lys Trp Glu Arg Val Met Asn Phe Glu Asp Gly Gly
             115                 120                 125

Val Val Thr Val Thr Gln Asp Ser Ser Leu Gln Asp Gly Glu Phe Ile
 130                 135                 140

Tyr Lys Val Lys Leu Arg Gly Thr Asn Phe Pro Ser Asp Gly Pro Val
145                 150                 155                 160

Met Gln Lys Lys Thr Met Gly Trp Glu Ala Ser Ser Glu Arg Met Tyr
                165                 170                 175

Pro Glu Asp Gly Ala Leu Lys Gly Glu Ile Lys Gln Arg Leu Lys Leu
            180                 185                 190

Lys Asp Gly Gly His Tyr Asp Ala Glu Val Lys Thr Thr Tyr Lys Ala
        195                 200                 205

Lys Lys Pro Val Gln Leu Pro Gly Ala Tyr Asn Val Asn Ile Lys Leu
    210                 215                 220

Asp Ile Thr Ser His Asn Glu Asp Tyr Thr Ile Val Glu Gln Tyr Glu
225                 230                 235                 240

Arg Ala Glu Gly Arg His Ser Thr Gly Gly Met Asp Glu Leu Tyr Lys
                245                 250                 255

<210> SEQ ID NO 87
<211> LENGTH: 172
<212> TYPE: PRT
<213> ORGANISM: Artificial Sequence
<220> FEATURE:
<223> OTHER INFORMATION: Synthetic Construct

<400> SEQUENCE: 87

Met Gly Ser Ser His His His His His His Asn Pro Ser Leu Ile Arg
 1               5                  10                  15

Ser Glu Ser Trp Asp Thr Thr Ala Gly Asn Glu Ala Asn Leu Leu Asp
             20                  25                  30

Gly Asp Asp Asn Thr Gly Val Trp Tyr Ile Thr Gly Trp Val His Arg
         35                  40                  45

Arg Tyr Val Trp Glu Thr Gln Leu Ser Leu Ala Gly Glu Phe Ile Gly
     50                  55                  60

Leu Asp Leu Gly Lys Glu Ile Lys Leu Asp Gly Ile Arg Phe Val Ile
 65                  70                  75                  80

Gly Lys Asn Gly Gly Ser Ser Asp Lys Trp Asn Lys Phe Lys Leu
                 85                  90                  95

Glu Tyr Ser Leu Asp Asn Glu Ser Trp Thr Thr Ile Lys Glu Tyr Asp
                100                 105                 110

Lys Thr Gly Ala Pro Ala Gly Lys Asp Val Ile Glu Glu Ser Phe Glu
            115                 120                 125

Thr Pro Ile Ser Ala Lys Tyr Ile Arg Leu Thr Asn Met Glu Asn Ile
        130                 135                 140

Asn Lys Trp Leu Thr Phe Ser Glu Phe Ala Ile Val Ser Asp Gly Gly
145                 150                 155                 160

Gly Gly Ser Gly Gly Gly Ser Gly Gly Gly Cys
            165                 170

<210> SEQ ID NO 88
<211> LENGTH: 284
<212> TYPE: PRT
<213> ORGANISM: Artificial Sequence
<220> FEATURE:
<223> OTHER INFORMATION: Synthetic Construct

<400> SEQUENCE: 88

Met Gly Ser Ser His His His His His Ser Lys Gly Glu Glu Leu
1               5                   10                  15

Phe Thr Gly Val Val Pro Ile Leu Val Glu Leu Asp Gly Asp Val Asn
                20                  25                  30

Gly His Lys Phe Ser Val Ser Gly Glu Gly Glu Gly Asp Ala Thr Tyr
            35                  40                  45

Gly Lys Leu Thr Leu Lys Phe Ile Cys Thr Thr Gly Lys Leu Pro Val
        50                  55                  60

Pro Trp Pro Thr Leu Val Thr Thr Phe Ala Tyr Gly Leu Gln Cys Phe
65                  70                  75                  80

Ala Arg Tyr Pro Asp His Met Lys Gln His Asp Phe Phe Lys Ser Ala
                85                  90                  95

Met Pro Glu Gly Tyr Val Gln Glu Arg Thr Ile Phe Phe Lys Asp Asp
            100                 105                 110

Gly Asn Tyr Lys Thr Arg Ala Glu Val Lys Phe Glu Gly Asp Thr Leu
        115                 120                 125

Val Asn Arg Ile Glu Leu Lys Gly Ile Asp Phe Lys Glu Asp Gly Asn
    130                 135                 140

Ile Leu Gly His Lys Leu Glu Tyr Asn Tyr Asn Ser His Asn Val Tyr
145                 150                 155                 160

Ile Met Ala Asp Lys Gln Lys Asn Gly Ile Lys Val Asn Phe Lys Ile
                165                 170                 175

Arg His Asn Ile Glu Asp Gly Ser Val Gln Leu Ala Asp His Tyr Gln
            180                 185                 190

Gln Asn Thr Pro Ile Gly Asp Gly Pro Val Leu Leu Pro Asp Asn His
        195                 200                 205

Tyr Leu Ser Thr Gln Ser Ala Leu Ser Lys Asp Pro Asn Glu Lys Arg
    210                 215                 220

Asp His Met Val Leu Leu Glu Phe Val Thr Ala Ala Gly Ile Thr His
225                 230                 235                 240

Gly Met Asp Glu Leu Tyr Lys Ile Glu Gly Arg Gly Glu Gln Lys Leu
                245                 250                 255

Ile Ser Glu Glu Asp Leu Gly Gln Lys Leu Ile Ser Glu Glu Asp
            260                 265                 270

Leu Gly Glu Gln Lys Leu Ile Ser Glu Glu Asp Leu
        275                 280

<210> SEQ ID NO 89
<211> LENGTH: 148
<212> TYPE: PRT
<213> ORGANISM: Artificial Sequence
<220> FEATURE:
<223> OTHER INFORMATION: Synthetic Construct

<400> SEQUENCE: 89

Met Gly Ser Ser His His His His His Asn Pro Ser Leu Ile Arg
1               5                   10                  15

Ser Glu Ser Trp Ala His Ile Trp Gly Asn Glu Ala Asn Leu Leu Asp
            20                  25                  30

Gly Asp Asp Asn Thr Gly Val Trp Tyr Trp Val Gly Ser Leu Ala
            35                  40                  45

Gly Glu Phe Ile Gly Leu Asp Leu Gly Lys Glu Ile Lys Leu Asp Gly
            50                  55                  60

Ile Arg Phe Val Ile Gly Lys Asn Gly Gly Ser Ser Asp Lys Trp
65                  70                  75                  80

Asn Lys Phe Lys Leu Glu Tyr Ser Leu Asp Asn Glu Ser Trp Thr Thr
                85                  90                  95

Ile Lys Glu Tyr Asp Lys Thr Gly Ala Pro Ala Gly Lys Asp Val Ile
            100                 105                 110

Glu Glu Ser Phe Glu Thr Pro Ile Ser Ala Lys Tyr Ile Arg Leu Thr
            115                 120                 125

Asn Leu Glu Phe Gly Thr Gly Ser Leu Thr Phe Ser Glu Phe Ala Ile
            130                 135                 140

Val Ser Asp Cys
145

<210> SEQ ID NO 90
<211> LENGTH: 141
<212> TYPE: PRT
<213> ORGANISM: Artificial Sequence
<220> FEATURE:
<223> OTHER INFORMATION: Synthetic Construct

<400> SEQUENCE: 90

Gln Val Gln Leu Val Gln Ser Gly Gly Gly Leu Val Gln Pro Gly Gly
1               5                   10                  15

Ser Leu Arg Leu Ser Cys Ala Ala Ser Asp Tyr Gly Gln Gln Gly Tyr
            20                  25                  30

Thr Thr Pro Trp Thr Phe Met Ser Trp Val Arg Gln Ala Pro Gly Lys
            35                  40                  45

Ala Leu Glu Trp Ile Gly Tyr Ile His His Ser Gly Ser Thr Asn Tyr
        50                  55                  60

Asn Pro Ser Leu Lys Ser Arg Val Thr Ile Ser Arg Asp Asn Ser Lys
65                  70                  75                  80

Asn Thr Leu Tyr Leu Gln Met Asn Thr Leu Arg Ala Glu Asp Thr Ala
                85                  90                  95

Met Tyr Tyr Cys Ala Arg Gly Asn Leu Ala Ile Arg Tyr Trp Gly Gln
            100                 105                 110

Gly Thr Leu Val Thr Val Ser Ser Gly Gln Ala Gly His His His
            115                 120                 125

His His His Gly Asp Tyr Lys Asp Asp Asp Lys Gly
        130                 135                 140

<210> SEQ ID NO 91
<211> LENGTH: 52
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(27)

<223> OTHER INFORMATION: n is a, c, g, or t

<400> SEQUENCE: 91
cgttctgaat cctggnnnnn nnnnnnnggg aatgaagcca atttattaga tg    52

<210> SEQ ID NO 92
<211> LENGTH: 26
<212> TYPE: DNA
<213> ORGANISM: Artificial Sequence
<220> FEATURE:
<223> OTHER INFORMATION: Synthetic Construct

<400> SEQUENCE: 92
ccaggattca gaacgaatta aagaag    26

<210> SEQ ID NO 93
<211> LENGTH: 27
<212> TYPE: DNA
<213> ORGANISM: Artificial Sequence
<220> FEATURE:
<223> OTHER INFORMATION: Synthetic Construct

<400> SEQUENCE: 93
tctcttgcag gagaattcat tggattg    27

<210> SEQ ID NO 94
<211> LENGTH: 29
<212> TYPE: DNA
<213> ORGANISM: Artificial Sequence
<220> FEATURE:
<223> OTHER INFORMATION: Synthetic Construct

<400> SEQUENCE: 94
ttccagatta gtcagacgaa tgtacttag    29

<210> SEQ ID NO 95
<211> LENGTH: 60
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(36)
<223> OTHER INFORMATION: n is a, c, g, or t

<400> SEQUENCE: 95
ttctcctgca agagannnnn nnnnnnnnnn nnnnnatac caaacaccgg tgttatcgtc    60

<210> SEQ ID NO 96
<211> LENGTH: 55
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(30)
<223> OTHER INFORMATION: n is a, c, g, or t

<400> SEQUENCE: 96
ctgactaatc tggaannnnn nnnnnnnnnn ctgacttta gtgagtttgc aattg    55

<210> SEQ ID NO 97
<211> LENGTH: 41
<212> TYPE: DNA
<213> ORGANISM: Artificial Sequence

```
<220> FEATURE:
<223> OTHER INFORMATION: Synthetic Construct

<400> SEQUENCE: 97
catcatcatc atcacaaccc ttctttaatt cgttctgaat c                          41

<210> SEQ ID NO 98
<211> LENGTH: 50
<212> TYPE: DNA
<213> ORGANISM: Artificial Sequence
<220> FEATURE:
<223> OTHER INFORMATION: Synthetic Construct

<400> SEQUENCE: 98
ggctttgtta gcagctcagc agtcagacac aattgcaaac tcactaaaag                 50

<210> SEQ ID NO 99
<211> LENGTH: 28
<212> TYPE: DNA
<213> ORGANISM: Artificial Sequence
<220> FEATURE:
<223> OTHER INFORMATION: Synthetic Construct

<400> SEQUENCE: 99
gtgatgatga tgatgatggc tgctgccc                                         28

<210> SEQ ID NO 100
<211> LENGTH: 28
<212> TYPE: DNA
<213> ORGANISM: Artificial Sequence
<220> FEATURE:
<223> OTHER INFORMATION: Synthetic Construct

<400> SEQUENCE: 100
gctgctaaca aagcccgaaa ggaagctg                                         28

<210> SEQ ID NO 101
<211> LENGTH: 36
<212> TYPE: DNA
<213> ORGANISM: Artificial Sequence
<220> FEATURE:
<223> OTHER INFORMATION: Synthetic Construct

<400> SEQUENCE: 101
agaagggttg tgatgatgat gatgatggct gctgcc                                36

<210> SEQ ID NO 102
<211> LENGTH: 32
<212> TYPE: DNA
<213> ORGANISM: Artificial Sequence
<220> FEATURE:
<223> OTHER INFORMATION: Synthetic Construct

<400> SEQUENCE: 102
catcacaacc cttctttaat tcgttctgaa tc                                    32

<210> SEQ ID NO 103
<211> LENGTH: 47
<212> TYPE: DNA
<213> ORGANISM: Artificial Sequence
<220> FEATURE:
<223> OTHER INFORMATION: Synthetic Construct

<400> SEQUENCE: 103
ggctttgtta gcagctcagt cagacacaat tgcaaactca ctaaaag                    47
```

<210> SEQ ID NO 104
<211> LENGTH: 30
<212> TYPE: DNA
<213> ORGANISM: Artificial Sequence
<220> FEATURE:
<223> OTHER INFORMATION: Synthetic Construct

<400> SEQUENCE: 104
tgcagcagcc atcatcatca tcatcacaac                                          30

<210> SEQ ID NO 105
<211> LENGTH: 32
<212> TYPE: DNA
<213> ORGANISM: Artificial Sequence
<220> FEATURE:
<223> OTHER INFORMATION: Synthetic Construct

<400> SEQUENCE: 105
atgatggctg ctgcacatgg tatatctcct tc                                       32

<210> SEQ ID NO 106
<211> LENGTH: 29
<212> TYPE: DNA
<213> ORGANISM: Artificial Sequence
<220> FEATURE:
<223> OTHER INFORMATION: Synthetic Construct

<400> SEQUENCE: 106
atggctgcag cccatggtat atctccttc                                           29

<210> SEQ ID NO 107
<211> LENGTH: 30
<212> TYPE: DNA
<213> ORGANISM: Artificial Sequence
<220> FEATURE:
<223> OTHER INFORMATION: Synthetic Construct

<400> SEQUENCE: 107
atgggctgca gccatcatca tcatcatcac                                          30

<210> SEQ ID NO 108
<211> LENGTH: 87
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(60)
<223> OTHER INFORMATION: n is a, c, g, or t

<400> SEQUENCE: 108
accggtgttt ggtatnnnnn nnnnnnnnnn nnnnnnnnnn nnnnnnnnn nnnnnnnnn            60 tctcttgcag gagaattcat tggattg                                             87

<210> SEQ ID NO 109
<211> LENGTH: 24
<212> TYPE: DNA
<213> ORGANISM: Artificial Sequence
<220> FEATURE:
<223> OTHER INFORMATION: Synthetic Construct

<400> SEQUENCE: 109
ggctagtccc aggagggtgg tggc                                                24

```
<210> SEQ ID NO 110
<211> LENGTH: 44
<212> TYPE: DNA
<213> ORGANISM: Artificial Sequence
<220> FEATURE:
<223> OTHER INFORMATION: Synthetic Construct

<400> SEQUENCE: 110
ctcctgggac tagccgtcag acacaattgc aaactcacta aaag                    44

<210> SEQ ID NO 111
<211> LENGTH: 30
<212> TYPE: DNA
<213> ORGANISM: Artificial Sequence
<220> FEATURE:
<223> OTHER INFORMATION: Synthetic Construct

<400> SEQUENCE: 111
ataccaaaca ccggtgttat cgtctccatc                                    30

<210> SEQ ID NO 112
<211> LENGTH: 68
<212> TYPE: DNA
<213> ORGANISM: Artificial Sequence
<220> FEATURE:
<223> OTHER INFORMATION: Synthetic Construct

<400> SEQUENCE: 112
ccctccaccc gagccaccac cgccgctgcc acctccaccg tcagacacaa ttgcaaactc    60
actaaaag                                                            68

<210> SEQ ID NO 113
<211> LENGTH: 46
<212> TYPE: DNA
<213> ORGANISM: Artificial Sequence
<220> FEATURE:
<223> OTHER INFORMATION: Synthetic Construct

<400> SEQUENCE: 113
ggctcgggtg gagggtgctg agctgctaac aaagcccgaa aggaag                  46
```